United States Patent
Poulos

(10) Patent No.: US 9,211,195 B2
(45) Date of Patent: Dec. 15, 2015

(54) EXPANDABLE INTERBODY IMPLANT AND METHOD

(71) Applicant: Nicholas Poulos, Belleville, IL (US)

(72) Inventor: Nicholas Poulos, Belleville, IL (US)

(*) Notice: Subject to any disclaimer, the term of this patent is extended or adjusted under 35 U.S.C. 154(b) by 0 days.

(21) Appl. No.: 14/520,892

(22) Filed: Oct. 22, 2014

(65) Prior Publication Data

US 2015/0045891 A1 Feb. 12, 2015

Related U.S. Application Data

(63) Continuation of application No. 13/543,126, filed on Jul. 6, 2012, now Pat. No. 8,906,099, which is a continuation-in-part of application No. 12/899,625, filed on Oct. 7, 2010, and a continuation-in-part of application No. 13/030,618, filed on Feb. 18, 2011, now Pat. No. 8,480,748.

(60) Provisional application No. 61/610,198, filed on Mar. 13, 2012, provisional application No. 61/251,002, filed on Oct. 13, 2009, provisional application No. 61/356,851, filed on Jun. 21, 2010.

(51) Int. Cl.
| | |
|---|---|
| *A61F 2/44* | (2006.01) |
| *G06F 1/32* | (2006.01) |
| *H04W 4/02* | (2009.01) |
| *H04W 4/00* | (2009.01) |
| *H04W 64/00* | (2009.01) |
| *H04W 48/04* | (2009.01) |
| *H04M 1/725* | (2006.01) |

(Continued)

(52) U.S. Cl.
CPC .............. *A61F 2/4455* (2013.01); *A61B 17/025* (2013.01); *G06F 1/3206* (2013.01); *G06F 1/3209* (2013.01); *H04M 1/72569* (2013.01); *H04W 4/001* (2013.01); *H04W 4/02* (2013.01); *H04W 48/04* (2013.01); *H04W 64/00* (2013.01); *A61B 2017/00261* (2013.01); *A61B 2017/0256* (2013.01); *A61F 2002/30579* (2013.01); *A61F 2002/4475* (2013.01)

(58) Field of Classification Search
CPC .................. A61F 2/4455; A61F 2/447; A61F 2002/4475; A61F 2/4611
USPC .......................................... 623/17.11–17.16
See application file for complete search history.

(56) References Cited

U.S. PATENT DOCUMENTS

| | | | |
|---|---|---|---|
| 6,080,193 | A | 6/2000 | Hochshuler et al. |
| 6,997,929 | B2 | 2/2006 | Manzi et al. |

(Continued)

OTHER PUBLICATIONS

SpineWave StaXx®XD Expandable Device—In Situ Distraction Minimal Retraction web page by Spine Wave, Inc. of Shelton, CT.

(Continued)

*Primary Examiner* — Eduardo C Robert
*Assistant Examiner* — Julianna N Harvey
(74) *Attorney, Agent, or Firm* — Polster, Lieder, Woodruff & Lucchesi LC

(57) ABSTRACT

An intervertebral implant that can be surgically introduced between adjacent vertebrae and expanded in situ to occupy an optimal space between the vertebrae. The implant is inserted into the evacuated disc space obliquely and then oriented so as to extend laterally across the anterior adjacent vertebrae with its outer ends of the implant supported by the cortical rims on the opposite sides of the vertebrae. The implant has two body members with a space therebetween so the implant may be then distracted and a spacer of predetermined thickness that may be inserted within the space between the body members so as to maintain a desired amount of distraction. The upper and lower surfaces of the implant may have a desired lordotic angle. A method of using an implant is disclosed which permits endoscopic visualization of the disc space.

29 Claims, 47 Drawing Sheets

(51) Int. Cl.
*A61B 17/02* (2006.01)
*A61B 17/00* (2006.01)
*A61F 2/30* (2006.01)

(56) References Cited

U.S. PATENT DOCUMENTS

| | | | |
|---|---|---|---|
| 7,311,713 | B2 | 12/2007 | Johnson et al. |
| 7,867,277 | B1 | 1/2011 | Tohmeh |
| 7,905,886 | B1 * | 3/2011 | Curran et al. .................... 606/99 |
| 7,985,256 | B2 | 7/2011 | Grotz et al. |
| 8,070,813 | B2 | 12/2011 | Grotz et al. |
| 8,192,495 | B2 | 6/2012 | Simpson et al. |
| 8,377,137 | B2 | 2/2013 | Sournac et al. |
| 8,435,296 | B2 | 5/2013 | Kadaba et al. |
| 8,454,695 | B2 | 6/2013 | Grotz et al. |
| 8,663,331 | B2 | 3/2014 | McClellan, III et al. |
| 8,696,751 | B2 | 4/2014 | Ashley et al. |
| 8,932,355 | B2 | 1/2015 | Grotz et al. |
| 2003/0187506 | A1 | 10/2003 | Ross et al. |
| 2004/0230309 | A1 | 11/2004 | DiMauro et al. |
| 2005/0027362 | A1 | 2/2005 | Williams et al. |
| 2005/0055029 | A1 | 3/2005 | Marik et al. |
| 2005/0187559 | A1 | 8/2005 | Raymond et al. |
| 2005/0187625 | A1 | 8/2005 | Wolek et al. |
| 2005/0216081 | A1 | 9/2005 | Taylor |
| 2006/0015183 | A1 | 1/2006 | Gilbert et al. |
| 2006/0116768 | A1 | 6/2006 | Krueger et al. |
| 2006/0129244 | A1 * | 6/2006 | Ensign ...................... 623/17.16 |
| 2006/0206118 | A1 * | 9/2006 | Kim et al. ...................... 606/86 |
| 2006/0217806 | A1 * | 9/2006 | Peterman et al. .......... 623/17.11 |
| 2008/0021555 | A1 | 1/2008 | White et al. |
| 2008/0033563 | A1 | 2/2008 | Khandkar et al. |
| 2008/0140207 | A1 | 6/2008 | Olmos et al. |
| 2009/0099569 | A1 | 4/2009 | Beger |
| 2009/0122049 | A1 | 5/2009 | Miyagawa et al. |
| 2010/0121454 | A1 | 5/2010 | Belliard et al. |
| 2011/0015747 | A1 | 1/2011 | McManus et al. |
| 2013/0253650 | A1 | 9/2013 | Ashley et al. |

OTHER PUBLICATIONS

Medtronic Capstone Peek Spinal System PLIF and TLIF Brochure.
CoRoent XLIG brochure by NuVasive.
Lucent Lumbar InterBody—Setting Our Sights on Simplicity brochure.
AVS PEEK Spacer Portfolio General Systems Overviews—Stryker's PEEK Solution brochure published by Stryker Spine of Allendale, NJ. Copyright 2008.
Surgeon-focused Education—MAS—Maximum Access Surgery by NuVasive, Inc. of San Diego, CA. Copyright 2007.
XLIF Thoracic Surgical Technique brochure by NuVasive, Inc. of San Diego, CA. Copyright 2007.
XLIF Surgical Technique—MaXcess II brochure by NuVasive of San Diego, CA. Copyright 2006.
AVS UniLIF PEEK Spacer System brochure by Stryker Spine, Inc. of Allendale, NJ. Copyright 2010.
VERTE-STACK CRESCENT PEEK Vertebral Body Spacer brochure by Medtronic Spinal and Biologics Business, Memphis, TN. Copyright 2008.
CD Horizon Legacy 5.5, a Masterpiece in Medical Device Design Brochure by Medtronic Sofamor Danek.
AVS TL PEEK Spacer Implant, Stryker Spine, Inc. of Allendale, NJ. Web. <www.stryker.com/en-us/products/Spine/InterbodyVertebralBodyReplacement/AVSTLPEEKSpacerImplant/index.htm> Printed on Mar. 4, 2011.
PCT International Search Report dated Jun. 20, 2011, for the International Application No. PCT/US2010/051984, International Filing Date Oct. 8, 2010.
PCT Written Opinion of the International Searching Authority dated Jun. 20, 2011, for the International Application No. PCT/US2010/051984, International Filing Date Oct. 8, 2010.

* cited by examiner

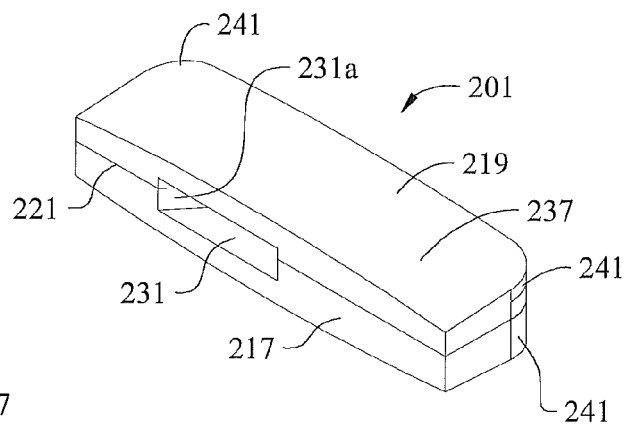
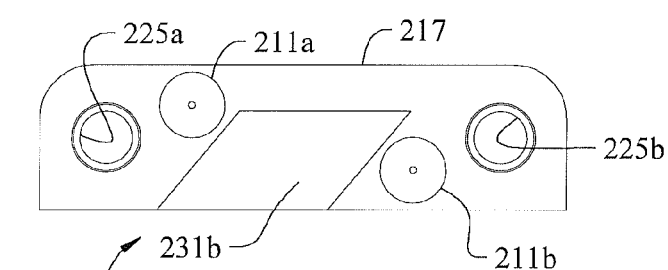
Fig. 42
Fig. 43
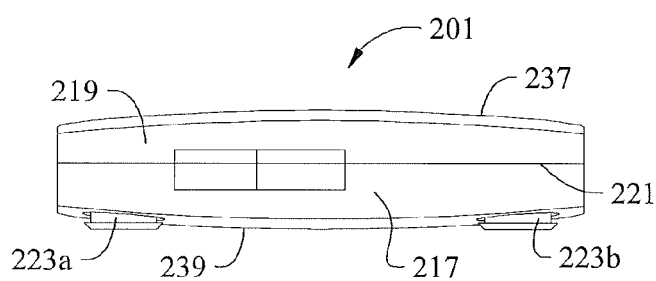 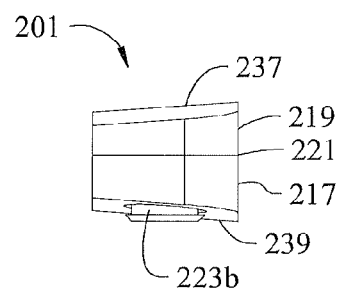
Fig. 44          Fig. 46
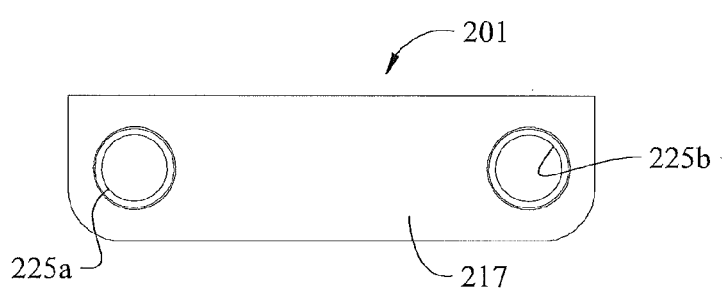
Fig. 45

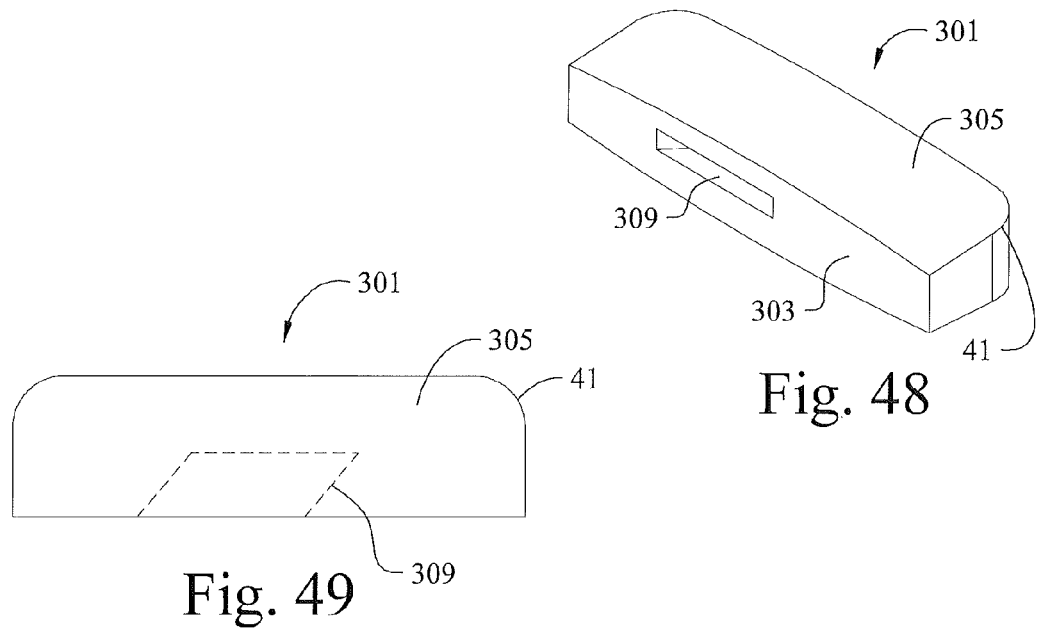
Fig. 48
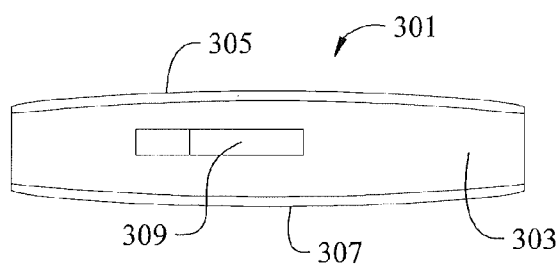
Fig. 49
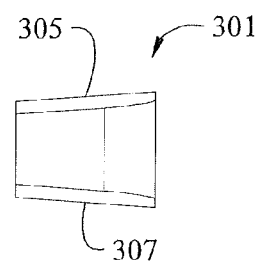
Fig. 50
Fig. 52
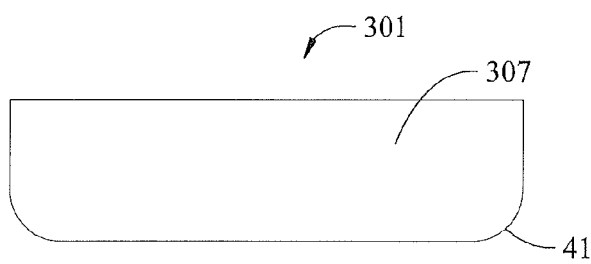
Fig. 51

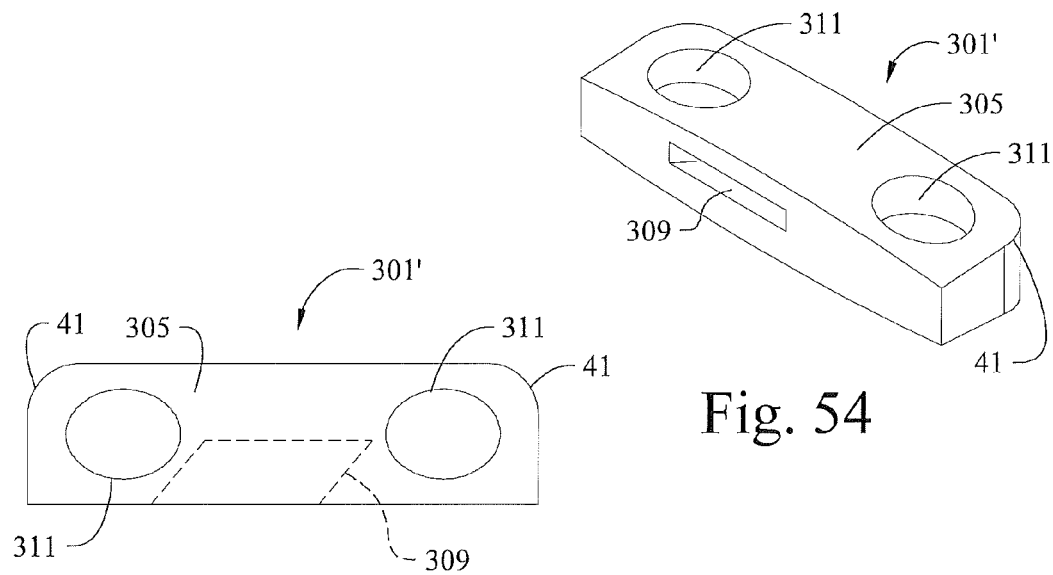
Fig. 54
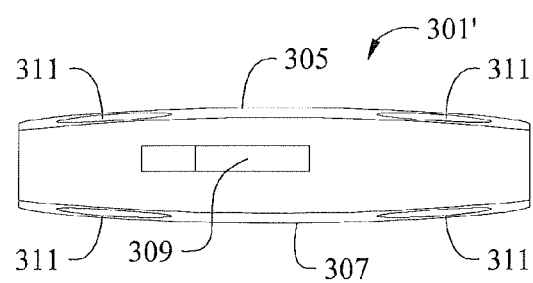
Fig. 55
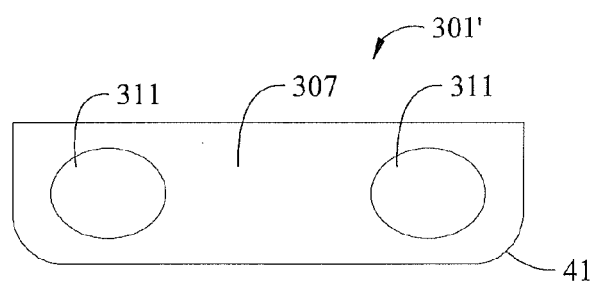
Fig. 56
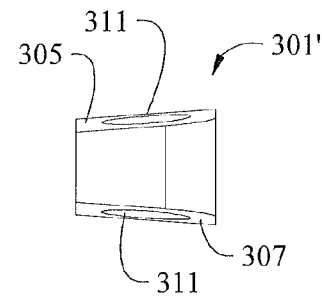
Fig. 58
Fig. 57

EXPANDABLE INTERBODY IMPLANT AND METHOD

CROSS-REFERENCE TO RELATED APPLICATIONS

This application is a continuation application of and claims priority to co-pending application Ser. No. 13/543,126 filed Jul. 6, 2012 which is a continuation-in-part of application Ser. No. 12/899,625 filed Oct. 7, 2010 and continuation-in-part of application Ser. No. 13/030,618 filed Feb. 18, 2011, now U.S. Pat. No. 8,480,748. Application Ser. No. 13/543,126 also claims priority to U.S. Provisional Application No. 61/610, 198 filed Mar. 13, 2012. Application Ser. No. 12/899,625 claims priority to Provisional Application 61/356,851 filed Jun. 21, 2010 and Provisional Application No. 61/251,002 filed Oct. 13, 2009. All of the foregoing prior applications are incorporated herein by reference in their entirety.

STATEMENT REGARDING FEDERALLY SPONSORED RESEARCH OR DEVELOPMENT

Not Applicable.

BACKGROUND OF THE DISCLOSURE

This disclosure relates to intervertebral disc prostheses, and more particularly to an intervertebral disc prosthesis that can be surgically introduced between adjacent vertebral bodies, preferably between lumbar vertebrae, and adjusted or expanded in situ to occupy an optimal or desired space between the vertebral bodies.

In recent years, surgical procedures have been developed in which two or more vertebrae are joined or fused together. Such procedures are now common in the treatment of spinal disorders such as spondylolisthesis, scoliosis, and disc degeneration. Certain of these fusion surgeries include Posterior Lumbar Interbody Fusion (PLIF), Transforaminal Lumbar Interbody Fusion (TLIF), Anterior Lumbar Interbody Fusion (ALIF), and DLIF (Direct Lateral Interbody Fusion). These procedures are well known to spinal surgeons.

Interbody vertebral spacers are known that are inserted between the vertebrae bodies to replace a collapsed, degenerated, or unstable disc. However, these prior spacers were typically of a predetermined thickness and thus it was difficult to size the thickness of the spacer to result in the desired amount of distraction between the vertebrae bodies in order to achieve the desired amount of distraction between the adjacent vertebra bodies. Such prior spacers are commercially available from Stryker Spine of Mahwah, N.J., from Medtronic, Spinal and Biologics Business, Memphis, Tenn., from Spinal Concepts, Inc. of Austin Tex., and from NuVasive, Inc. of San Diego, Calif.

Certain adjustable height interbody fusion devices are known, such as described in U.S. Pat. No. 6,080,193 that vary the distance between the portions of the spacer that engage the endplates of the adjacent vertebrae. However, these adjustable fusion devices rely on cams and other complicated mechanisms for adjustment purposes.

In general, lordosis is the curvature of the spine with the convexity forward. Lordosis is not necessarily a disease state, but rather the normal anterior physiologic curve of the neck or low back. This disclosure is primarily concerned with lumbar lordosis. Most lumbar disc spaces in healthy spines are generally parallel or nearly 0 degree lordotic, and is particularly true for L1/2, L2/3, and L 3/4 However, the L4/5 may have a lordotic angle ranging between about 0°-12°, and L5/S1 may also range between about 0°-12°. Therefore, in reconstructing a disc space that has some lordosis it would be advantageous to have an implant matching the existing anatomy so that the two surfaces of the implant would better conform to and better fit the shape of the disc space so that load sharing occurs over the whole implant. Otherwise, an implant having parallel upper and lower surfaces used in a disc space having, for example, 8 degrees of in situ lordosis would result in only part of the implant contacting its respective vertebrae bodies and thereby lessening the corrective support applied to the spine and thus predisposing the implant to subsidence. That is, subsidence refers to an increased tendency of the implant, over time, to telescope, settle or project into the adjacent vertebrae bodies with loss disc space height back to preoperative levels. When using conventional implants, it is frequently observed that such telescoping or settling occurs with such implants placed wholly within the disc space, rather than having the implant bearing on and distracting from the cortical rim/apophyseal ring of the adjacent vertebrae as disclosed in my co-pending U.S. patent application Ser. No. 12/899, 625. Additionally, a more conformal fit in a disc space with lordosis will allow more uniform distribution of corrective forces applied during distraction. Thus, it would be desirable to provide an expandable (variable height) implant, as described in my above-noted pending application that would provide options for encountered or desired disc space lordosis. It would also be desirable to use either a variable or a fixed height implant that could reconstruct any disc space anatomy or morphology surgically encountered including lordotic conditions with the surgical procedures described in my above-identified U.S. patent applications and in the present disclosure.

SUMMARY OF THE DISCLOSURE

The present disclosure relates to an intervertebral disc prostheses, and more particularly to an intervertebral disc prosthesis that can be surgically introduced between adjacent vertebral bodies, preferably between lumbar vertebrae, and adjusted or expanded in situ to occupy an optimal or desired space between the vertebral bodies. The implant is preferably inserted into the evacuated disc space obliquely and then oriented so as to extend laterally across the adjacent vertebrae bodies anteriorly occupying the disc space with the outer ends of the implant being supported at least in part by the cortical rims on opposite sides of the adjacent vertebrae bodies. The outer convex surfaces of the two body members conform anatomically to the shape of the disc space contacting the endplates. The implant has two body members that are movable relative to one another so as to vary the space between the members. With the implant so positioned and oriented, the implant and thus the disc space may be then distracted and a spacer of a desired, predetermined thickness may be inserted within the space between the body members so as to maintain a desired amount of distraction.

Still further, the present disclosure relates to such an expandable (variable height) or non-expandable (fixed height) disc prosthesis that may have angled upper and lower surfaces engageable with the adjacent vertebrae bodies so as to introduce a predetermined degree of lordosis thereby to better reconstruct the spine by introducing segmental lordosis and improving regional lordosis and global sagittal balance. It is also understood that 0° or parallel surfaced implants maybe an appropriate choice dictated by intraoperative findings and surgical anatomy.

BRIEF DESCRIPTION OF THE DRAWINGS

FIG. 42 is a perspective view of another embodiment of an expandable or variable height implant of the present disclosure (shown without its spacer positioned between the inner faces of its upper and lower body members) having angled (tapered) upper and lower surfaces for treating or correcting certain lordotic conditions;

FIG. 43 is a top plan view of the lower body of the implant shown in FIG. 42;

FIG. 44 is a posterior elevational view of the implant of FIGS. 42 and 43;

FIG. 45 is a bottom plan view of the implant of FIGS. 42-44;

FIG. 46 is a side elevational view of the implant of FIGS. 42-45 illustrating the angled upper and lower faces that constitute a lordosis angle for treating or correcting certain lordotic conditions;

FIG. 48 is a perspective view of still another embodiment of the implant of this disclosure where the implant is a one piece non-expandable implant, but rather is of a fixed height, where such implant has angled or tapered upper and lower surfaces and may be readily utilized in accordance with the methods of this disclosure;

FIG. 49 is a top plan view of the implant of FIG. 48;

FIG. 50 is a front elevational view of the implant of FIGS. 48, 49;

FIG. 51 is a bottom plan view of the implant of FIGS. 48-50;

FIG. 52 is a side elevational view of the implant of FIGS. 48-51 illustrating the lordosis angles of the upper and lower surfaces of the implant;

FIG. 54 is a perspective view of still another non-expandable embodiment of the implant of this disclosure where such implant is fenestrated having openings therein and where such implant may be readily utilized in accordance with the methods of this disclosure;

FIG. 55 is a top plan view of the implant of FIG. 54;

FIG. 56 is a front elevational view of the implant of FIGS. 54, 55;

FIG. 57 is a bottom plan view of the implant of FIGS. 54-57;

FIG. 58 is a side elevational view of the implant of FIGS. 54-57 illustrated the angles upper and lower surfaces of the implant;

Corresponding reference characters indicate corresponding parts throughout the several views of the drawings.

DESCRIPTION OF PREFERRED EMBODIMENTS

Figure 1:
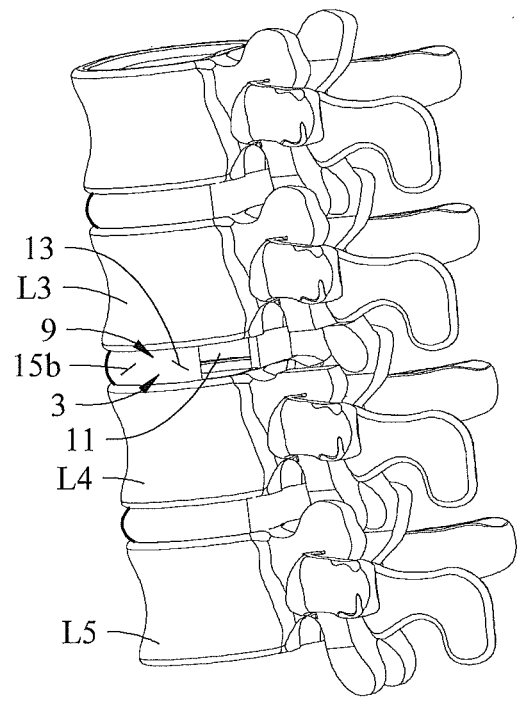
FIG. 1 is a lateral view of a series of lumbar vertebrae (or vertebrae bodies) illustrating intervertebral cartilage discs between adjacent vertebrae, and further illustrating an opening in a posterior lateral quadrant of the annulus for the insertion of an expandable lumbar disc replacement implant or prosthesis of the present disclosure within the disc space between adjacent vertebrae so as to maintain the adjacent vertebrae in a desired distracted position.
Figure 2:
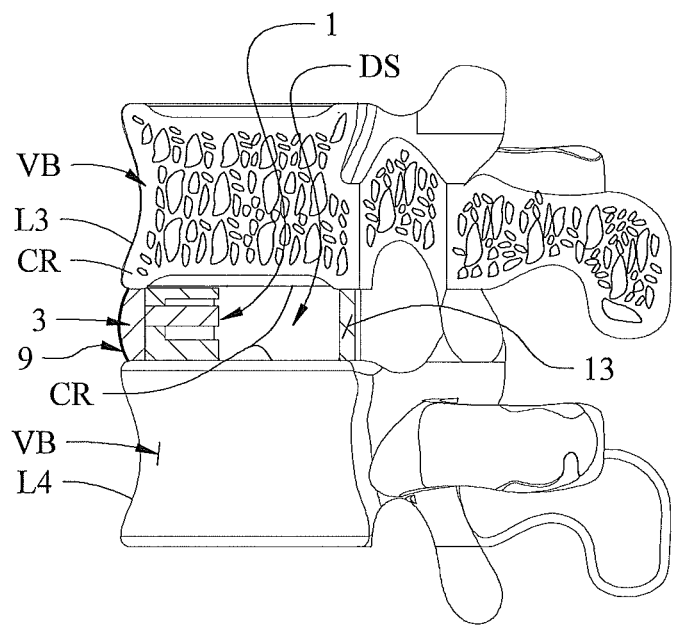
FIG. 2 is a median sagittal cross section of one of two adjacent lumbar vertebrae and the annulus between such adjacent vertebrae illustrating the desired position of the lumbar disc replacement implant within the disc space.
Figure 3:
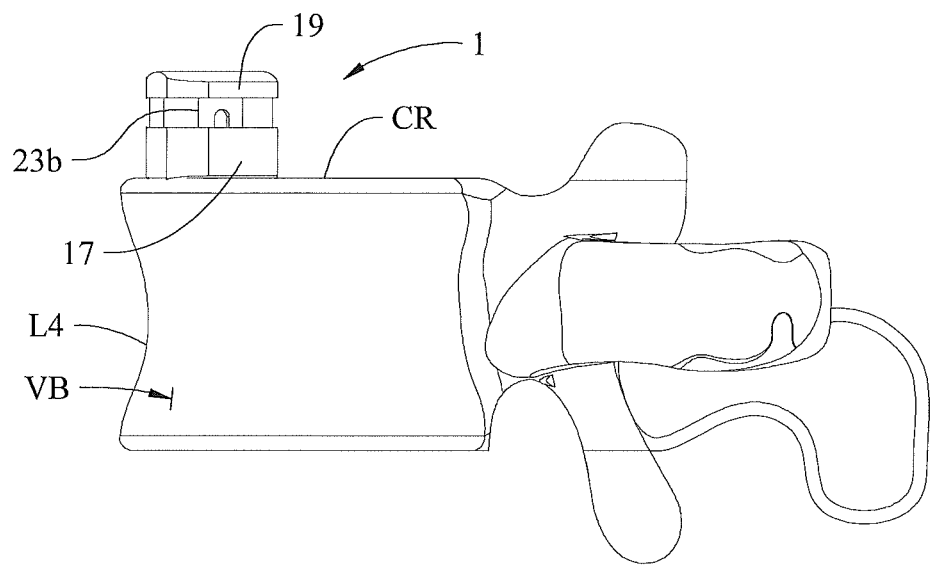
FIG. 3 is a side elevational view of a lumbar vertebrae illustrating the lateral placement of the implant on the upper surface of the cortical rim of the lower vertebrae body.

Referring now to the drawings and particularly to FIGS. 1-4C, a first embodiment of a lumbar disc implant device of the present disclosure is generally indicated at 1 (see FIG. 2), and is shown in its intended environment installed within the disc space DS between two adjacent human vertebrae to be fused together. Oftentimes the intervertebral disc 3 between two adjacent vertebrae (e.g., between lumbar vertebrae L3 and L4, or between lumbar vertebrae L4 and L5) may become degenerated and mechanically incompetent with subsequent loss of height between the adjacent vertebrae with resultant pain and loss of motion. It has become common practice to surgically reconstruct the degenerated disc 3 between the opposing surfaces of the vertebrae bodies and to insert a structural implant within the disc space between the vertebrae so as to space the vertebrae apart a desired distance thus restoring disc space height, and to bear normal biomechanical loads in the spine until a solid spinal fusion occurs. As is conventional, bone graft material (not shown) is introduced into the disc space for fusing the adjacent vertebrae together as the bone graft material grows. Also, such prior disc structural implants are stabilized by known vertebrae fixation devices, such as pedicle screw and rod fixation, which are widely known, but are not shown in the drawings.

Figure 4:
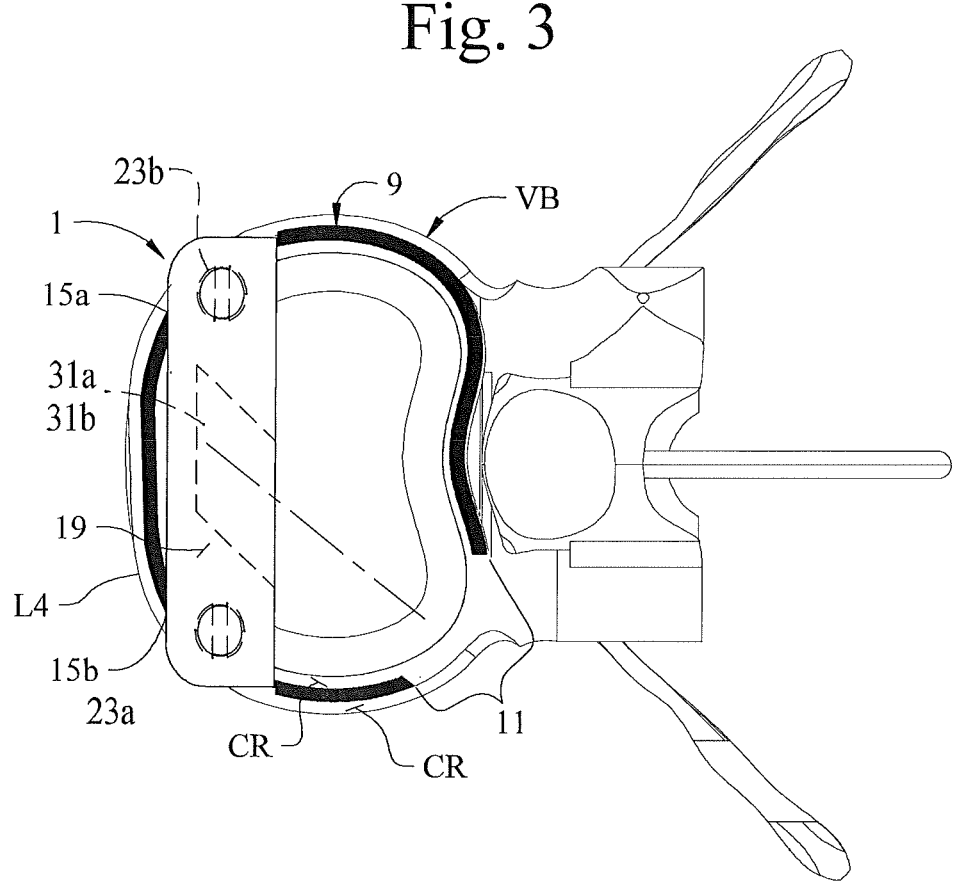
FIG. 4 is an axial inferior view of a lumbar vertebrae (e.g., L4) illustrating the implant of the present disclosure which is initially inserted obliquely through an incision in the annulus and received in a first opening generally opposite the incision and in a second opening generally across from the first opening with the implant oriented to extend across the vertebrae bodies and to span from one side to the other of the vertebrae bodies and to bear against the cortical rims of the upper and lower vertebrae bodies and contacting the interposed endplate, where this view further illustrates an oblique slot in the inner faces of the upper and lower implant body members so as to permit a surgical instrument (e.g., a parallel distractor, such as shown in FIGS. 66-70) to be inserted in these slots to distract the expandable implant and the disc space.
Figure 4A:
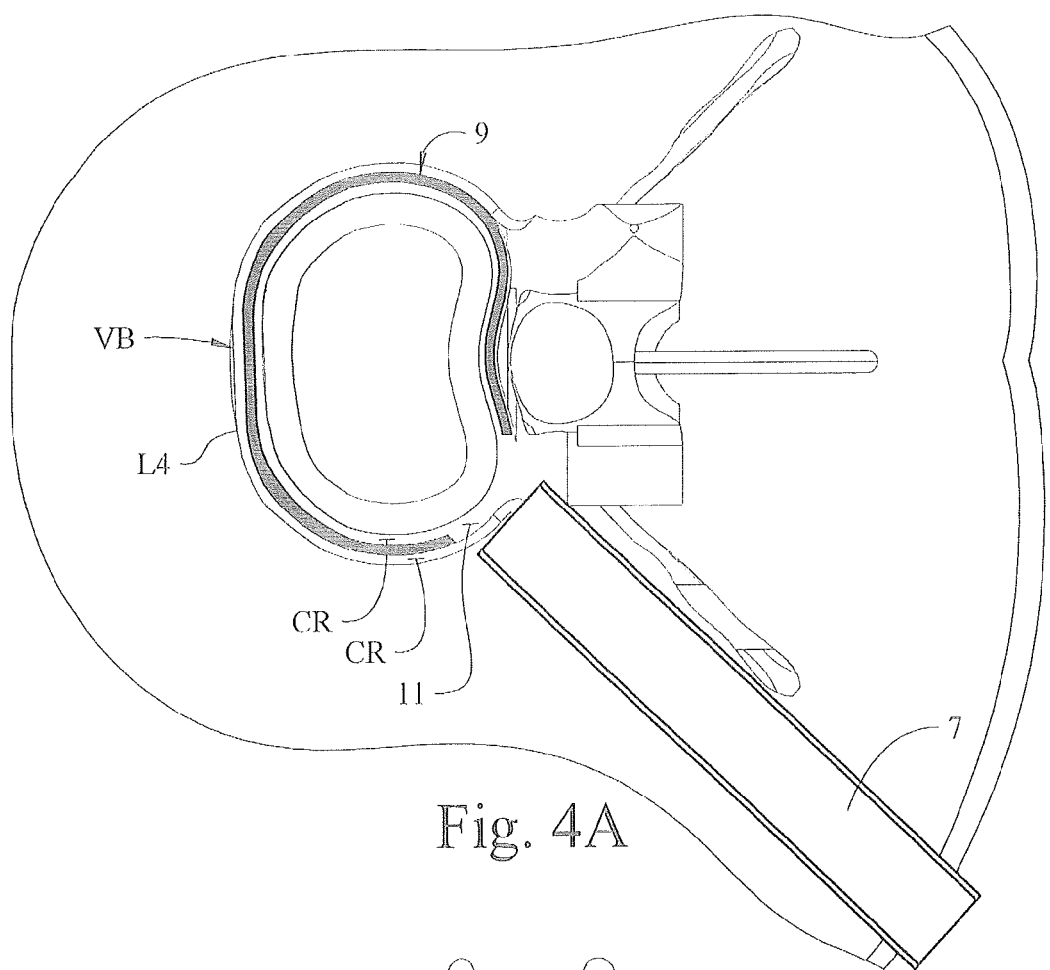
FIG. 4A is a view similar to FIG. 4 of the spine illustrating a minimally invasive TLIF exposure dissecting between the fascial planes of the multifidus and longisimus muscles with an operative tube seated on the bony anatomy of the spine.

As shown in FIG. 4A, an approach is made generally in accord with known transforaminal interbody fusion (TLIF) procedures. Specifically, with the patient in a prone position, fluoroscopy localization is used to place an incision at the desired level. Either an open approach or an approach using a tubular retractor 7, as shown in FIG. 4A, may be used, as is well known in the art. Such a posterolateral TLIF approach is familiar to spine surgeons and does not risk the great vessels and abdominal viscera associated with ALIF (Anterior Lumbar Interbody Fusion) procedures nor does such an approach require an anterior access surgeon. Further, the TLIF approach does not risk injury to the lumbar plexus.

Figure 4B:
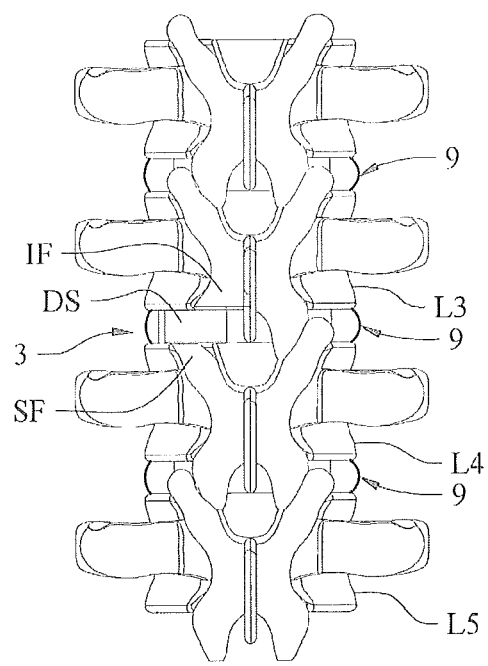
FIG. 4B illustrates lumbar vertebrae L3, L4 and L5 with a unilateral exposure of the operating site between vertebrae L3 and L4.

Further as shown in FIG. 4B, transforaminal access to the disc space DS between the vertebrae is achieved by resection of the inferior facet IF of L3, a portion of the pars interarticularis, and a portion of the superior facet SF of L4. Distraction (i.e., the forcing apart or separation of the vertebrae surfaces) to improve the working corridor may be achieved by using a laminar spreader or pedicle screws, both of which are well-known in the art and which are therefore not shown. Discectomy, a surgical procedure for removal of the disc material from within the annulus 9, is performed through an incision or annulotomy 11, preferably, but not necessarily, a posterior oblique annulotomy, within the operative field (shown in FIGS. 1 and 4C) made in the wall 13 of the annulus 9. Endplate preparation follows using standard procedures and instruments including cupped curettes, ring curettes, box curettes, broaches, box chisels, rasps, and pituitary rongers. All of the disc material between the adjacent vertebrae bodies is removed while the walls 13 of annulus 9 are preserved. The cartilaginous endplates of the vertebrae are removed down to bleeding bone, but care is taken to preserve the cortical endplate, especially anteriorly.

Figure 4C:
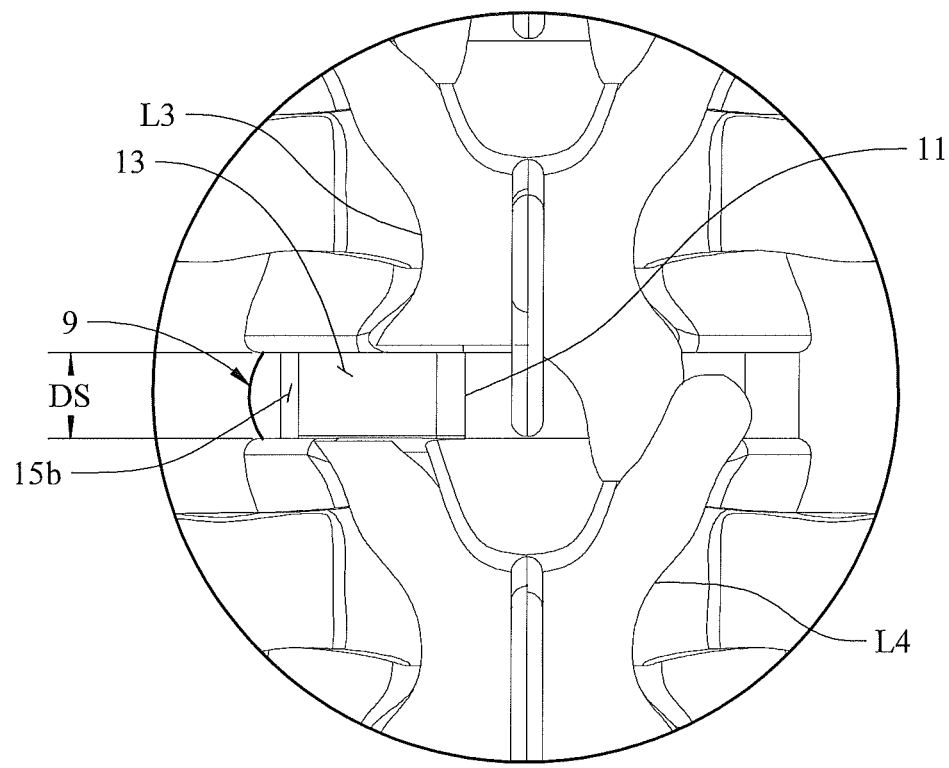
FIG. 4C is a posterior view of the operating site on a somewhat enlarged scale.

More specifically and as shown in FIG. 4C, incision (annulotomy) 11 in annulus 9 permits perforations or openings (also referred to as annulotomies) 15a, 15b, as best shown in FIG. 4, to be made in opposite lateral sides of the anterior annulus such that these openings are generally laterally symmetrical. Those skilled in the art will recognize that a surgeon having access to the interior of the disc space DS via incision 11 will, with proper vision magnification (e.g., a loupe or with endoscopic assistance), be able to make a first opening 15a distal from and opposite incision 11. Then, the surgeon can make the second opening 15b generally across the annulus from the first opening 15a on the opposite anterolateral side of the disc or the annulus (i.e., in the ipsilateral quadrant of the disc relative to incision 11). These annulotomies (including incision 11 and openings 15a, 15b) also serve as anterior and posterior releases to facilitate disc space DS distraction.

More specifically, these anterior annulotomies 15a, 15b may be further relaxed using a variety of techniques including the use of so-called "trials" and distractor instruments, as are well known to those skilled in the art. It is common for surgeons to utilize metal trial implants (not shown) for gaging the size of the actual implant to be used where the trial is at least in part shaped like the implant 1 to be used. Such trials are typically provided in a range of widths, lengths and heights. With the disc space DS at least partially distracted, the surgeon will install a first trial, typically of a smaller size, length, width or height than the implant 1 that will be finally installed, through the anterior annulotomies. These trials are used to aid in distracting the vertebrae and to hold the vertebrae in this desired distracted position. After the ligaments and the annulus at least partially relax, further distraction of the disc space may be accomplished by actuation of a parallel distractor applied to the anterior annulotomies bilaterally. Another trial, typically somewhat larger than the first trial, may be inserted if further relaxation of the anterior annulotomies is required. It will be understood that the trials can be used to judge the width and height of the size of the actual implant 1 to be employed. Then, with the disc space DS prepared, the implant 1 of the proper height, length, and width will be installed, preferably in the manner discussed below.

Figure 4D:
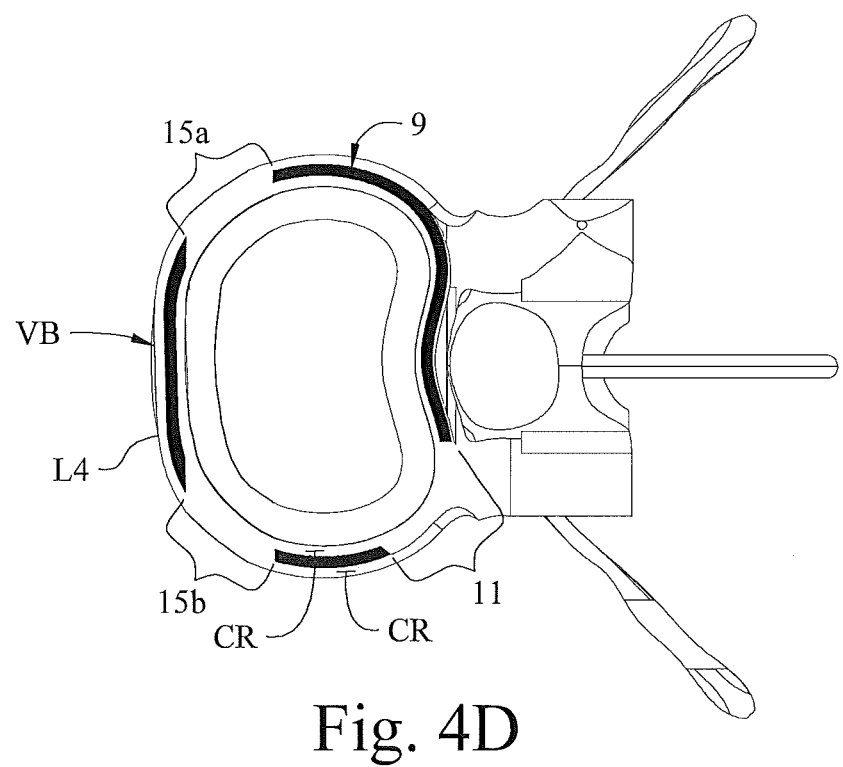
FIG. 4D is a view similar to FIG. 4 illustrating the incision and the first and second openings in the annulus without the implant of this disclosure installed.

FIG. 4D is a view similar to FIG. 4, but where the implant 1 has been removed from the disc space DS so as to better show the incision 11, the first opening 15a, and the second opening 15b, as they may be formed in annulus 9.

Figure 4E:
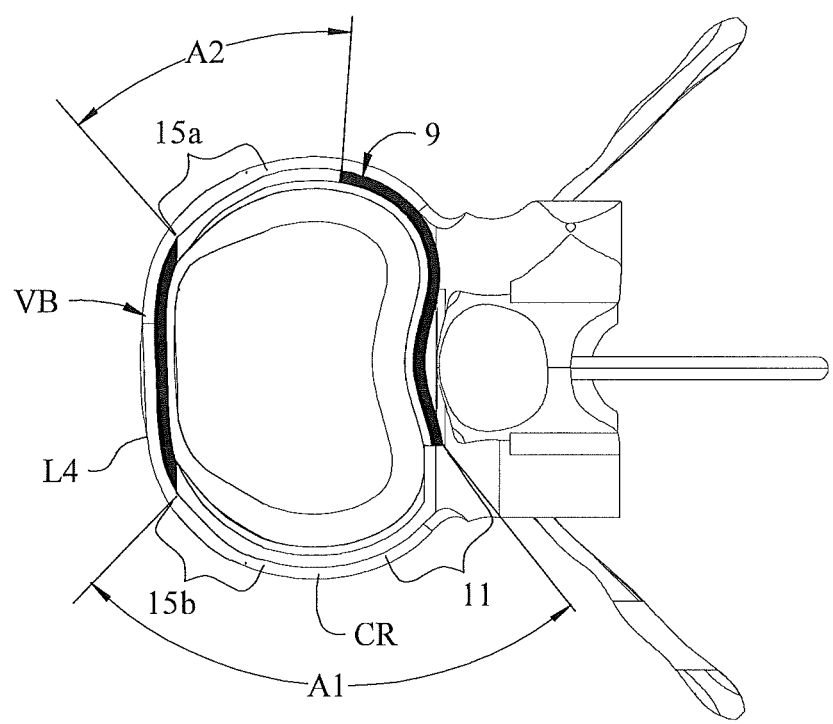
FIG. 4E is a view similar to FIG. 4D, but where the incision and the second opening are, respectively, posterior and anterior portions of a single elongate annulotomy and where the first opening is the anterior portion of another elongate annulotomy, where the elongate annulotomies help relax the annulus.

FIG. 4E is a view similar to FIG. 4D, but where one elongate incision, as indicated at A1, is made in annulus 9, where the posterior portion of the elongate incision incorporates incision 11 and where the anterior portion of the elongate incision incorporates the second opening 15b. Still further, the first opening 15a is incorporated in an elongate incision A2. These elongate incisions A1 and A2 help relax the annulus. As will be particularly described below in regard to FIGS. 4M-4O, the elongate incision A1 allows for the insertion of endoscopic and surgical instruments so that the surgeon may perform the discectomy of the disc space DS under endoscopic viewing.

Figure 4F:
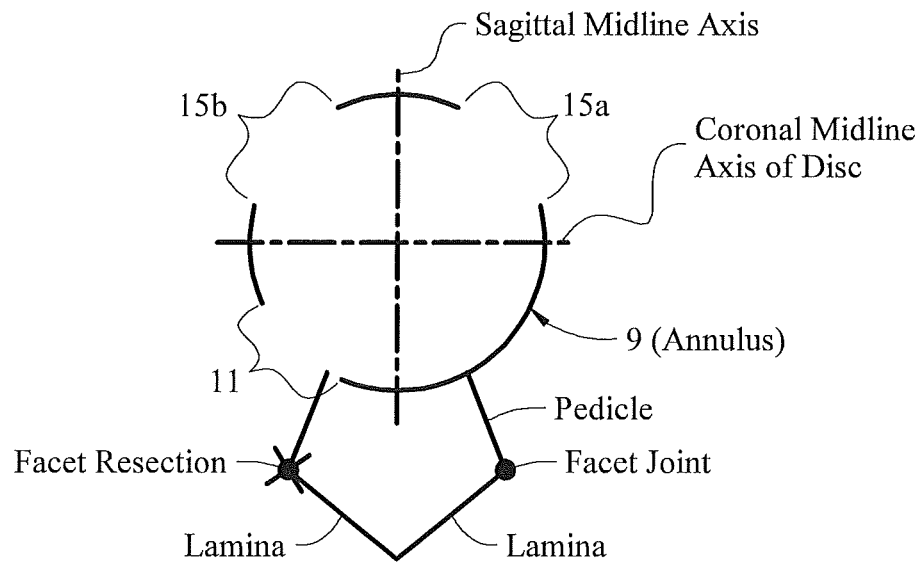
FIG. 4F is a diagrammatic axial depiction of a vertebrae (or vertebrae body), the annulus, the disc space, and other major anatomical features of the vertebrae illustrating the location of the incision and the openings made in the annulus in accordance with the procedure shown in FIGS. 4 and 4D.
Figure 4G:
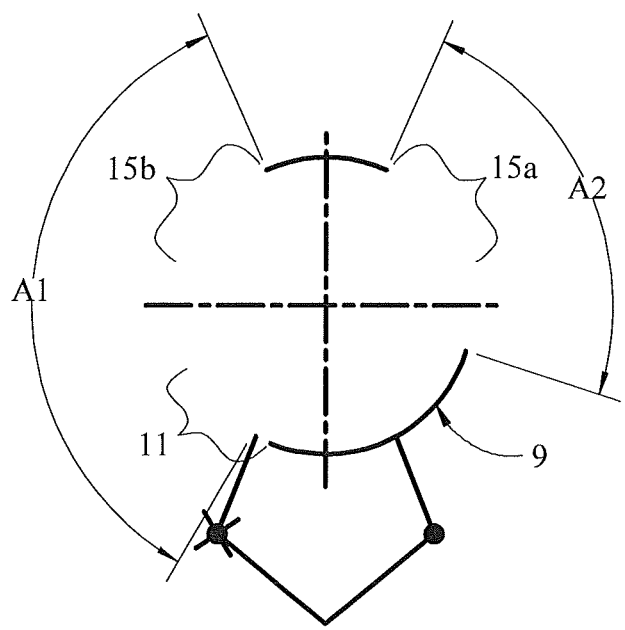
FIG. 4G is a view similar to FIG. 4F illustrating the location of the openings made in the annulus in accordance with the procedure of this disclosure, as shown in FIG. 4E, such that there is sufficient room to insert an endoscopic light delivery system and lens viewing system and also to accommodate surgical instruments for performing endoscopic discectomy.

FIG. 4F is a diagrammatic axial illustration of the vertebrae and the annulus 9 showing the Sagittal Midline Axis, the Coronal Midline Axis of the Disc, and other prominent anatomical features of the vertebrae and the approximate location of incision 11 and openings 15a and 15b illustrated in FIGS. 4 and 4D. Alternatively, as shown in FIGS. 4E and 4G, the incision 11 and the second opening 15b may be formed by a single elongate annulotomy A1 where the incision 11 is a posterior portion of the elongate annulotomy A1 and where the second opening 15b is the anterior portion of the elongate annulotomy A1, and where the first opening 15a may be the anterior portion of another elongate annulotomy A2 on the opposite side of the annulus 9. These elongate annulotomies A1 and A2 relax the annulus and release the disc space to better facilitate the distraction of the adjacent vertebrae. It will be appreciated that the elongate annulotomies A1 and/or A2 serve to maximize the release of the disc space DS and the relaxation of annulus 9 to facilitate distraction. Still further, the elongate annulotomies A1 and/or A2 facilitate discectomy and/or end plate preparation by allowing the surgeon to have a larger field of view of the disc space, either with increased magnification (e.g., a loupe) or with endoscopic assistance (as shown in FIGS. 4M-4O). It will be appreciated that the elongate annulotomies A1 and A3 afford increased room for the insertion of surgical instruments SI (either manual or powered instruments), as shown in FIG. 4N, for performing surgical procedures within the disc space DS, such as discectomy and end plate preparation, and for enhancing the surgeon's field of view of the disc space. Examples of manual surgical instruments may include, but may not be limited to, the above described cupped curettes, ring curettes, broaches, box chisels, rasps, and pituitary rongers. Further, the elongate annulotomy A1 allows an endoscopic light delivery system to illuminate the disc space and an endoscopic lens system to transmit the image to be viewed by the surgeon. Endoscopic apparatus, such as indicated at 801 in FIGS. 4M-4O, which is described in detail below, may be used. An advantage to being able to perform the discectomy and/or endplate preparation under endoscopic viewing is that power tools, such as the Midas Rex Spine Shaver Nucleus Removal Set, commercially available from Medtronic, Inc. of Minneapolis, Minn., may be used because the surgeon now has the ability to see and to better control the use of such instruments.

As shown in FIGS. 4, 4D, and 4F, the incision 11 is formed in the posterior lateral quadrant of the disc space DS in the position generally as shown in FIG. 4F. Further, the first opening 15a is formed in the annulus 9 in the generally opposite anterior lateral quadrant of the disc space and the second opening 15b is formed in the contralateral anterior quadrant (i.e., on the same side as incision as 11 or in the ipsilateral anterior lateral quadrant relative to incision 11). It will be understood that if it is desired that the approach be from the contralateral side, the openings would be reversed from their position as shown in FIG. 4. Also, the direction of the slots 31a, 31b in the implant will be reversed.

More specifically, it will be understood by those of ordinary skill in the art that the incision 11 and the openings 15a, 15b may be the mirror image of their locations shown in FIG. 4F, and that the elongate openings or incisions A1 and A2 may be the mirror image of their locations shown in FIG. 4G. It will also be understood by one skilled in the art that the location and the length of the incisions or openings 11, 15a, 15b, A1 and A2, as shown in FIGS. 4F and 4G, are only the approximate locations of these incisions or openings in the annulus 9 and that a surgeon using the implants and methods of this disclosure may vary, at the surgeon's discretion, alter the locations and lengths of these incisions and openings to fit the anatomical features of the particular patient undergoing the operation. It will also be understood that even if the elongate incisions A1 and A2 are not employed, the incision 11 and the openings 15a, 15b may be considerably longer than is shown in FIGS. 4D and 4F.

Figure 4H:
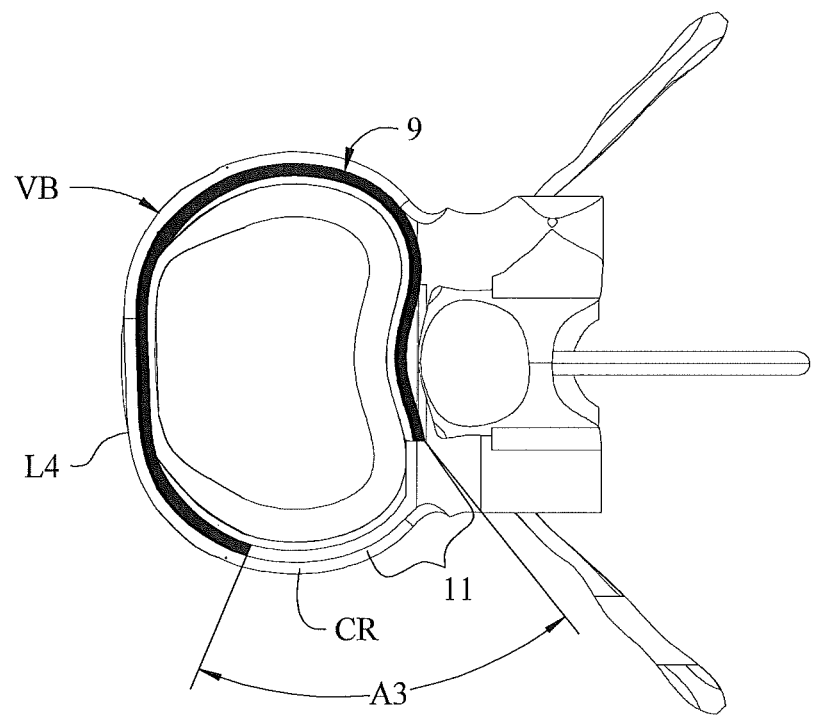
FIG. 4H is a view if a vertebrae and the annulus illustrating an annulotomy in the annulus in a posterior lateral quadrant of the annulus which is somewhat shorter than the elongate incision shown in FIG. 4G such that the annulus is relaxed and such that there is sufficient room to insert an endoscopic light delivery system and lens viewing system and also to accommodate surgical instruments for performing endoscopic discectomy.
Figure 4I:
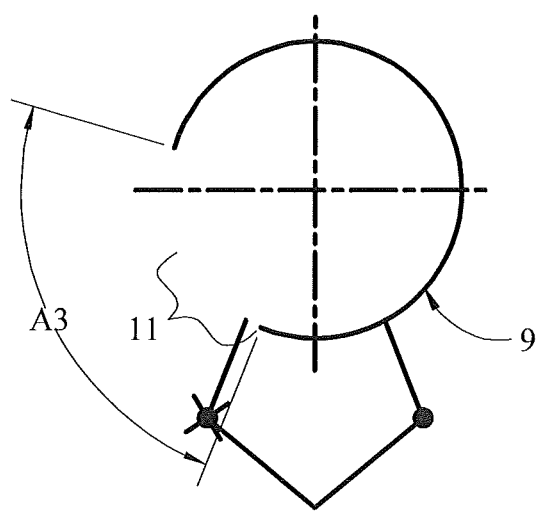
FIG. 4I is a diagrammatic view similar to FIG. 4F illustrating the elongate incision of FIG. 4H.

Referring now to FIGS. 4H-K and FIGS. N-O, it will be noted in FIG. 4H that the incision A3 in the posterior lateral quadrant is considerably longer than incision 11 and that includes incision 11. It has been found that such a longer incision relaxes the annulus thereby facilitating discectomy and distraction of the disc space DS. This longer incision A3 is diagrammatically illustrated in FIG. 4I.

Figure 4J:
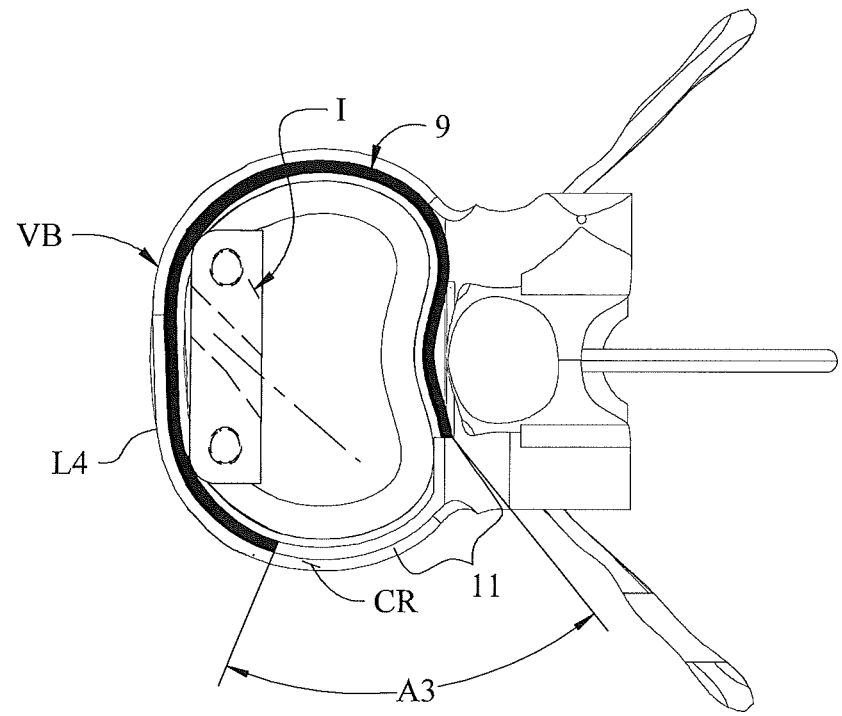
FIG. 4J is a view similar to FIG. 4H illustrating an implant of the present disclosure installed within the disc space, but where the implant is somewhat shorter than the implant shown in FIG. 4, where this implant does not bear on the cortical rim, but is supported by the endplates of the vertebra bodies.

As shown in FIG. 4J, after discectomy of the disc space DS, an implant, as generally indicated in its entirety at I made in accordance with any of the embodiments disclosed herein or any other conventional implant may be inserted into the anterior region of the disc space, where the implant is supported on the end plates of the vertebra. This implant I maintains distraction of the disc space while bone growth or bone graft material (not shown) is packed into the remaining area of the disc space fuses the vertebra.

Figure 4K:
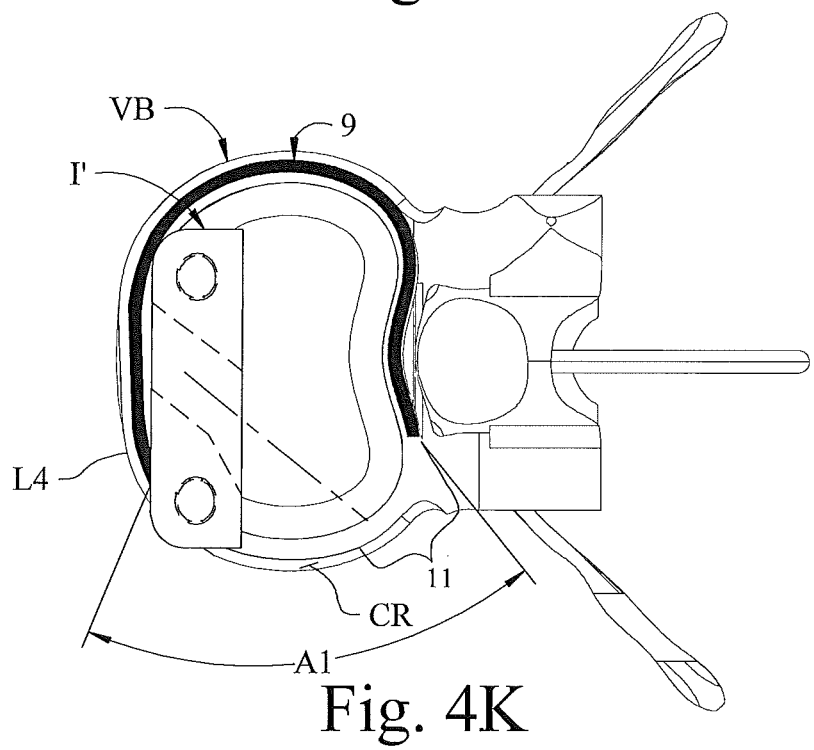
FIG. 4K is a view similar to FIG. 4J, where the implant is somewhat longer than the implant of FIG. 4J and where one end of the implant partially extends through the elongate incision and bears at least in part on the cortical rim.

As shown in FIG. 4K, an implant I' may be somewhat longer than implant I shown in FIG. 4J where one end of the implant I' may partially extend through the anterior portion of incision A3 so that this one end of the implant is supported on the cortical rim CR. Again, implant I' may be any of the embodiments of the implants disclosed herein or any other conventional implants.

Figure 4L:
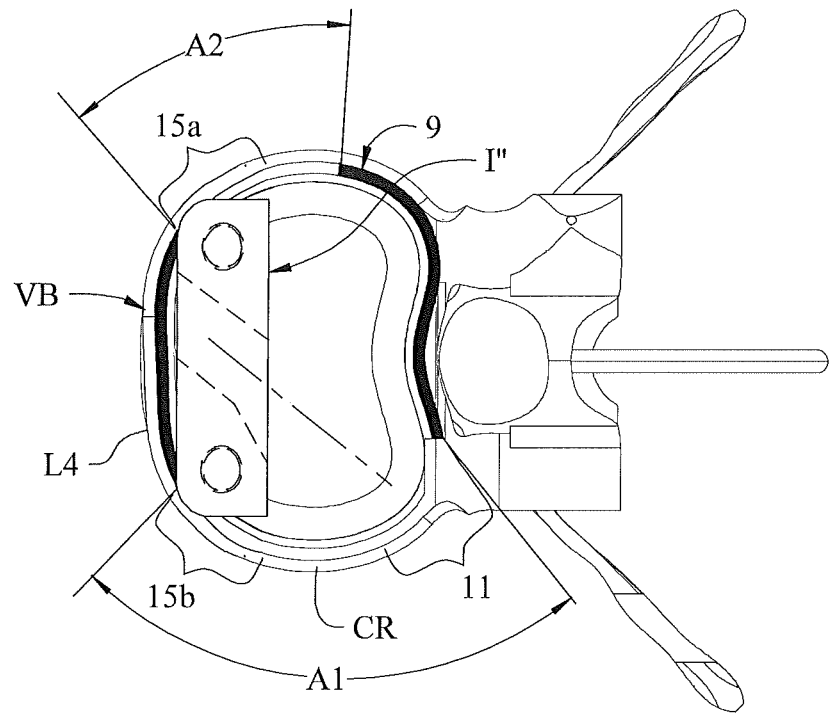
FIG. 4L is a view similar to FIG. 4E with an implant in accordance with the present disclosure extending across the anterior portion of the disc space and bearing on the cortical rim of the vertebrae bodies.
Figure 4M:
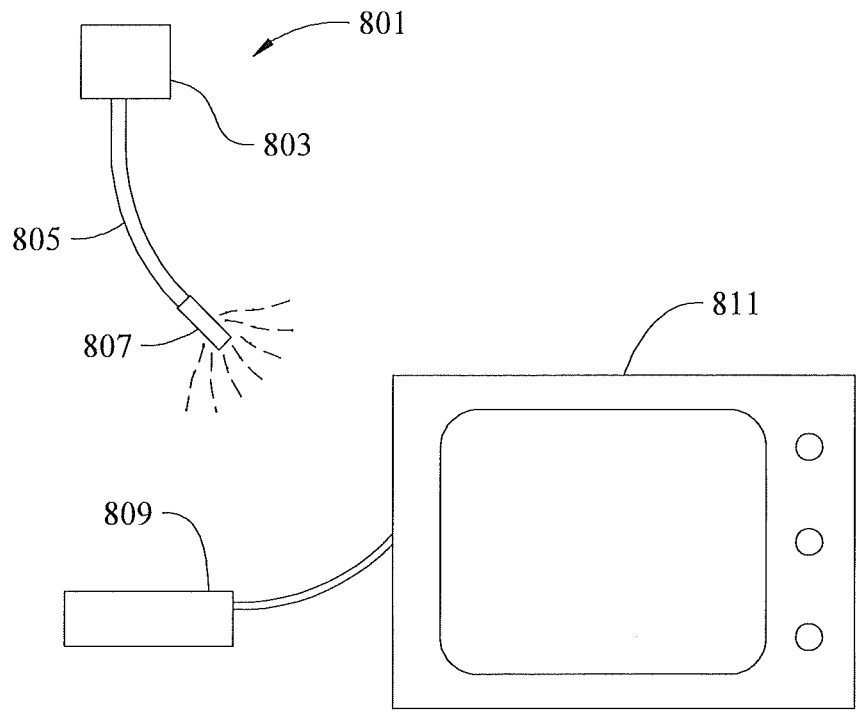
FIG. 4M illustrates a typical endoscopic system that may be used in conjunction with the present disclosure where an endoscopic camera and light source may be inserted into the disc space through an elongate incision in the annulus so as to enable the surgeon to perform discectomy of the disc space with endoscopic viewing.
Figure 4N:
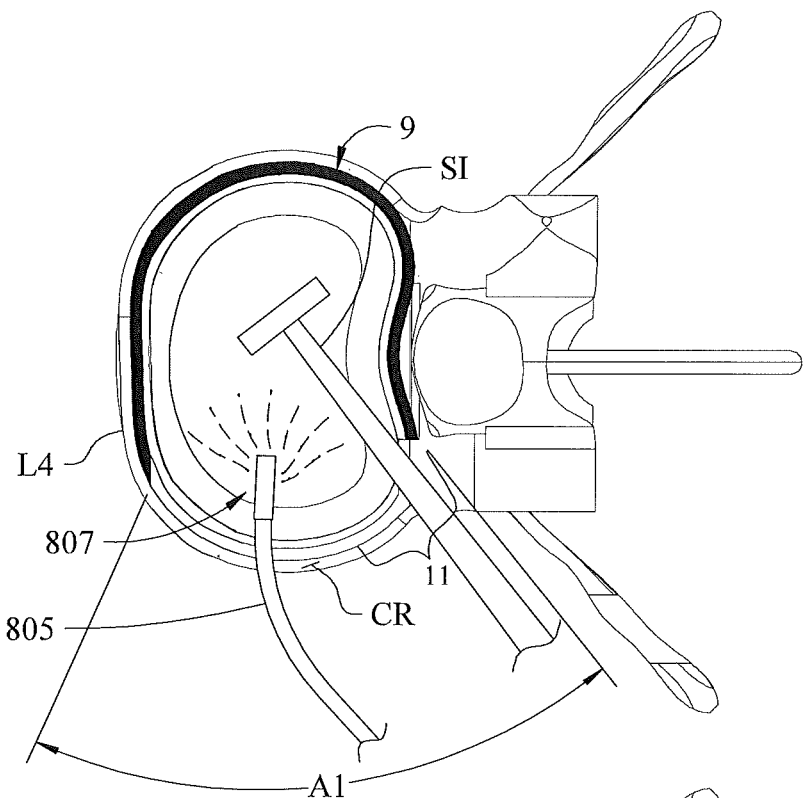
FIG. 4N is a view similar to FIG. 4M illustrating the insertion of endoscopic apparatus and surgical instruments into the disc space.
Figure 4O:
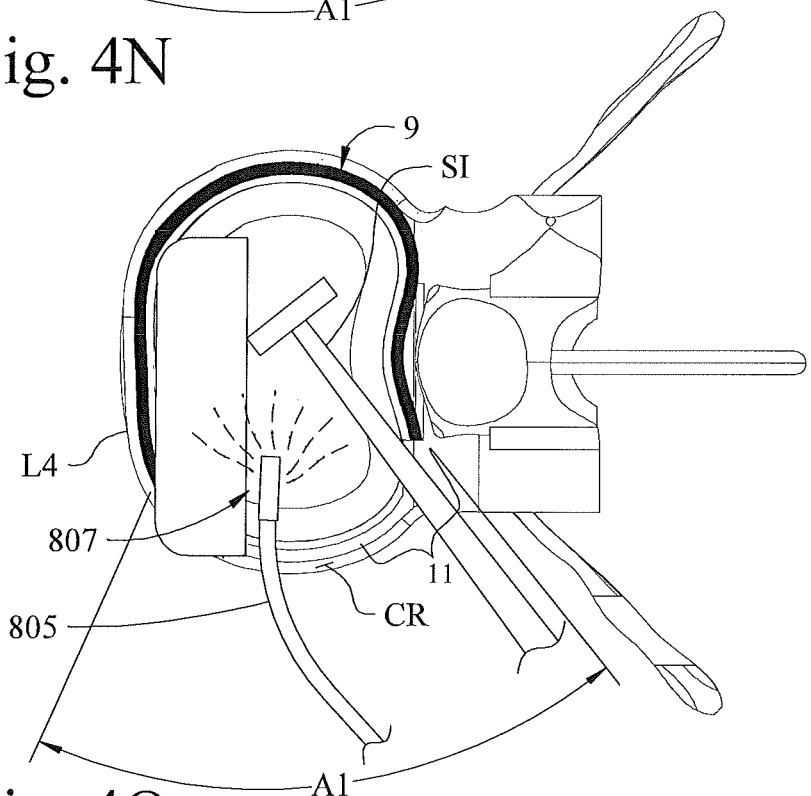
FIG. 4O is a view similar to FIG. 4K illustrating the placement of the implant across the anterior of the disc space and illustrating the insertion of endoscopic and surgical instruments into the disc space.

FIG. 4L is similar to FIGS. 4E and 4G having elongate incisions or annulotomies A1 and A2 in annulus 9 with an implant I" installed within disc space DS extending across the anterior region of the vertebrae bodies VB where the ends of the implant I" are supported on the cortical rims CR of the vertebrae bodies. Implant I" may be any of the embodiments of the implants disclosed herein or any other conventional implants.

FIG. 4M illustrates endoscopic surgical apparatus 801 that may be employed to aid the surgeon in performing the discectomy of the disc space DS thus giving the surgeon the ability to view the disc space while the discectomy is being performed. Heretofore, the surgeon performed the discectomy "blind" and was not able to see into the disc space. In accordance with the present disclosure there is an advantage of performing the discectomy under endoscopic viewing because the surgeon can typically perform the discectomy faster and can visually insure that the discectomy is properly performed such that little or no debris remains in the disc space after discectomy, where such debris may interfere with the growth of the bone growth material packed into the disc space and with the fusing of the vertebra.

As is conventional, such endoscopic surgical apparatus 801 includes a housing 803 and a fiber optic light transmitting tube 805 that transmits light from 803 to a lens in the distal end of the tube to illuminate the disc space. Additionally, the end of the tube 805 includes a wide angle lens 807 which transmits an image of the disc space via tube 805 to a wireless transmitter in housing 803 to a wireless receiver base station 809, which in turn displays the image on a monitor 811 to be viewed by the surgeon performing the discectomy. It will be appreciated that, as is conventional, the surgeon may grip housing 803 to maneuver the distal end of the light tube 805 in the disc space so as to allow the surgeon to view different areas of the disc space. It is also appreciated that in lieu of wireless coupling of fiber optic endoscope to monitor cables maybe used.

As shown in FIG. 4N, the elongate incision A3 provides ample room for the insertion of the endoscopic tube 805 and the lens 807 so that the surgeon may operate surgical instruments SI (either manual or powered) to perform the discectomy under endoscopic viewing.

FIG. 4O shows that there is ample room within the disc space DS with the elongate incision A3. It will be appreciated that initial endplate preparation may be carried out prior to distraction. However, after the disc space has been distracted and after the implant is in place between the adjacent vertebrae bodies VB, a surgeon may prefer to complete endplate preparation under endoscopic viewing so as to result in better preparation.

Implants 1 are available in a series of various predetermined lengths, widths and heights to best fit particular patients. For example, the length of a typical implant 1 may be about 50 mm and about 8.5 mm tall. Calipers or trials (not shown) are used to measure and size the anterior disc space and to determine the length of the implant 1 to be used. Intraoperative fluoroscopy will aid in these measurements.

With the desired final height, width and length of the implant 1 determined, and with the implant in its collapsed or retracted position (for example, with spacer 35 removed from between the body members 17 and 19 and with the inner faces of the body members in contact with one another), the implant is inserted into the disc space DS via incision 11 at an oblique angle using the implant applicator (not shown) or other suitable instrument. The implant applicator grasps the implant firmly allowing controlled insertion and positioning of the distal end of the implant thru the contralateral anterior annulotomy 15a. The insertion of the implant is also disclosed in conjunction with the distractor 601, as described hereinafter. Once the proximal end of the implant is within the disc space DS, the applicator is removed. The parallel distractor may be used to maneuver implant into final position with both ends protruding through anterior annulotomies 15a, 15b, generally as shown in FIG. 4.

In this manner, the implant bears against and is supported at least in part by the cortical rim CR of both the upper and lower vertebrae. Fluoroscopic confirmation (as hereinafter described) of optimal positioning utilizing radiographic markers, as indicated at 43 in FIGS. 5 and 6, embedded in the implant is carried out. After the implant 1 has been so oriented and positioned within the disc space DS, the blades of a parallel distractor (not shown in FIG. 4, but which distractor may be similar to the distractor 601 hereinafter described) are inserted into the disc space via incision 11 in the annulus 9. The disc space and the implant are then further distracted and a spacer, as indicated at 35 and as shown below, is installed within the implant in a manner as will appear. Upon removal of the parallel distractor and upon applying compression to the construct, the implant bodies 17, 19 and the spacer 35 will maintain the implant 1 in its desired height.

Figure 5:
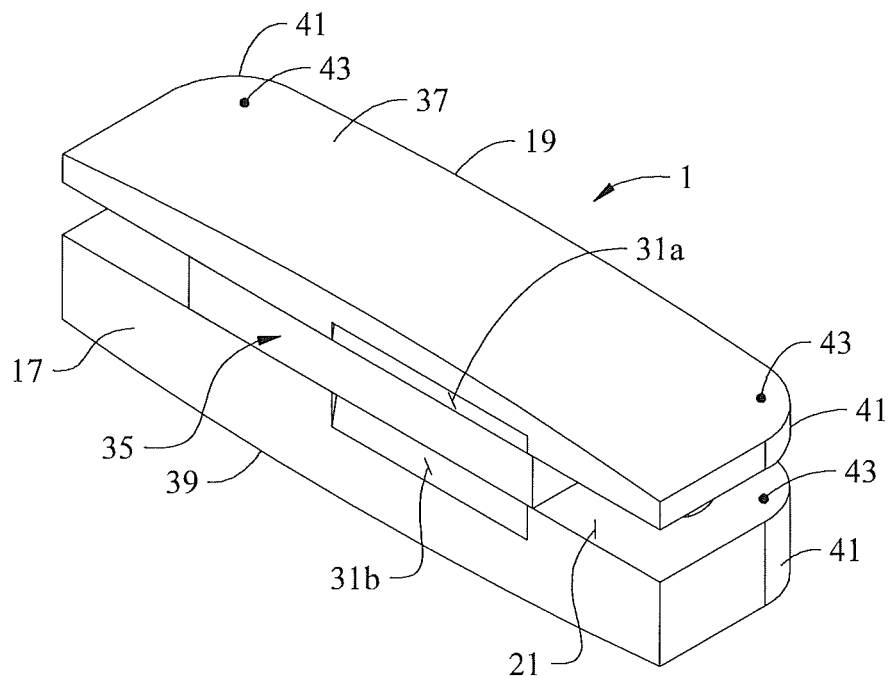
FIG. 5 is a posterior perspective view on an enlarged scale of the implant of the present disclosure, as viewed from above, having an upper and a lower body member with a space between the inner faces of these upper and lower body members and with a spacer of predetermined thickness inserted within the space between the body members so that when the disc space is retracted, the body members and the spacer maintain a desired distraction between the adjacent vertebrae bodies and bear normal spinal biomechanical loads until solid spinal fusion is achieved.

Referring now to FIGS. 5-17, the implant 1 of the present disclosure will now be described in detail. As shown in FIG. 5, implant 1 has a pair of separate body members 17 and 19, with body member 17 being referred to as a lower body member and with body member 19 being referred to as an upper body member with a space 21 therebetween. It will be appreciated that with the inner faces of the body members touching one another the space 21 is minimized and the overall height of the implant is minimized. With implant 1 in this position, it has a low profile that facilitates insertion and final positioning within disc space DS. Further, with the body members 17 and 19 spaced apart a maximum distance, the implant is in its fully distracted position. The height of implant 1 thus may be expanded in situ a desired amount to enable distraction of the degenerated disc 3 to normal anatomic height with appropriate tensioning of the annulus 9 and stabilizing ligaments.

Figure 13:
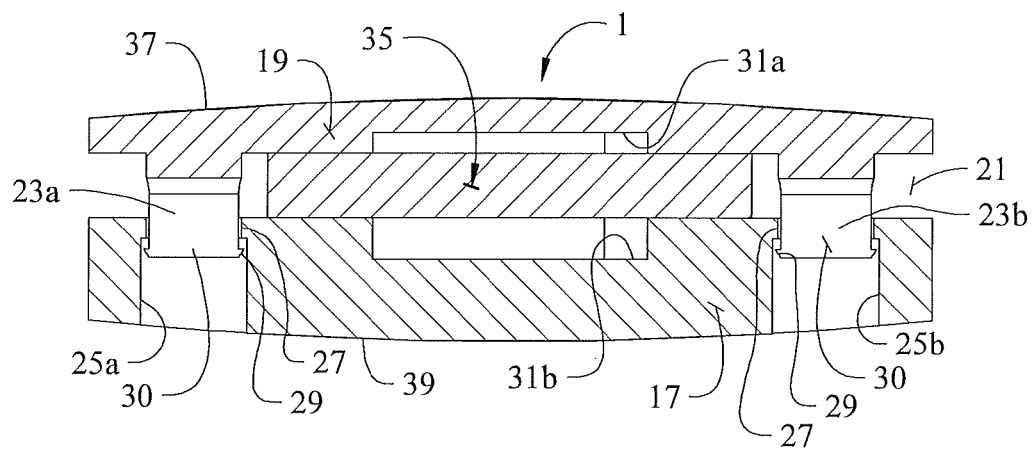
FIG. 13 is a lengthwise vertical cross sectional view taken along line 13-13 of FIG. 12.
Figure 14:
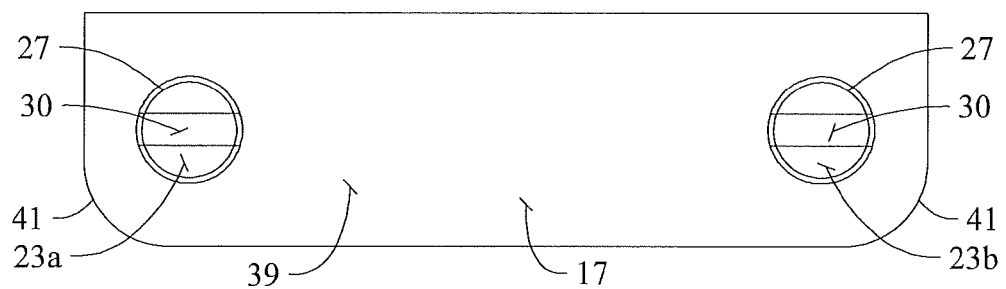
FIG. 14 is a bottom plan view of the implant.
Figure 15:
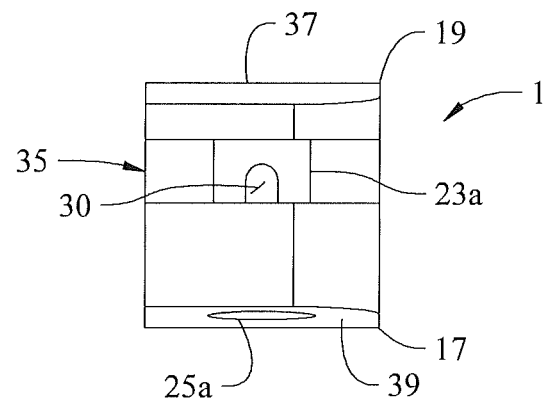
FIG. 15 is a right side elevational view of the implant as shown in FIG. 12.
Figure 16:
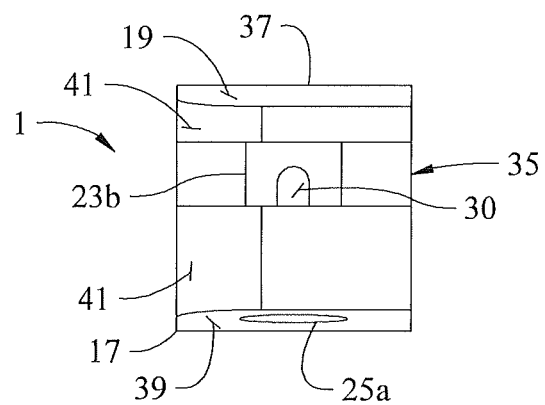
FIG. 16 is a left side elevational view of the implant as shown in FIG. 12.
Figure 17:
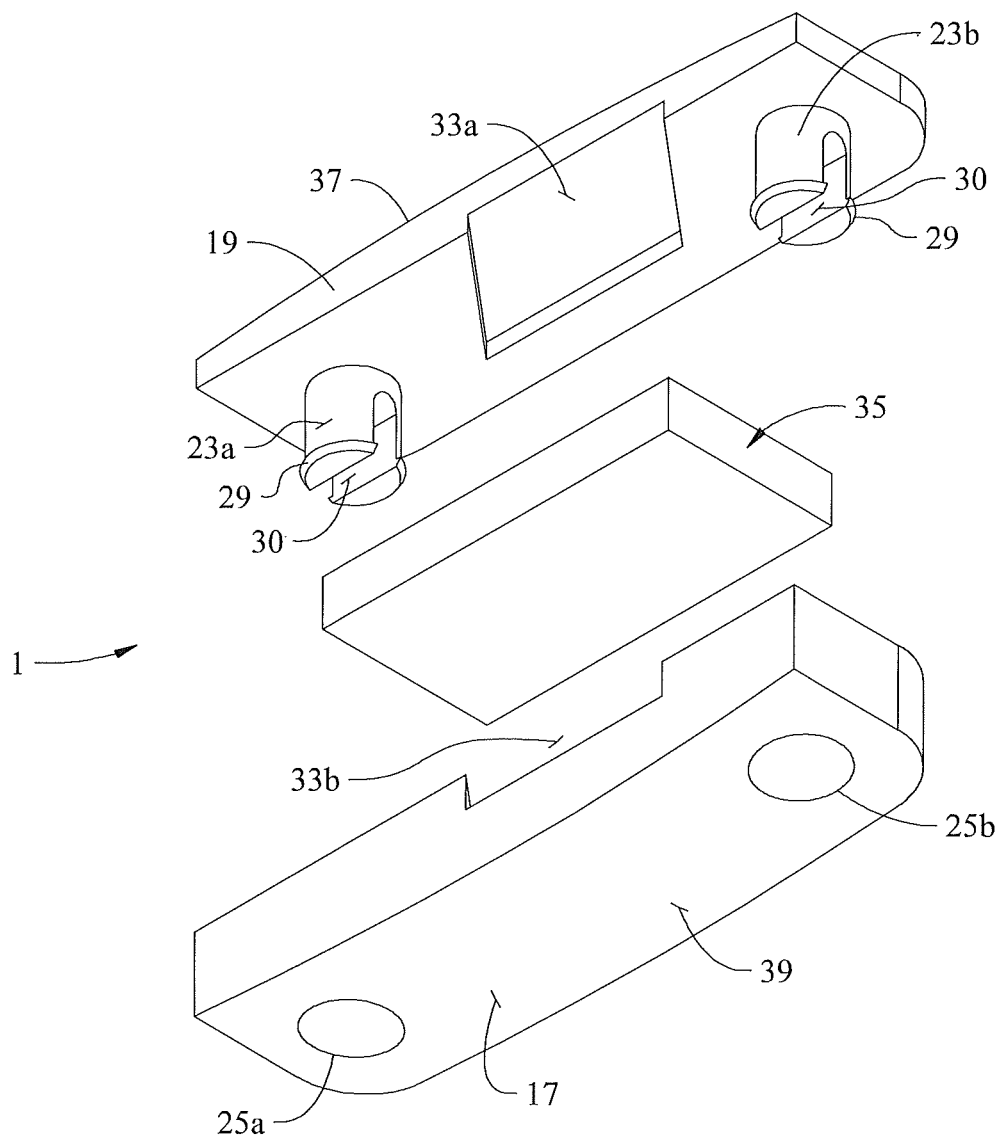
FIG. 17 is a bottom perspective exploded view of the implant.

As best shown in FIG. 13, the upper member 19 has a pair of spaced stabilizing posts 23a, 23b extending down into space 21. These stabilizing posts 23a, 23b are each received in a respective bore 25a, 25b in the lower member 17. As indicated at 27, each bore 25a, 25b has an inwardly extending flange of somewhat smaller diameter than the remainder of the bore, with the diameter of the flange 27 being only somewhat larger than the diameter of the stabilizing posts 23a, 23b. Further, at the distal end of each of the stabilizing posts, an enlarged head 29 is provided with the head being somewhat larger than the diameter of the post and being somewhat larger than the bore in flange 27. In this manner, with the posts received in their respective bores, the heads 29 on the end of each post cooperates with flange 27 so as to prevent the body members 19 and 21 from becoming distracted (moved apart) more than a predetermined distance. As best shown in FIG. 17, each of the stabilizing posts 23a, 23b may have an optional longitudinal slot 30 which enables the post to be somewhat resiliently compressed so that the flanges 29 on the ends of the posts may be inserted through the bores thus allowing the posts to be received in their respective bores 25a, 25b. Once the posts have been inserted in the bores, the posts will spring back to resume their shape and size prior to being compressed. It will be further understood that the bodies of posts 23a, 23b preferably have a sliding close fit within the bores of their respective flanges 27 such that the posts stabilize the upper and lower body members relative to one another so as to resist the body members from twisting, shearing, or tipping relative to one another in all directions. These stabilizing posts help maintain the body members 17 and 19 oriented in a desired parallel relation to one another as the implant 1 is inserted within the disc space DS and distracted, in the manner as will be hereinafter described. Further, the provision of flanges 27 and 29 provide a tactile feel that prevents over distraction of the body members 17 and 19. While the above-described stabilizing posts 23a, 23b have been described as having slots 30 therein, it will be understood that the slots may be omitted and that the posts may be solid members.

Figure 18:
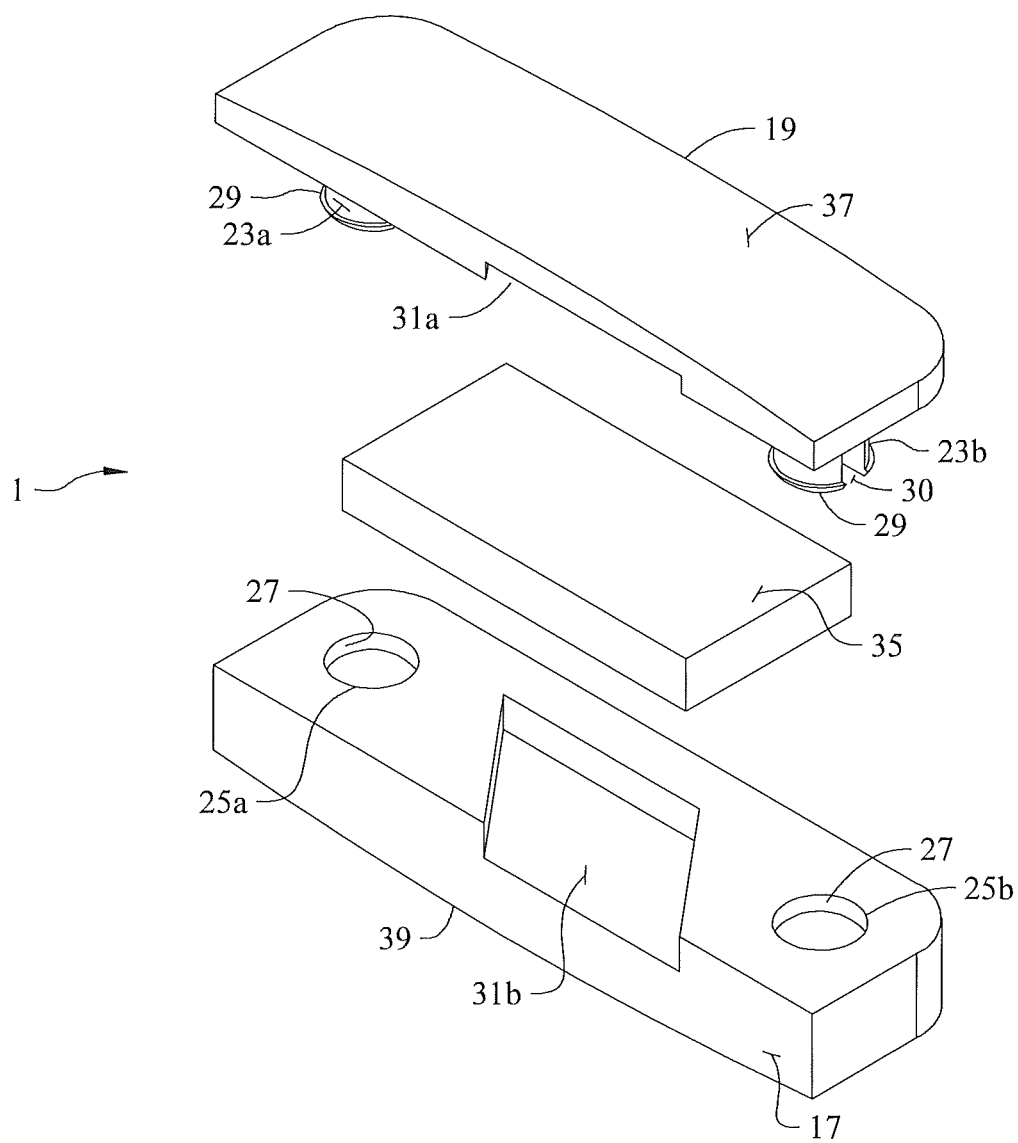
FIG. 18 is a top perspective exploded view of the implant.

As perhaps best shown in FIG. 18, each of the body members 17 and 19 has a respective oblique or angled slot 31a, 31b formed in its inner face. When the body members are assembled as shown in FIG. 13 and with the implant 1 installed as described above with the implant bearing on the cortical rims CR of the vertebrae bodies, the slots 31a, 31b are oriented so as to be generally in alignment with incision 11 in annulus 9 so to allow the blades of a distractor instrument (which may be similar to distractor 601 hereinafter described) to be inserted in line into these slots. With the operating blades of the distractor received in slots 31a, 31b, the distractor may then be operated so as to distract the body members 17 and 19 and so as to simultaneously distract the vertebrae bodies on opposite sides of the disc space DS a desired amount. The parallel distractor is used to expand the space 21 between the body members 17 and 19 using preoperative imagining and intraoperative tactile feedback of annular and ligamentous tensioning. Of course, when spacer 35 of the proper predetermined thickness is inserted in space 21, the desired amount of distraction is maintained. It will be appreciated that the angled slots 31a, 31b are substantially centered with respect to implant 1 so as to balance the distraction loading and so as to minimize binding of the stabilizing posts 23a, 23b within the openings of flanges 27 upon distraction and retraction of the body members relative to one another.

A spacer 35 of predetermined thickness is insertable within the space 21 between body members 17 and 19 once the disc space DS and the body members 17 and 19 of implant 1 have been distracted the desired amount. In accordance with this disclosure, a series of spacers 35 of predetermined thicknesses may be provided so that, depending on the amount of distraction needed, and depending on the disc space and the anatomical characteristics of the patient, a spacer is provided for the amount of distraction required. For example, spacers 35 may be provided in predetermined thicknesses of, for example, 1 mm, 2 mm, 3 mm, etc. The shape and size of spacers 35 distribute the anatomical spinal loads over a relatively wide surface area of the upper and lower body members 17, 19. The geometry of slots 31a, 31b facilitates easy withdrawal of the distractor instrument after shim or spacer 35 has been properly positioned between the implant members 17 and 19. Of course, it will be recognized that the distractor instrument may be used for final positioning and placement of implant 1 within the disc space.

As shown in FIG. 4, the length of implant 1 is sufficient so as to span the disc space DS anteriorly, and to bear on the cortical rims CR of the vertebrae bodies. The upper face 37 of upper body 19 and the lower face 39 of lower body 17 are preferably of a convex shape so as to generally conform anatomically to the disc space contacting the vertebrae endplates. This anatomic fit of the implant relative to the adjacent vertebrae in addition to the load sharing with the cortical rims of the vertebral bodies will maximize the load bearing capability of the implant. The outer faces 37 and 39 of body members 19 and 17 may be appropriately textured so as to prevent migration of the implant relative to the vertebrae. Still further, the outer anterior ends of the lower and upper body members are radiused, as indicated at 41, so as to generally conform to annulus 9 when the implant is positioned bilaterally within the disc space DS with the outer ends of the implant in bearing engagement with the hard cortical rims CR of the upper and lower vertebrae bodies. It will be noted that, as shown in FIG. 4, the ends of implant 1 may protrude somewhat through the annulotomies or openings 15a, 15b in the annulus 9. However, it will be understood that the anterior ends 41 of the lower and upper body members may be shaped to generally conform to the shape of the disc space DS so that they do not substantially project out beyond the outer surfaces of the vertebrae bodies. Of course, if the lower and upper body members are so shaped to better conform to the vertebrae bodies and to reduce the protrusion of the ends of the body members out beyond the disc 3, the ends of spacer 35 would be similarly shaped.

After the implant has been inserted in the disc space DS and oriented and positioned as above described with the ends of the implant supported at least in part by the cortical rims CR of the upper and lower vertebrae bodies and after the implant has been distracted as described and the desired thickness spacer 35 has been inserted between the lower and upper bodies 17 and 19, bone graft material may be packed between the implant and the posterior annulus filling the disc space. Of course, depending on the height of the cortical rim and the depth of the end plate after preparation for receiving bone graft material, the implant may also be supported at least in part by the end plates of the adjacent vertebrae bodies. It will also be understood that vertebrae fixation will be used in conjunction with implant 1. The fixation system used in conjunction with implant 1 is conventional and no particular system is preferred. It will be understood that as the bone graft material grows within and substantially fills the disc space DS, the vertebrae will be fused by this bone growth.

Figure 6:
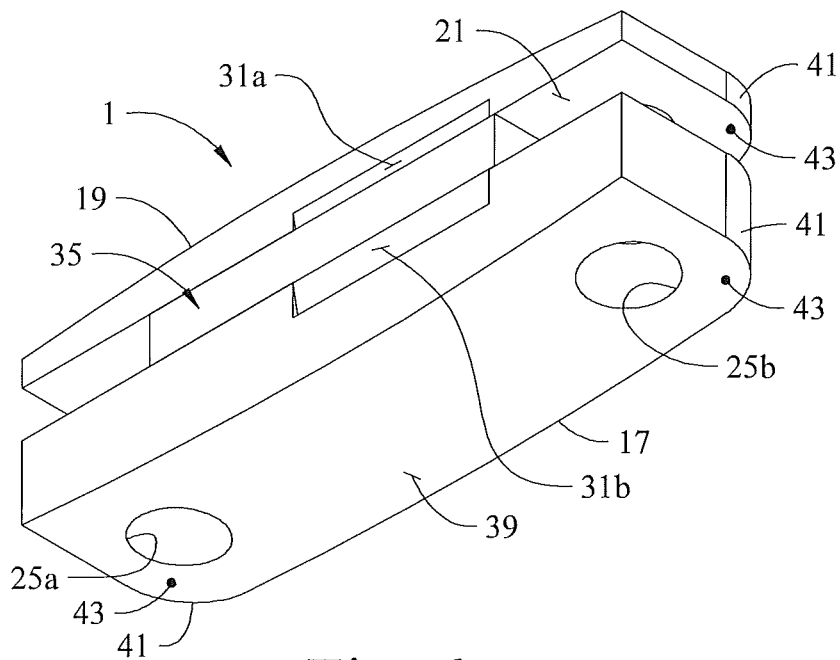
FIG. 6 is a posterior perspective view of the implant shown in FIG. 5, as viewed from below.
Figure 7:
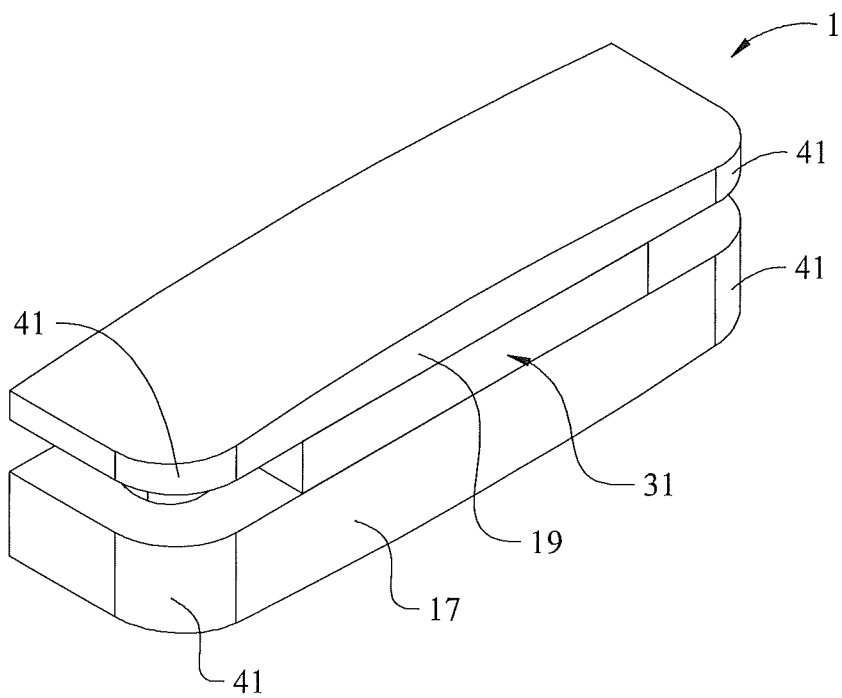
FIG. 7 is an anterior perspective view of the implant shown in FIG. 6, as viewed from above.
Figure 8:
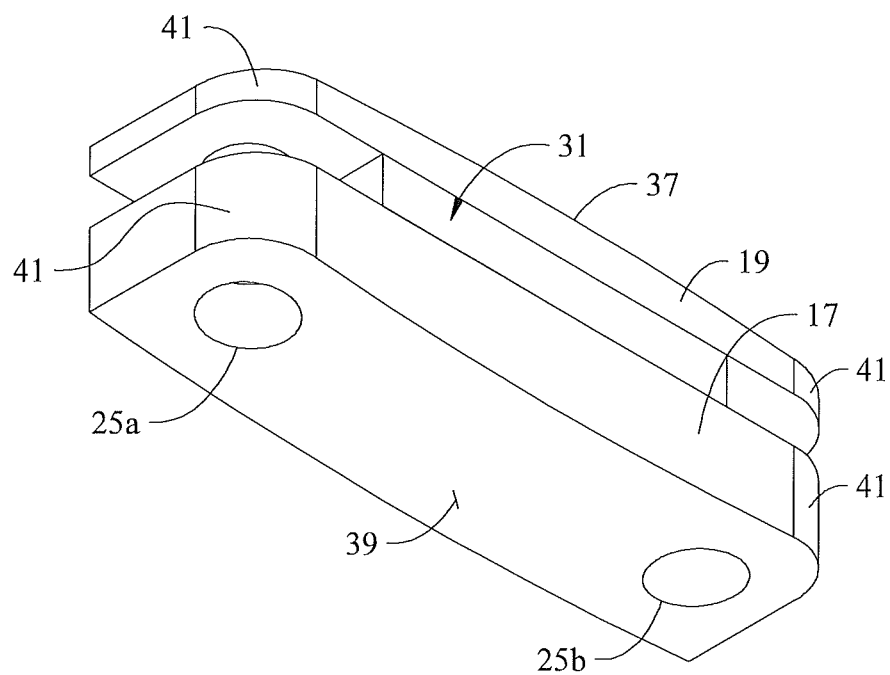
FIG. 8 is another anterior perspective view of the implant, as viewed from below.
Figure 9:
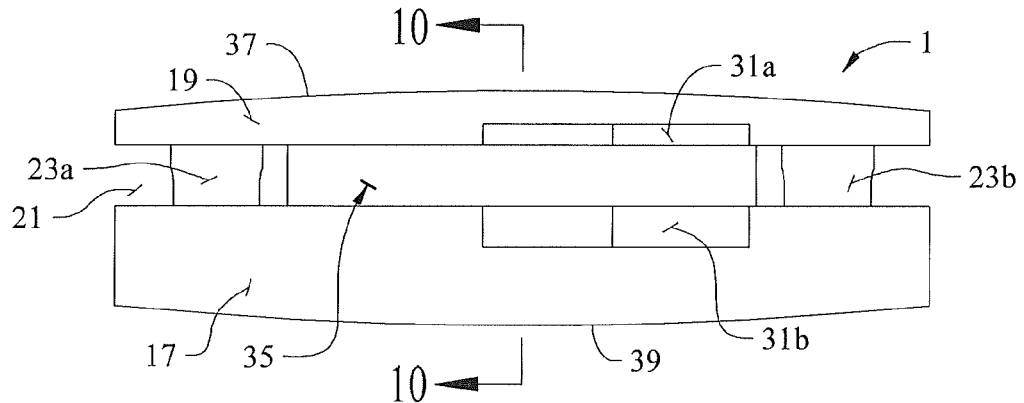
FIG. 9 is a posterior elevational view of the implant illustrating oblique slots in the inner faces of the upper and lower body members with a spacer inserted between the inner faces of the upper and lower body members.
Figure 10:
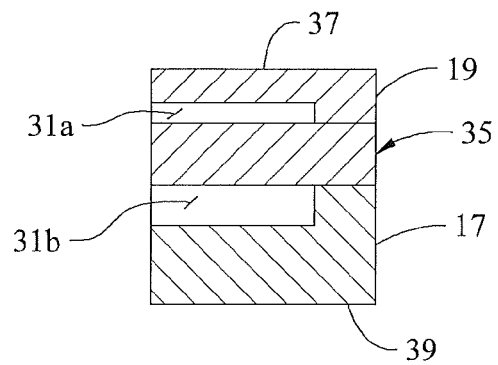
FIG. 10 is a vertical cross sectional view of the implant taken along line 10-10 of FIG. 9.
Figure 11:
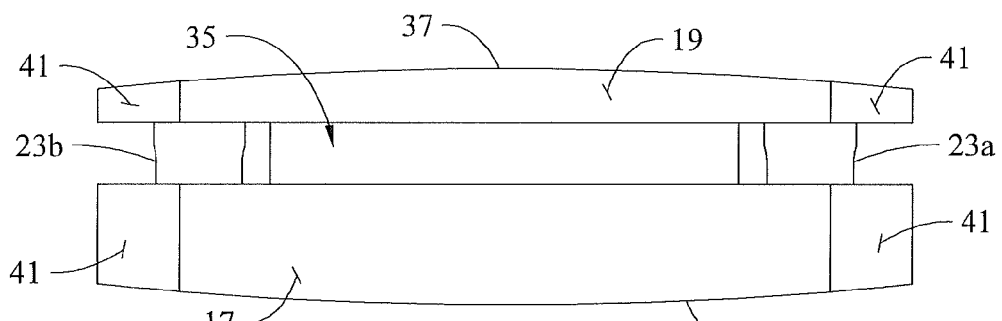
FIG. 11 is anterior view of the implant shown in FIG. 9.
Figure 12:
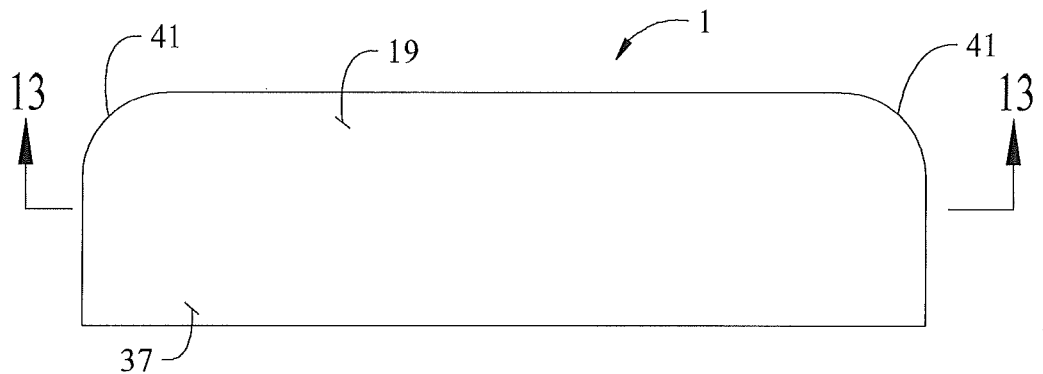
FIG. 12 is a top plan view of the implant.

It will be understood that the lower and upper bodies 17 and 19 of implant 1 and spacer 35 may be made of any suitable material such as surgical stainless steel, titanium, polyetheretherketone (PEEK), or carbon fiber reinforced PEEK, other surgical grade polymer or other material. Of course, the implant 1 and the spacers are delivered to the operating room in a sterile condition, and are available in a variety of lengths and profiles to as optimize patient fit. It may be preferable that implant 1 be made of PEEK because the modulus of elasticity of PEEK is similar to the modulus of elasticity of bone. However, PEEK is substantially radiolucent and thus is not readily viewable in radiographs. If PEEK is used for the implant, it is preferable that radio opaque markers, as indicated at 43 (as shown in FIGS. 5 and 6), be inserted within the implant so that the position and orientation of the implant may be fluoroscopically verified once the implant has been inserted in the disc space DS. Preferably, markers 43 are made of tantalum or other suitable metal so as to show more clearly on radiographic images.

With implant 1 properly positioned between the vertebrae, with the implant properly distracted, with spacer 35 of the proper thickness inserted between body members 17 and 19, and with the afore-mentioned bone graft material packed between the implant and the posterior annulus, conventional posterior spinal fixation appliances (not shown), such as pedicle screws, are applied. Compression is applied to the entire construct so as to restore or maintain sagittal alignment, so as to fixate the structural implant 1 within the disc space DS between adjacent vertebrae, and so as to provide the optimal environment for bone fusion of the vertebrae.

Referring now to FIGS. 19-41, a second embodiment of the implant of this disclosure is indicated in its entirety by reference character 101. The "primed" reference characters shown in FIGS. 19-30 ranging between 1 and 43 indicate parts having substantially the same construction and function as the parts identified by these reference characters 1-43 in FIGS. 1-18. However, some of these components have been modified to carry out a somewhat different function, as will be described.

Figure 19:
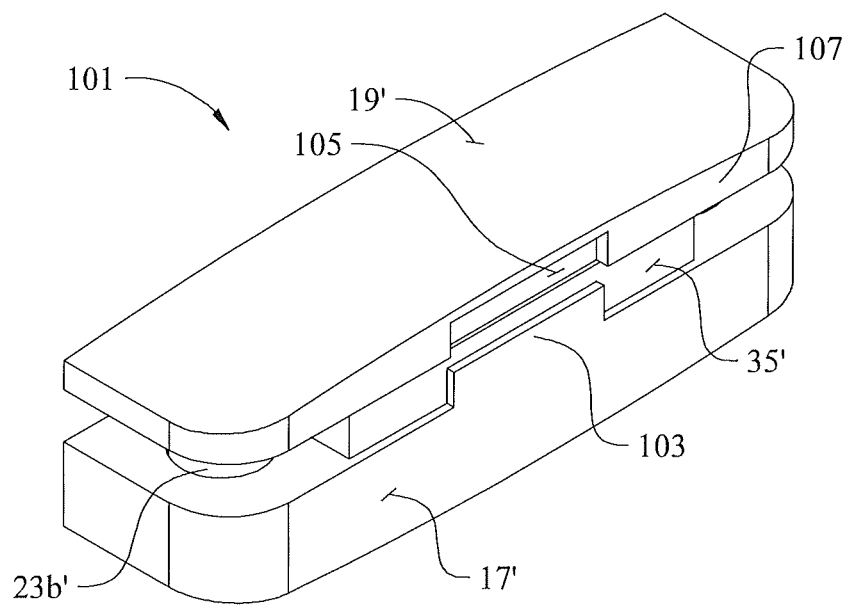
FIG. 19 is an anterior perspective view of a second embodiment of the implant of the present disclosure illustrating a tab extending upwardly from the anterior end of the lower body member with the tab being adapted to fit within a corresponding recess in the anterior face of the upper member so that upon distraction of the space between the body members and with a spacer disposed within the space between the upper and lower body member, the tab prevents anterior displacement of the spacer from between the body members.
Figure 20:
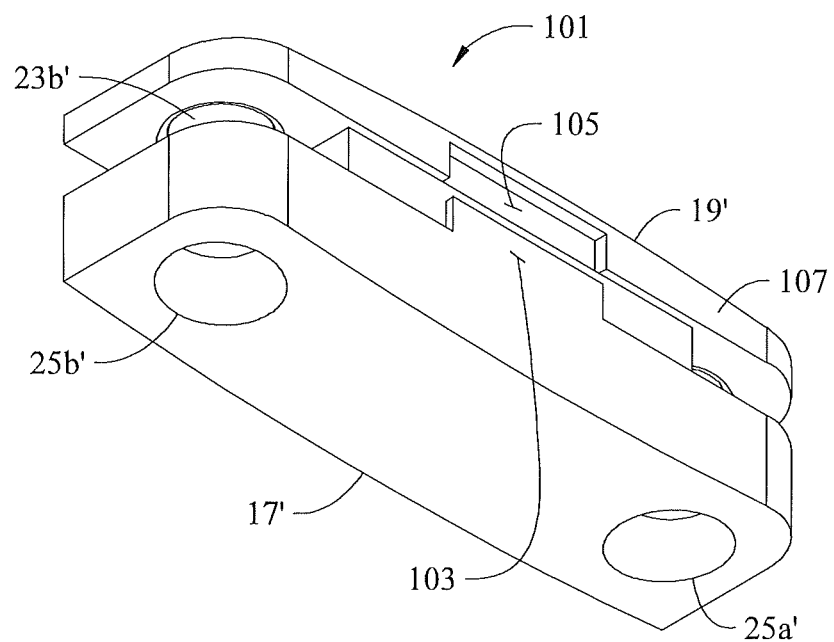
FIG. 20 is a bottom perspective view of the implant shown in FIG. 19.

As shown in FIG. 19, lower body member 17' has a tab 103 extending upwardly from the inner surface of one of the body members, for example, the lower body member along the anterior end thereof. This tab 103 extends up from the upper surface of the lower body member a distance sufficient so as to be at least partially slidingly received in a corresponding groove 105 formed in the anterior wall 107 of the other body member, for example, upper body member 19' when a spacer 35' is received within space 21' between the upper and lower body members and when the upper and lower body members are at least partially retracted with spacer 35' disposed therebetween. In this manner, tab 103 prevents movement of the spacer beyond the anterior end of the body members and thus self-locates the spacer in anterior/posterior direction. The tab further prevents anterior migration of the spacer 35' beyond the anterior edge of lower body member 17' during normal use of the implant by the patient. While tab 103 is shown to be an elongate single tab extending along the anterior edge of the spacer 35', it will be understood that the tab may actually be two or more spaced tabs extending upwardly from the spacer.

Figure 21:
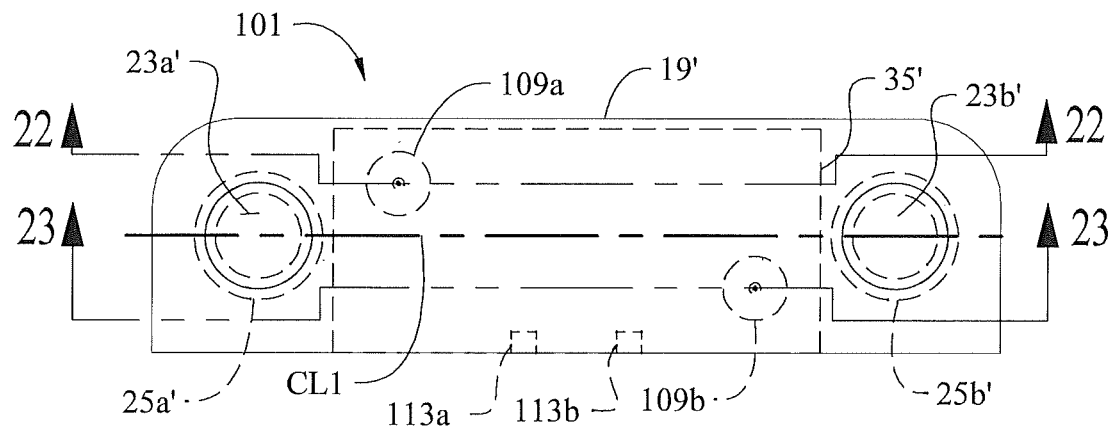
FIG. 21 is a top plan view of the implant shown in FIGS. 19 and 20, with a spacer (shown in dotted lines) positioned between the upper and lower body members.
Figure 22:
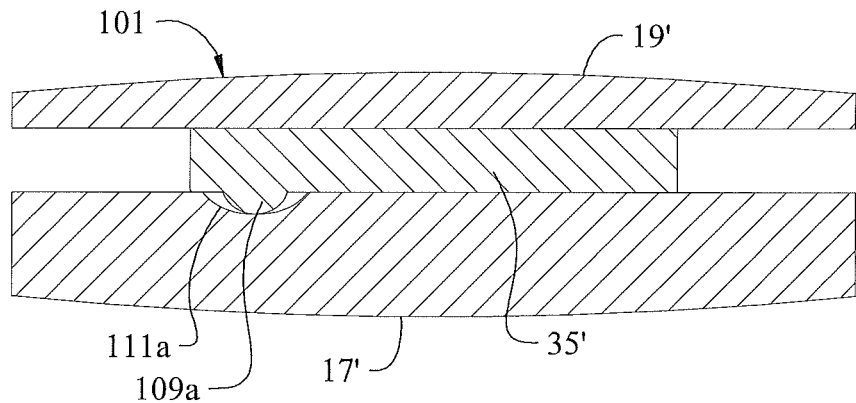
FIG. 22 is a vertical section view taken along line 22-22 of FIG. 21 illustrating a first or anterior detent protuberance projecting downwardly from the bottom face of the spacer with this first detent protuberance being received in a corresponding first enlarged recess in the top face of the lower body so as to aid in locating the spacer relative to the lower body member and so as to prevent displacement of the spacer relative to the lower body member upon retraction of the space between the upper and lower body members and upon application of compression and in normal use.
Figure 23:
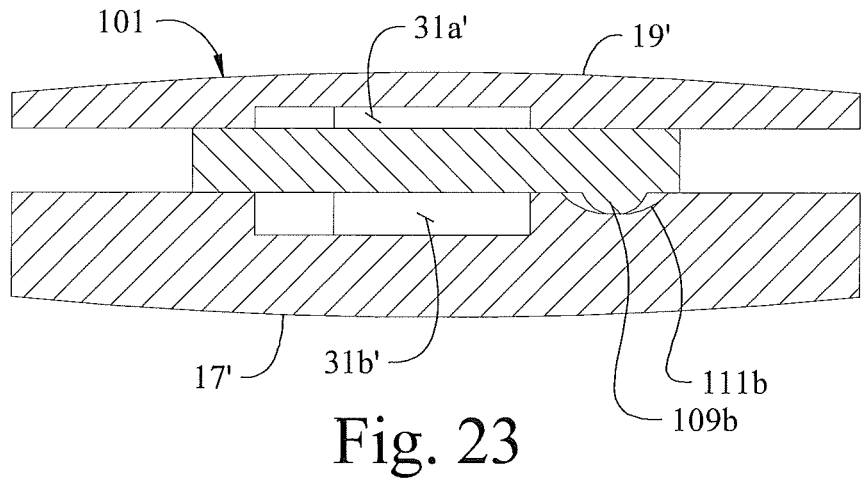
FIG. 23 is a vertical section view taken along line 23-23 of FIG. 21 illustrating a second or posterior detent protuberance projecting downwardly from the bottom face of the spacer with this second detent protuberance being received in a corresponding second enlarged recess in the top face of the lower body so as to aid in locating the spacer relative to the lower body member and so as to prevent displacement of the spacer relative to the lower body member upon compression of the space between the upper and lower body members.
Figure 24:
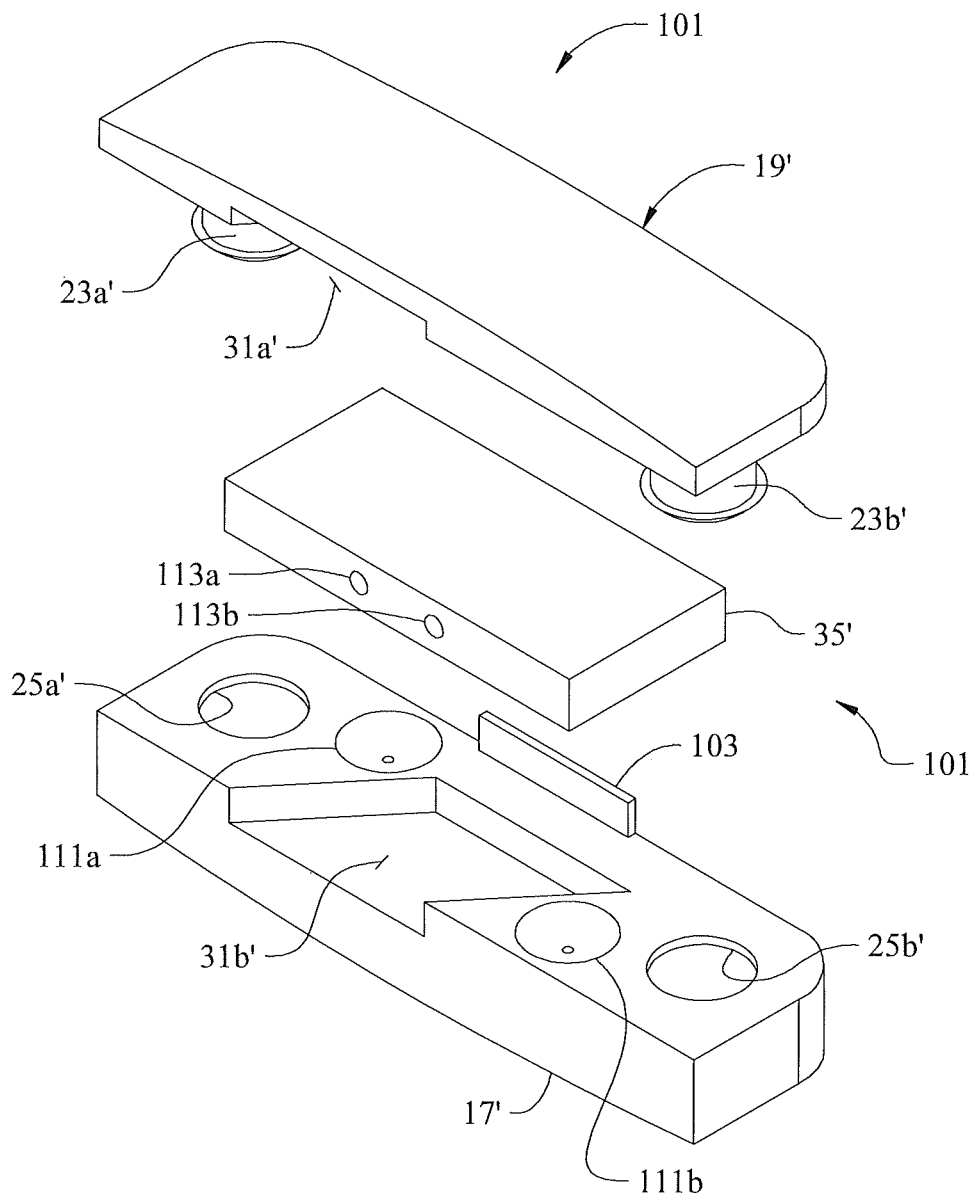
FIG. 24 is an exploded perspective view of the implant shown in FIGS. 19-23, as viewed from above.
Figure 25:
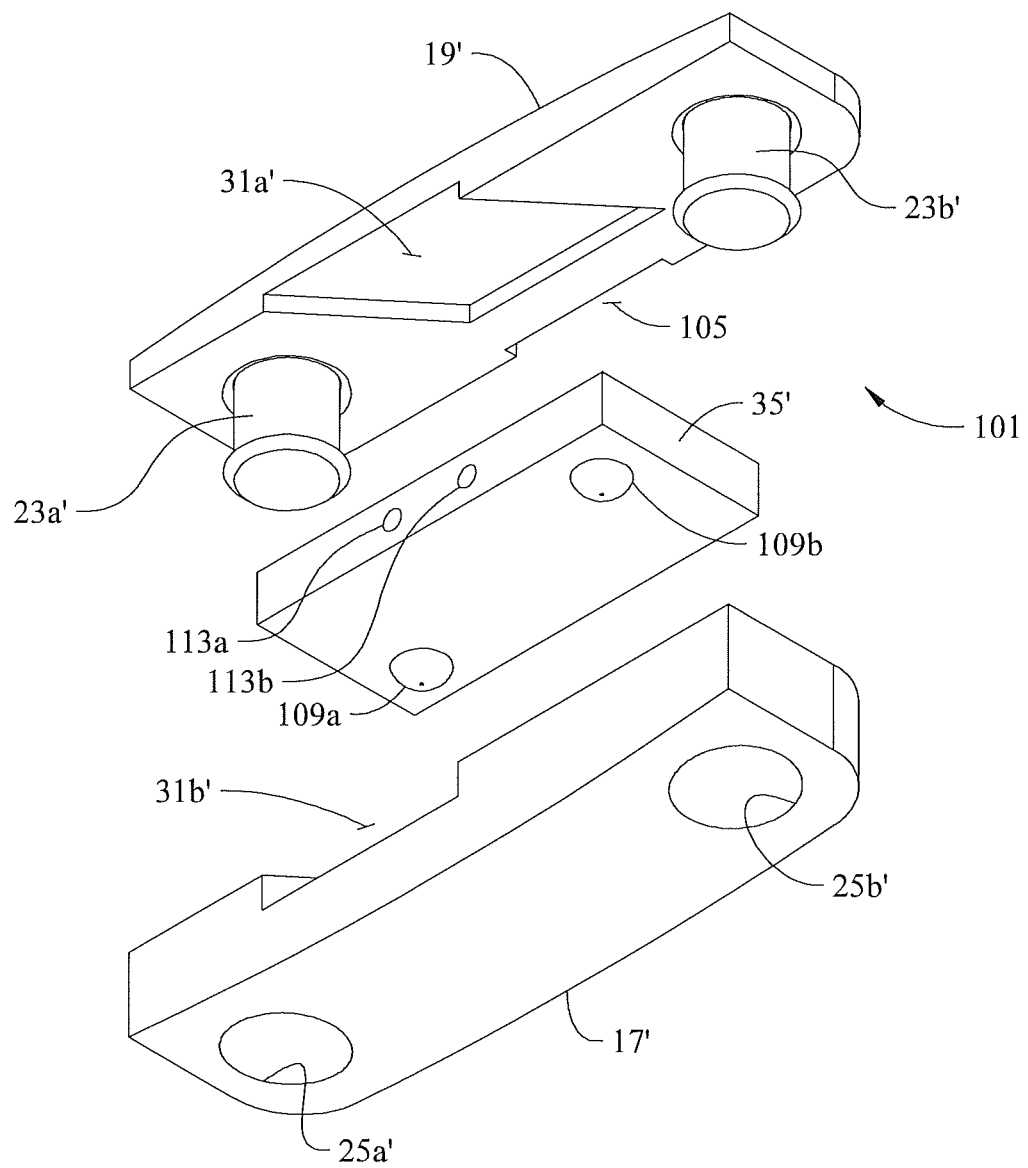
FIG. 25 is an exploded perspective view of the implant shown in FIGS. 19-24, as viewed from below, illustrating a pair of spaced detent protuberances on the bottom face of the spacer.
Figure 26:
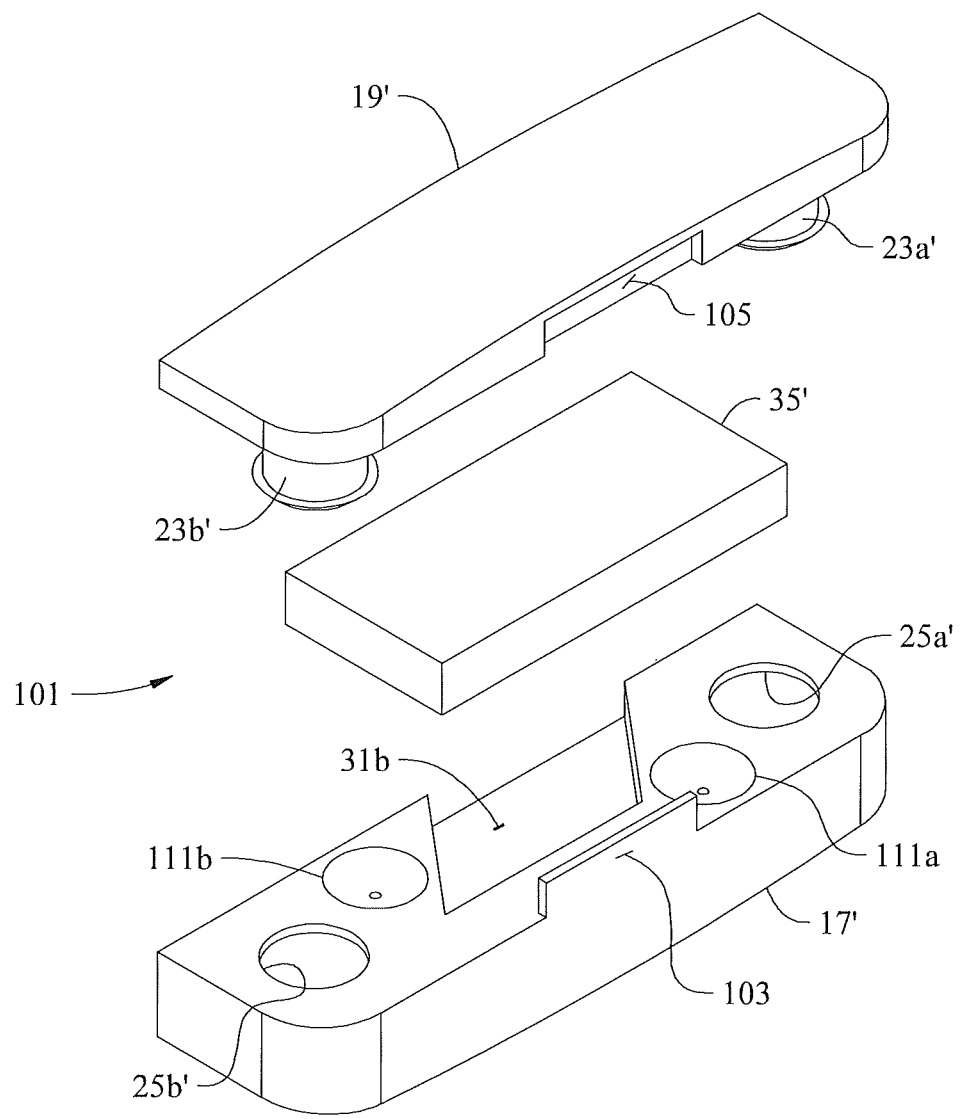
FIG. 26 is an anterior exploded perspective view, as viewed from above, of the implant illustrating the location of the first and second protuberance receiving recesses formed in the upper face of the lower body, as these recesses are positioned relative to the diagonal slot provided in the lower body for receiving the lower blade of a parallel distractor used to expand the space between the upper and lower body members.
Figure 27:
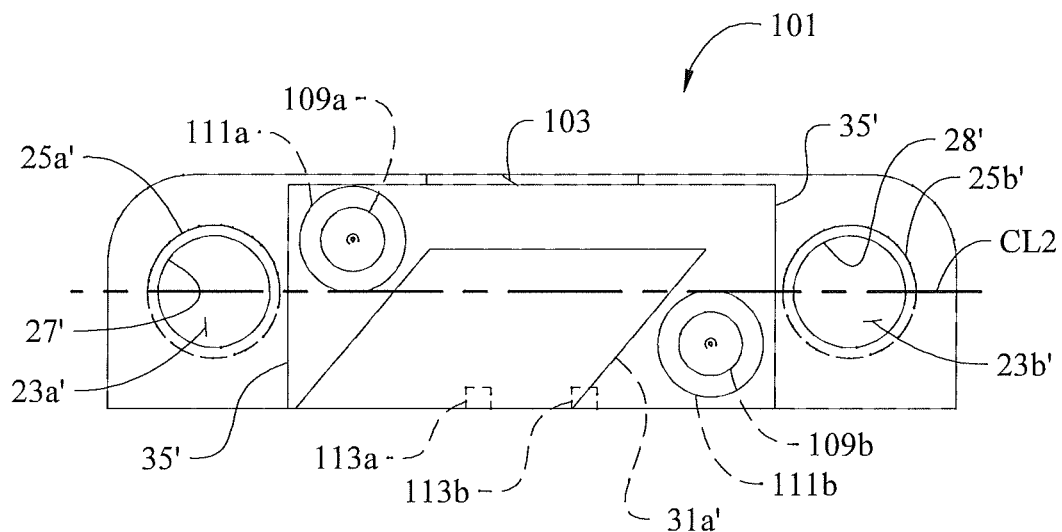
FIG. 27 is a top plan view of the lower implant body member shown in FIGS. 19-26 in which the spacer is substantially centered between the stabilizing posts and in which the anterior and posterior detent protuberances (as shown in dotted lines) are substantially centered relative to their respective recesses (also shown in dotted lines)

Referring now to FIGS. 21-30, the bottom face of spacer 35' is shown to have a pair of downwardly projecting male protuberances, as indicated at 109a, 109b. Each of these protuberances has a generally part-spherical convex outer surface for purposes as will be described. Further, the upper surface of lower body member 17' has a corresponding pair of female recesses, as indicated at 111a, 111b, positioned to receive a respective protuberance. Each of these female recesses has a generally part-spherical concave surface that is engaged by its respective male protuberance. As shown best in FIGS. 22-28, each recess 111a, 111b is larger in diameter than its respective protuberances 109a, 109b for purposes as will appear. As shown in FIG. 24, recesses 111a, 111b are spaced on opposite sides of slot 31b' in areas of the upper surface of lower body member 17' large enough to accommodate the recesses. As further shown in FIG. 21, protuberances 109a, 109b are preferably spaced on opposite sides of a first centerline CL1 (as shown in FIG. 21) of spacer 35' an equidistant amount. The respective recesses 111a, 111b are also preferably equidistantly spaced on opposite side of a second centerline CL2 (as shown in FIG. 27) diametrically extending through bores 25a', 25b' in lower body member 17'. However, those skilled in the art will recognize that the location of the protuberances and the recesses may be at any desired location. It will be further understood that while two protuberances and two recesses are shown, that other numbers of and shapes of the protuberances and recesses may be utilized.

It will be appreciated by those skilled in the art that instead of protuberances 109a, 109b being provided on the bottom face of spacer 35', they may instead (or may in addition) be provided on the upper face of the spacer and the recesses 111a, 111b may be provided on the lower face of the upper body member 19'. Further, it will be understood that the recesses may be provided on the spacer and the protuberances may be provided on a cooperating inner face of an adjacent body member.

It will also be appreciated that because recesses 111a, 111b are of larger diameter than their respective protuberance 109a, 109b, and because the generally part-spherical surfaces of the convex male protuberances engage the generally part-spherical female concave surfaces of their respective recesses, the mating convex surface of the protuberance acts like a cam follower and concave surfaces of the recesses act as a cam so that upon the application of compressive loads to the implant 101, the cooperating and complimentary protuberances and recesses will guide or force the protuberances to move downwardly toward the bottom of the concave recesses so as to self-position and/or to self-center the spacer relative to the body members. While the shape of the protuberances are recesses have been described as being preferably part-spherical, it will be understood that, in accordance with this disclosure, that other rounded shapes may be employed.

In use, as the distractor instrument (not shown) is withdrawn from slots 31a', 31b', as the disc space DS is retracted, and as compression is applied to the spinal column, this compression will tend to effect the above-described camming action that will self-center (or self-align) the spacer 35' in proper position within the space 21' between the upper and lower body members 19' and 17'. Further, with such compression loads applied to implant 101, protuberances 109a, 109b will interfere with (bear against) the sides of the recesses 111a, 111b thereby to securely hold or retain spacer 35' in its desired position within space 21'. Further, the complimentary protuberances and recesses, when under compression loading, cooperate with one another so as to resist migration of the spacer relative to the body members during normal use by the patient. It will also be appreciated that the height of the protuberances and the depth of the recesses are such that with the protuberances received within their respective recesses, the protuberances may carry at least some of the compression load applied to spacer 35' by the upper and lower body members 17', 19' of implant 101. Still further, with the protuberances 109a, 109b positioned in the bottom of their respective recesses 111a, 111b, respectively, the protuberances and the recesses prevent or resist movement (migration) and pull-out of the spacer relative to the body members 17', 19' in all directions. Also, the posts 23a, 23b will prevent lateral displacement of the spacer within the implant 101.

Figure 28:
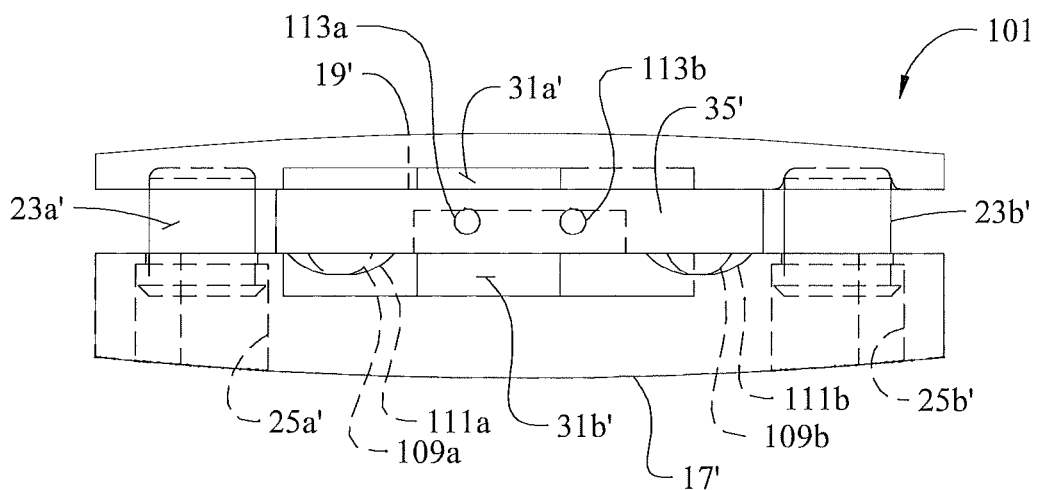
FIG. 28 is a posterior side elevational view of the implant shown in FIG. 27 with the space between the upper and lower body members distracted and with a spacer interposed between the upper and lower body members with the lateral ends of the spacer substantially centered between the stabilizing posts.

It will be further noted in FIGS. 27 and 28 that with the spacer in its desired position, the protuberances 109a, 109b are substantially centered relative to their respective recesses 111a, 111b so that spacer 35' is substantially centered between posts 23a' 23b'. It will be appreciated that so long as each of said protuberances are received anywhere within its respective recess, spacer 35' will be properly positioned in a desired general location between body members 17', 19'. It will be understood that with each of the protuberances substantially centered with respect to its respective recess, that the spacer will be located or positioned in a nominal position relative to the body members, as illustrated in FIGS. 27 and 28.

Further, it will be noted that the anterior end of the spacer 35' abuts against (or is in relatively close proximity to) the inner or posterior face of tab 103. In this manner, tab 103 cooperates with the anterior face of spacer 35' to as to prevent anterior displacement of the spacer from its desired general position between the body members 17', 19'. Because of the interaction of the generally convex surfaces of the protuberances and the concave surfaces of their respective recesses, spacer 35' is effectively constrained against anterior, posterior, lateral, and angled movement relative to the upper and lower body members.

Further, as previously described, bone graft material (not shown) is typically packed between the posterior face of implant 101 and the inner face of the posterior annulus substantially filling the disc space DS such that bone graft material also aids in preventing posterior movement of the spacer 35' relative to the body members. Thus, it will be appreciated that tab 103, and the cooperating generally rounded or part-spherical surfaces of protuberances 109a, 109b and recesses 111a, 111b, and the bone graft material prevent migration of the spacer 35' relative to the implant body members 17', 19' not only immediately following surgery, but also during normal use by the patient as the bone graft material fuses the vertebrae together.

Figure 29:
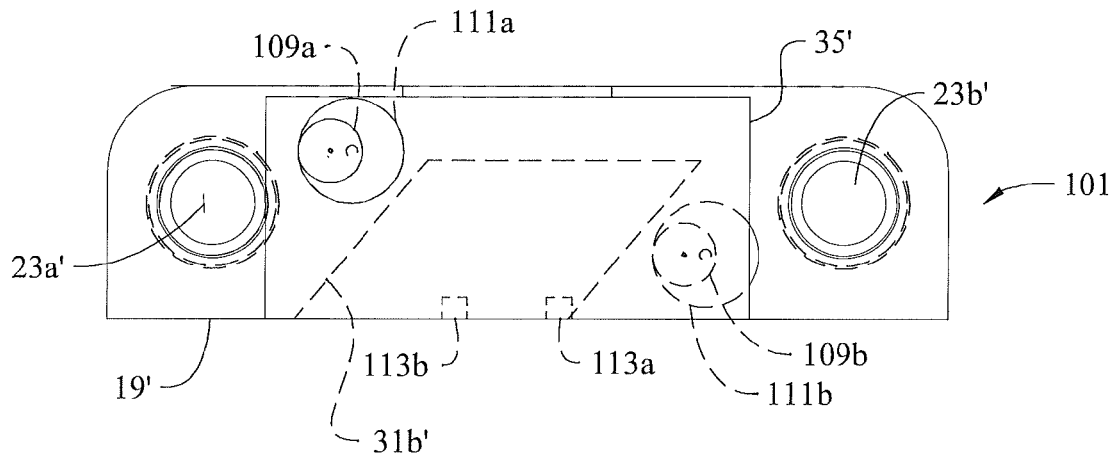
FIG. 29 is a top plan view of the lower implant body with the spacer being offset within the space between the stabilizing posts toward and bearing against the left-hand post such that both the left-hand post and the detent protuberances are received in their respective recess so as to positively prevent lateral movement of the spacer, and such that the protuberances cooperating with their respective recesses positively prevent movement of the spacer relative to the implant bodies.
Figure 30:
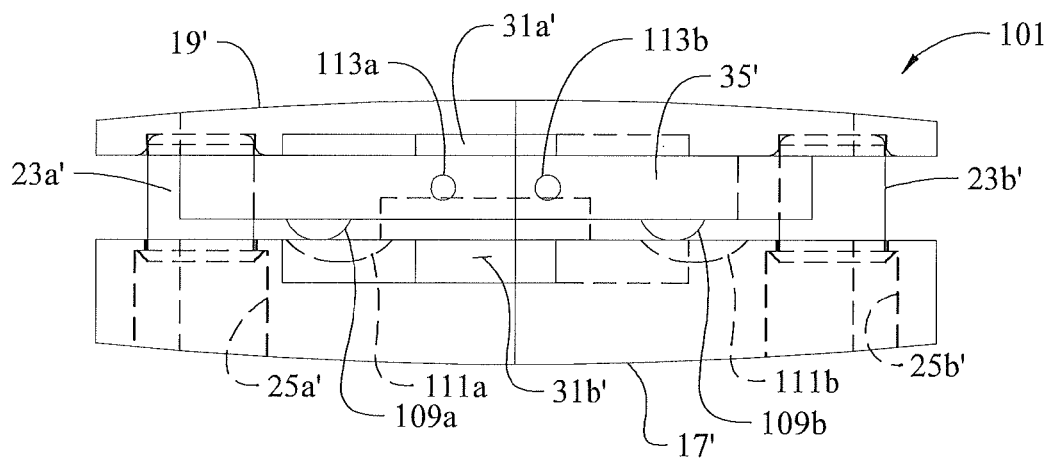
FIG. 30 is a posterior side elevational view of the implant shown in FIG. 29 with the spacer located in the position shown in FIG. 29 with the space between the implant bodies members distracted a distance greater than the thickness of the spacer.
Figure 31:
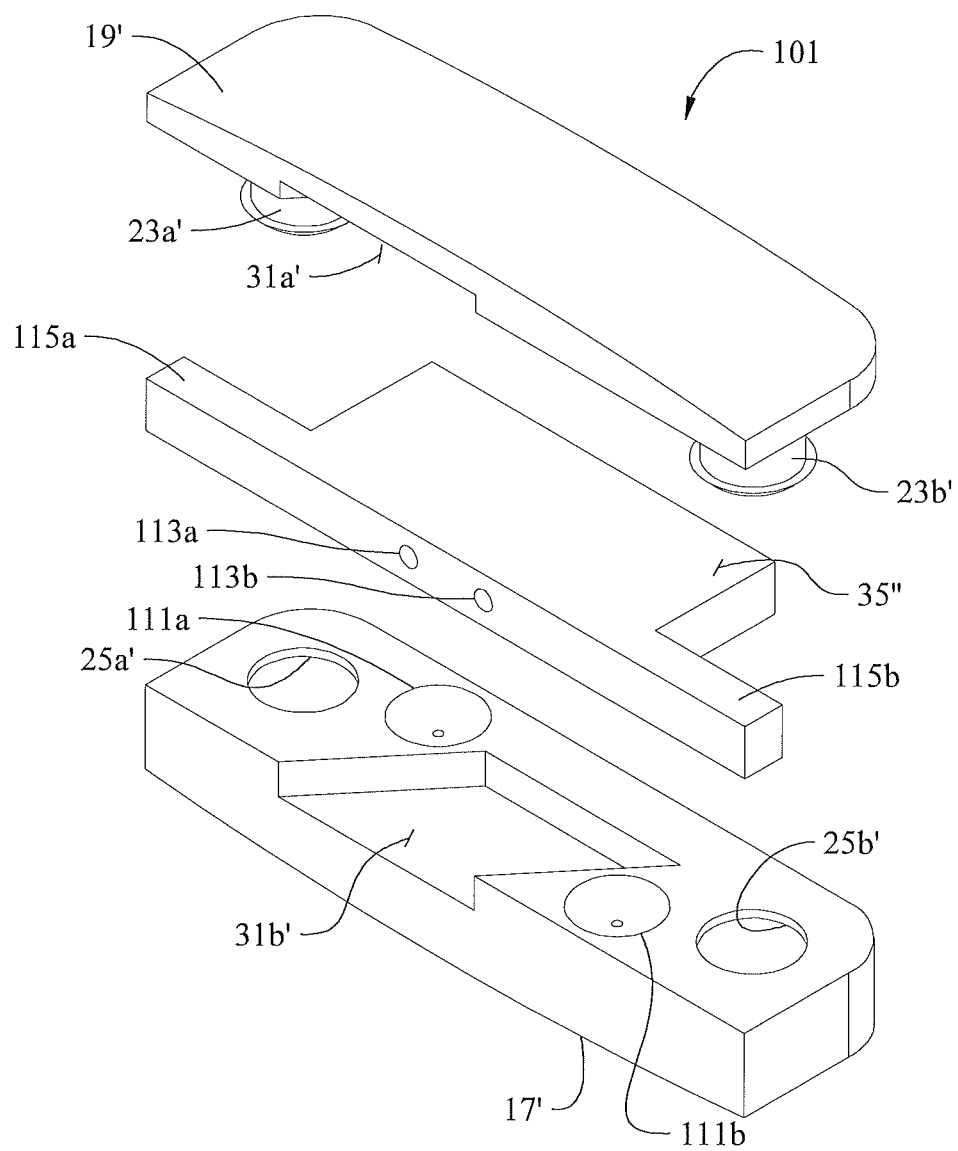
FIG. 31 is an exploded perspective view of the implant having an alternative spacer having a "wing" or extension extending laterally from each posterior side of the spacer for cooperating with the stabilizing posts thereby to prevent anterior movement of the spacer beyond a predetermined location for the spacer between the body members.
Figure 32:
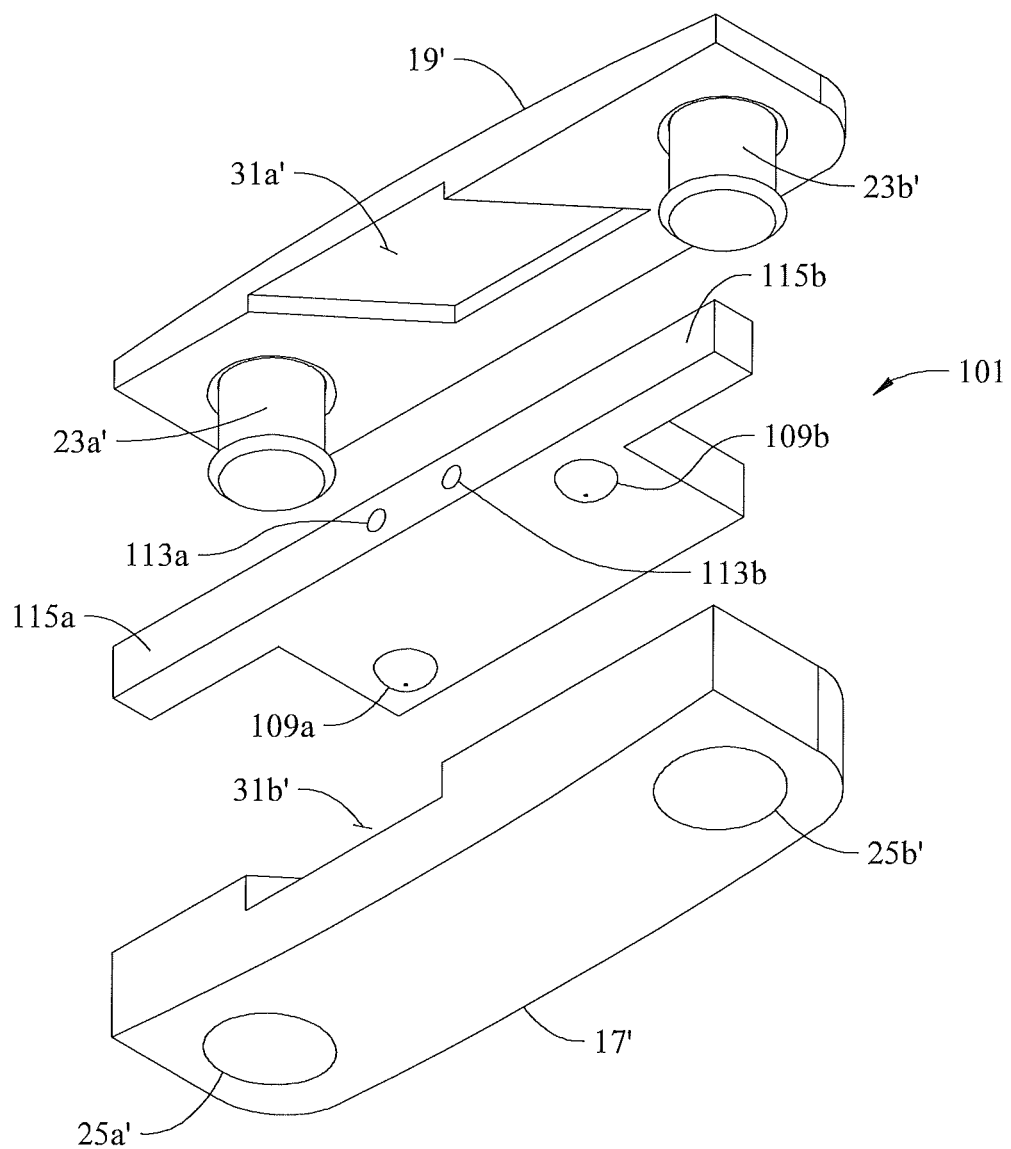
FIG. 32 is a posterior exploded perspective view of the implant and spacer illustrated in FIG. 31.

Referring now to FIGS. 29 and 30, the body members 17' and 19' are shown with spacer 35' laterally offset to the left such that the left end of the spacer is in contact with stabilizing post 23a' and such that the protuberances 109a, 109b are disposed above the extreme left-hand reaches of their respective recesses 111a, 111b. Upon retraction of the disc space DS and upon the application of compression loads to the construct, the previously described camming action of the convex protuberances engaging the concave recesses cause the spacer to move or shift relative to the body members and to be at least partially self-aligned and self-centered with respect to the lower body members so as to be closer to its nominal desired general location, as shown in FIGS. 27 and 29. However, those skilled in the art will recognize that so long as the protuberances are received within their respective recesses, the spacer will be located within its desired general location and that such location results in an acceptable insertion and location of the spacer in implant 101.

This self-centering, self-aligning feature of the spacer 35' means that upon installation of spacer 35' during the surgical procedure, the surgeon need only place the implant 101 within the disc space DS (as described above in regard to implant 1). With the implant 101 so positioned, the surgeon then, using the above-described distractor instrument, distracts body members 17' and 19' and inserts spacer 35' within space 21' between the body members. It will be appreciated that due to tab 103, the stabilizing posts 23a', 23b', and the length of the spacer, the spacer need only be positioned between the posts and somewhat to the posterior of tab 103 such that upon removal of the distractor instrument (which will allow retraction of the vertebrae) and upon the application of a compressive load to the spinal column, the above-described self-centering and self-aligning features of the protuberances 109a, 109b and recesses 111a, 111b will move the spacer from the position as shown in FIGS. 29 and 30 to the substantially centered position of the spacer shown in FIGS. 27 and 28. Of course, if the spacer is shifted to the right, retraction and the application of compressive loads will also self-center and self-align the spacer. Additionally, if there is some angular displacement of the spacer, the protuberances and recesses will straighten the spacer relative to the body members in the same manner.

Further, those skilled in the art will recognize that upon application of compression loads (as herein described) and/or upon the application of repeated micro-motion compressive spinal column loads by the patient, as during sitting or walking, the cooperating protuberances 109a, 109b and recesses 111a, 111b maintain the self-alignment and self-centering of the spacer relative to the upper and lower body members and prevent migration of the spacer relative to the body members.

It will be further appreciated by those skilled in the art that if during the surgical procedure a first spacer is inserted within space 21' between the body members 17' and 19' and if it is determined that the first spacer should be removed, the surgeon need only insert the distractor blades of the distractor instrument (not shown) into slots 31a', 31b' of the body members so as to distract or expand space 21', Then, the first spacer 31' may be readily removed by gripping the spacer with a clamp and removing it from between the body members and to withdraw the spacer through the above-described incision 11 in the annulus 9, as shown in FIG. 4C. Then, a second spacer of, for example, a different (greater) thickness, may be readily inserted.

As indicated at 113a, 113b in FIGS. 19-30, a pair of holes is provided in spacer 35' so as to more readily permit the surgeon to grasp the spacer by means of a clamp or other instrument so as to enable the surgeon to maneuver the spacer within space 21' between the body members 17', 19', or to remove the spacer.

It will be further appreciated that with the expandable lumbar interbody or implant 1 of the present disclosure in its collapsed height condition without spacer 35 installed between the upper and lower body members 17, 19, it is easier for the surgeon to insert the interbody into the disc space DS through the annulotomy 11, and the interbody is more readily maneuverable by the surgeon within the disc space so that the interbody spans the apophyseal ring and so that the ends of the interbody are properly inserted in the anterolateral annulotomies 15a, 15b, as generally shown in FIG. 4. It will also be appreciated that with the interbody 1 in its collapsed condition, it is much easier to remove the interbody from the disc space.

Figure 33:
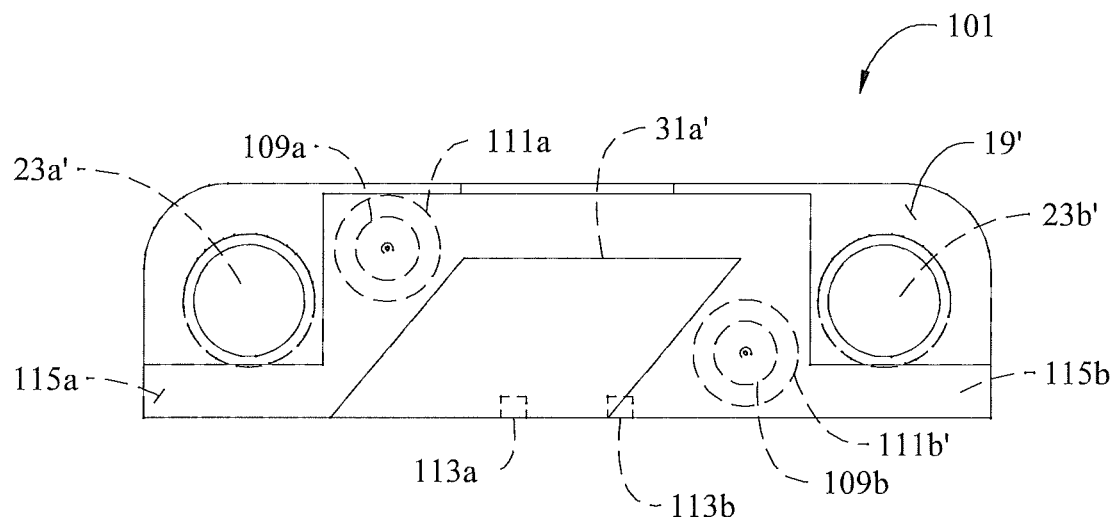
FIG. 33 is a top plan view of the implant shown in FIGS. 31 and 32 with the alternative spacer positioned between the upper and lower body members with the wings or extensions bearing against their respective posts so as to prevent anterior movement of the spacer beyond the position of the spacer shown.
Figure 34:
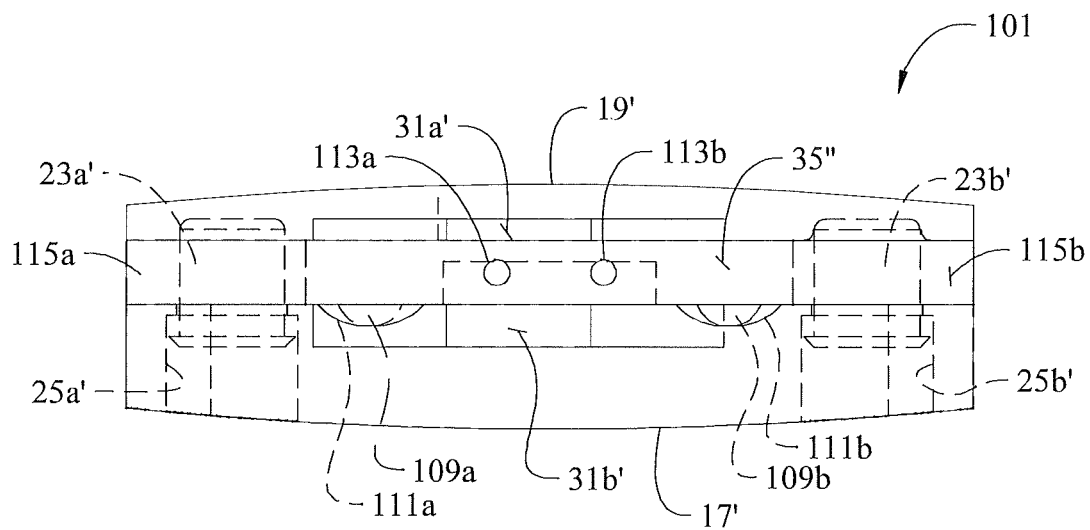
FIG. 34 is a posterior side elevational view of the implant shown in FIG. 33.
Figure 35:
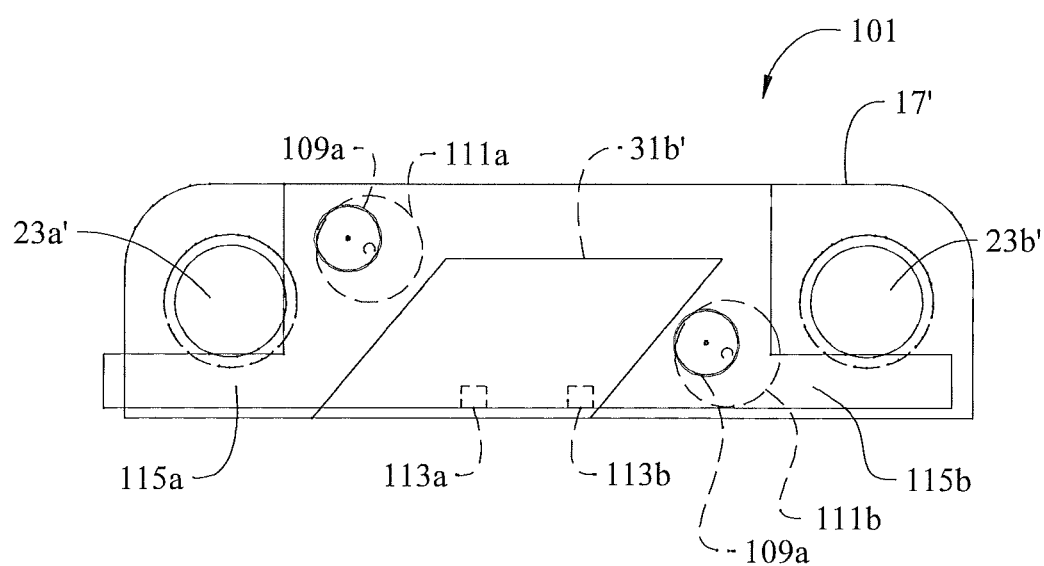
FIG. 35 is a top plan view of the lower body member having the alternate spacer positioned thereon with the left lateral side of the spacer bearing against the left post and with the wings or extensions bearing against the respective posterior faces of their respective posts so as to prevent anterior movement of the spacer relative to the lower body member beyond the position shown.

Referring now to FIGS. 31-35, an alternative embodiment of spacer 35' is shown and is indicated in its entirety at 35". This spacer 35" is shown to have a pair of wings or extensions 115a, 115b, one on each end of the spacer, extending laterally from the posterior side of the spacer. The anterior faces of these wings or extensions bear against the posterior faces of respective posts 23a', 23b' so as to prevent anterior movement of the spacer 35" beyond its predetermined position, as shown in FIGS. 33 and 35. These wings are an alternative structure to or in addition to tab 103 for locating the spacer in anterior/posterior position relative to the body member and for preventing anterior movement of the spacer beyond a desired location. It will be further appreciated that the length of each wing 115a, 115b is such that with the spacer positioned within space 21' (as shown in FIG. 35) such that one lateral side of the spacer bears against its respective post 23a' or 23b', the wing on the opposite lateral side of the spacer still engages the posterior face of its respective post such that both of the wings bear against their respective posts and thus positively prevent insertion of the space in anterior direction beyond a desired anterior position relative to the body members 17', 19'.

Thus, upon installation of the spacer 35", the spacer need only be oriented its protuberances 109a, 109b facing body member 17', with the wings 115a, 115b facing toward the posterior of the implant 101, with the body of the spacer positioned between the posts 23a, 23b'. Then upon retraction of the vertebrae spacing and upon the application of compression loading to the implant 101, the protuberances and the recesses will cooperate, as previously described, so as to self-center and to self-align the spacer relative to the body members. Further, with the protuberances received in their respective recesses and with such normal compression loads applied to the implant, the protuberances and recesses will effectively prevent movement or migration of the spacer relative to the body members. Still further, with bone graft material (not shown) packed within the disc space DS on the posterior side of implant 101, the bone graft material will also aid the protuberances and recesses in preventing movement or migration of the space from between the body members.

As shown best in FIG. 33, spacer 35" has an oblique slot 117 extending part way through the upper or lower (or both) faces of the spacer. This slot provides clearance for an operating blade of a distractor to be inserted within the slot to aid in positioning the spacer between the inner faces of the body members of the implant. The slot 117 in the spacer is generally in register with the slot 31a' or 31b' in its proximate body member.

Figure 36:
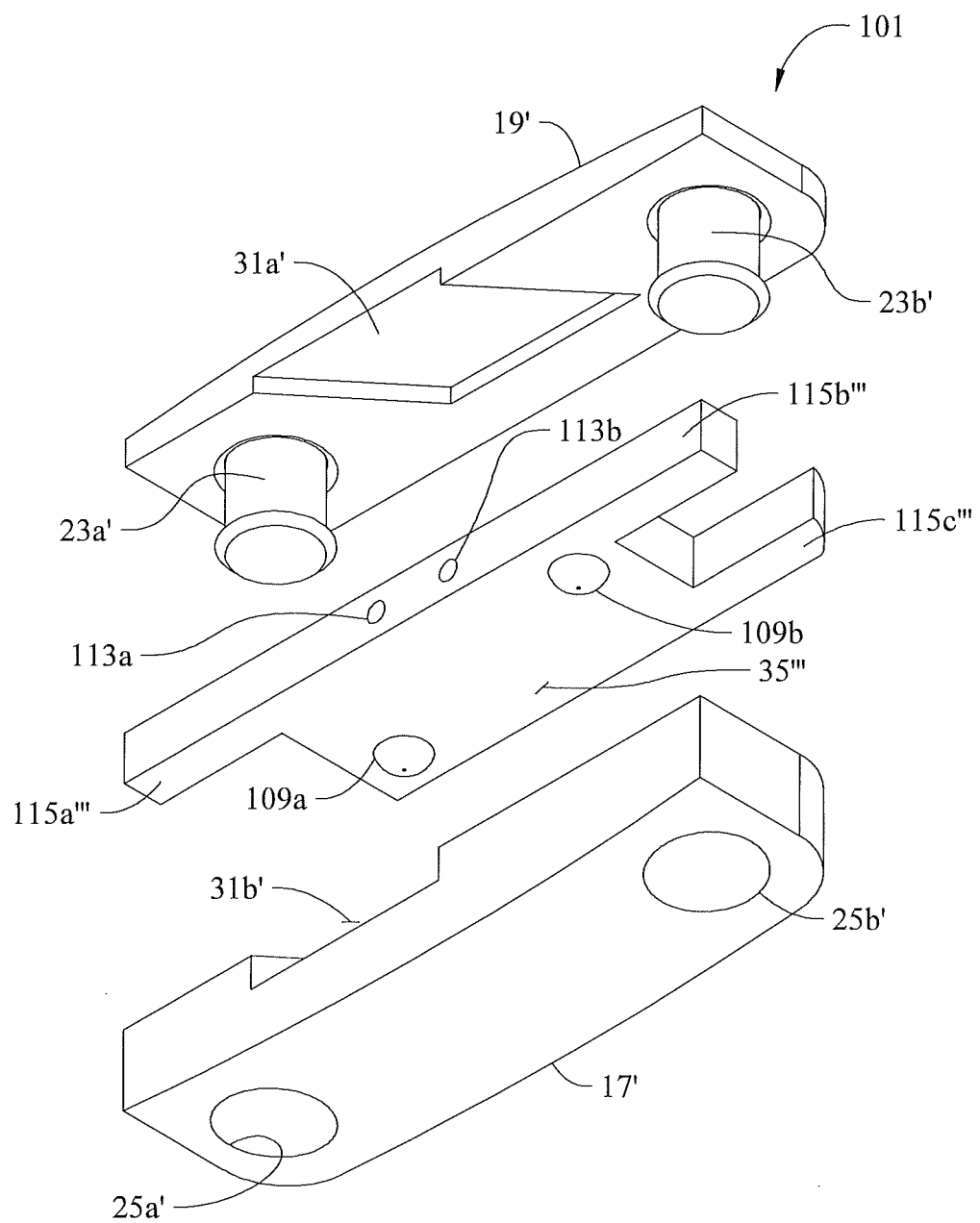
FIG. 36 is a bottom perspective exploded view of still another embodiment the implant similar to that shown in FIGS. 31-35 in which the spacer has a pair of "wings" or tabs on one end and a single "wing" or tab on the other end with the space between the pair of tabs being spaced as to receive a post such that with the spacer inserted between the implant bodies and rotated such that the spacer is substantially parallel to the implant bodies where the posterior tabs prevent anterior movement of the spacer relative to the posts and the anterior tab prevents posterior movement of the spacer.
Figure 37:
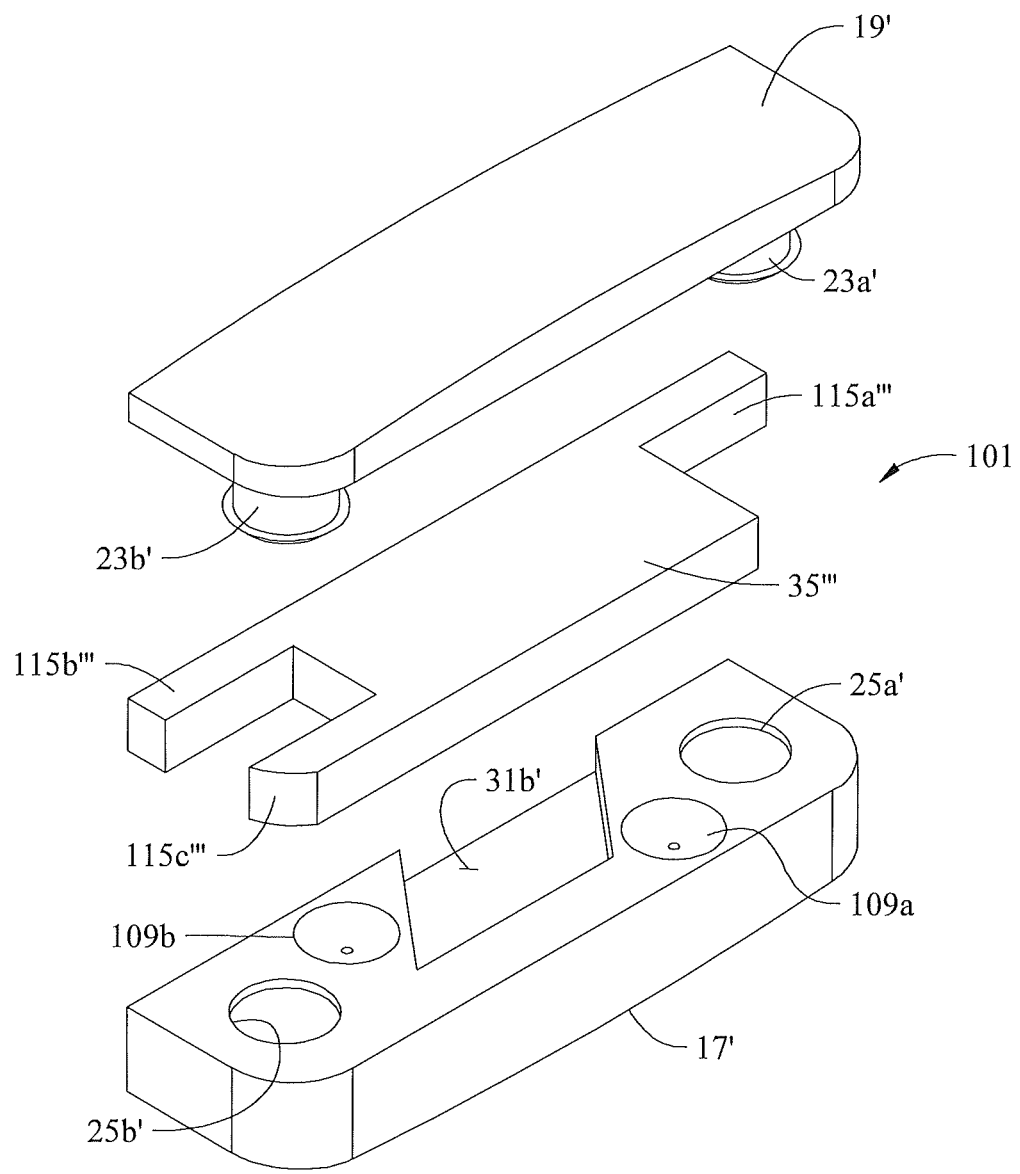
FIG. 37 is a top perspective exploded view of the implant and spacer shown in FIG. 36.
Figure 39:
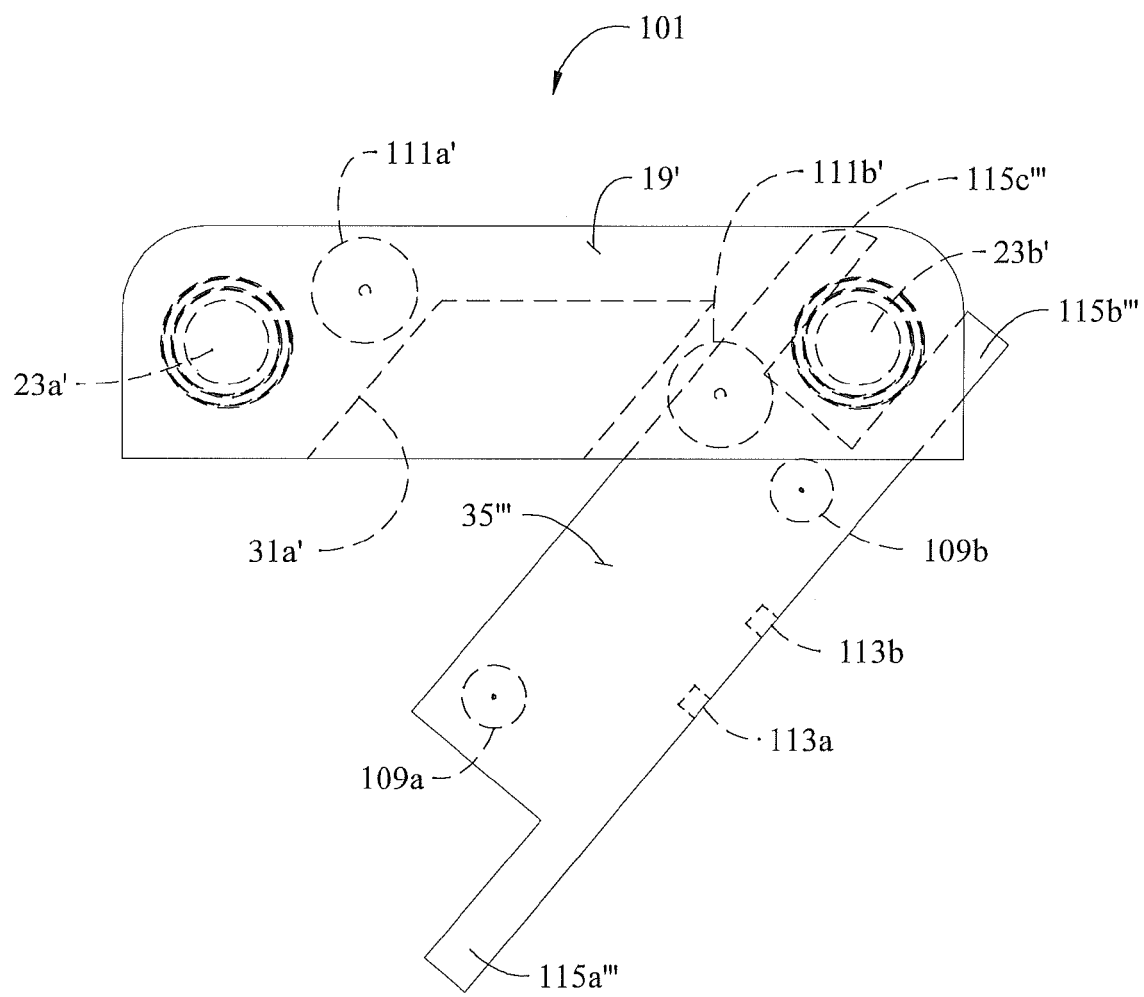
FIG. 39 is a view similar to FIG. 38 with the spacer partially inserted between the upper and lower implant bodies with a stabilizing post received between the pair of spaced wings or tabs.
Figure 40:
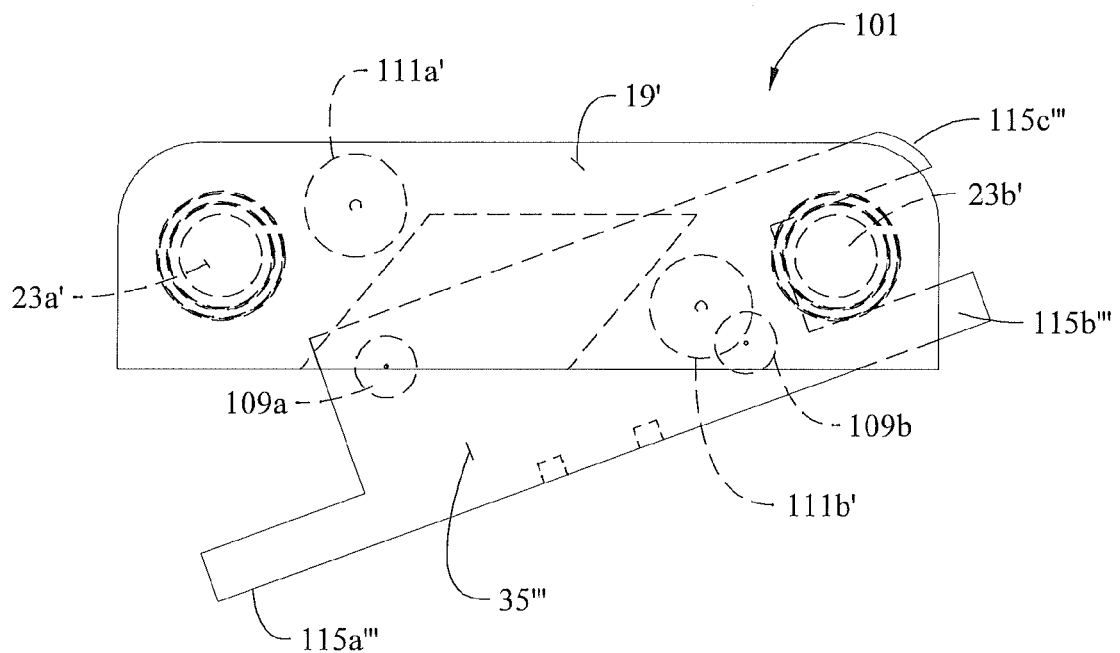
FIG. 40 is a view similar to FIG. 39 showing the spacer partially rotated toward its installed position in which the spacer is substantially parallel to the body members.
Figure 41:
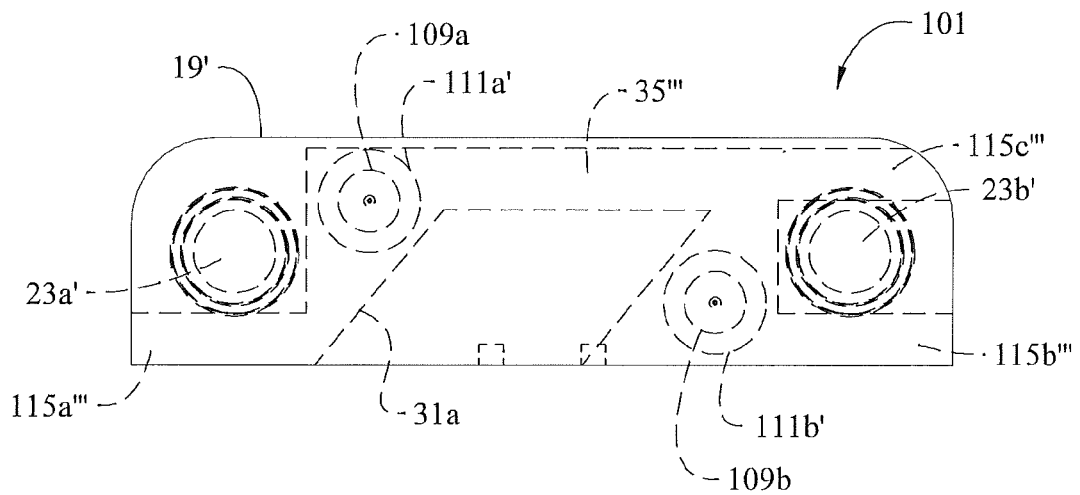
FIG. 41 is a view similar to FIG. 40 showing the spacer in its fully installed position.

Referring now to FIGS. 36-41, an alternative embodiment of spacer 35' is shown and is indicated in its entirety at 35'''. This spacer 35''' is shown to have a pair of wings or extensions 115a''', 115b''', one on each lateral end of the spacer, extending laterally from the posterior side of the spacer. In addition, on the right-hand end of the spacer (as shown in FIG. 36) has another wing 115c''' spaced from wing 115b''' with the space therebetween being sufficient so as to readily receive stabilizing post 23b'. The anterior faces of wings or extensions 115a''', 115b''' bear against the posterior faces of posts 23a', 23b' so as to prevent anterior movement of the spacer 35''' beyond its predetermined position, as shown in FIG. 41. In addition the inner or posterior face of wing 115c''' is positioned to engage against post 23b' so as to prevent posterior movement of the spacer 35'''. It will be further appreciated that the length of each wing 115a''', 115b''', and 115c''' is such that with the spacer 35''' positioned within space 21' (as shown in FIG. 41) such that one lateral side of the spacer bears against its respective post 23a' or 23b', the wing 115a''' or 115b''' on the opposite lateral side of the spacer still engages the posterior face of its respective post such that both of the wings bear against their respective posts and thus positively prevent insertion of the spacer in anterior direction beyond a desired anterior position relative to the body members 17', 19'.

Figure 38:
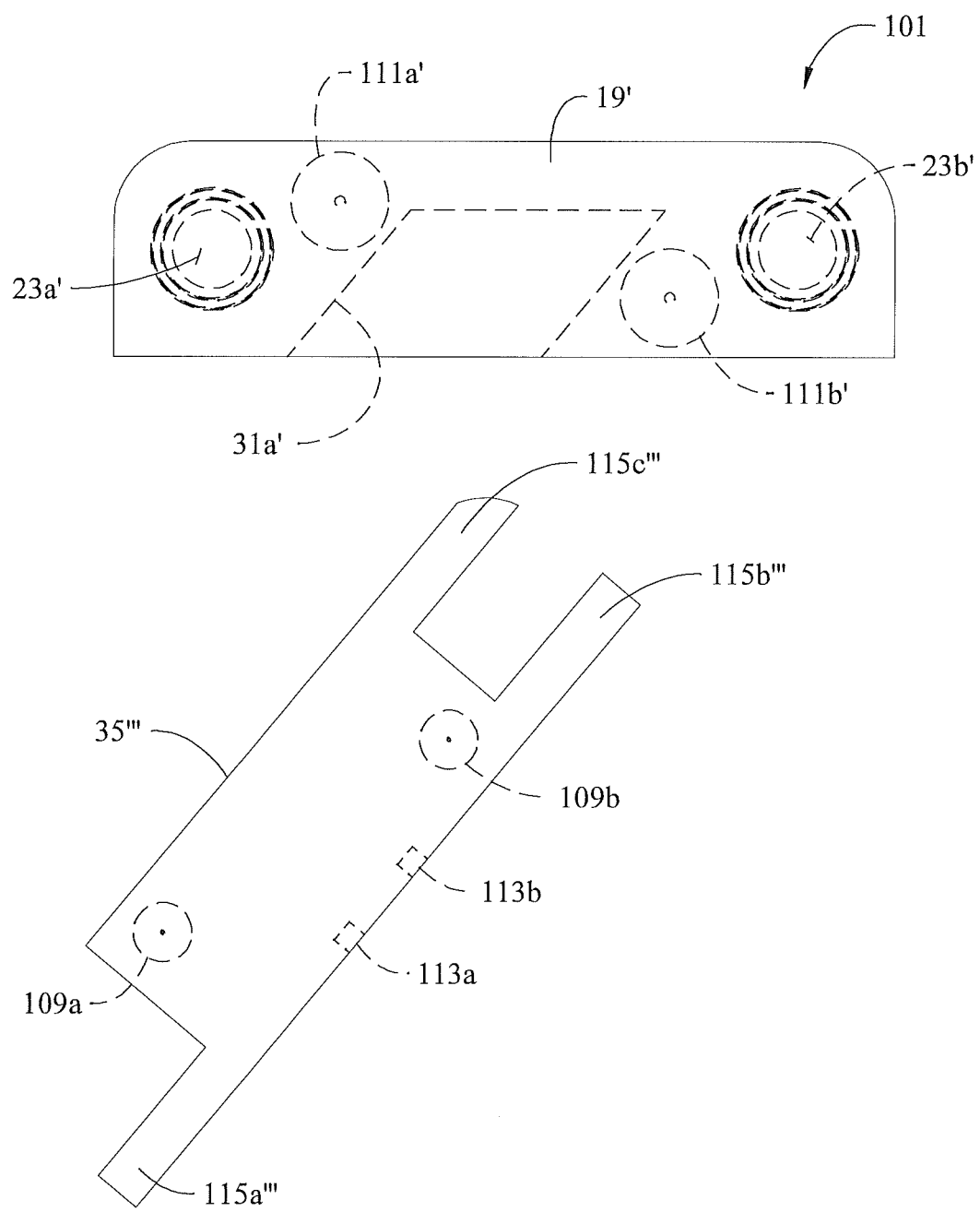
FIG. 38 is a top plan view of the implant and the spacer showing the spacer prior to being inserted between the implant bodies oriented at an angle with respect to the implant body so as to be inserted between the implant bodies.

As shown in FIG. 38, upon installation of spacer 35''', the spacer is oriented at an oblique angle with respect to the implant bodies 17', 19' when the implant bodies are positioned between adjacent vertebrae and with the implant bodies distracted (as generally shown in FIG. 4) so as to receive that spacer inserted through an annulotomy 11 on the opposite side from that shown in FIG. 4. As shown in FIG. 39, the spacer is moved diagonally between body members 17', 19' until post 23b' is received between wings 115b''', 115c'''. Then, as shown in FIG. 40, the spacer is rotated so that the spacer 35''' is rotated clockwise about post 23b' (as shown in FIG. 40) until wing 115a''' bears against the posterior surface of post 23a'. In this position, post 23b' is received between wings 115b''' and 115c''' and wing 115''' bears against the posterior surface of post 23a'.

It will be appreciated that if spacer 35''' is to be inserted through an annulotomy 11 of the opposite side of the disc from that shown in FIG. 4, the spacer 35''' would be oriented to be a mirror image of the spacer 35''' shown in FIG. 38.

With spacer 35''' in the position shown in dotted lines in FIG. 41, the protuberances 109a, 109b are received in recesses 111a, 111b and the body of the spacer is positioned between the posts 23a, 23b'. Then upon retraction of the vertebrae spacing and upon the application of compression loading to the implant 101, the protuberances and the recesses will cooperate, as previously described, so as to self-center and to self-align the spacer relative to the body members. Further, with the protuberances received in their respective recesses and with such normal compression loads applied to the implant, the protuberances and recesses will effectively prevent movement or migration of the spacer relative to the body members. Still further, with bone graft material (not shown) packed within the disc space DS on the posterior side of implant 101, the bone graft material will also aid the protuberances and recesses in preventing movement or migration of the space from between the body members. As noted, the spaced wings 115b''', 115c''' substantially prevent both anterior and posterior movement of the spacer relative to the body members 17', 19' beyond a predetermined limited amount of movement.

It will be further appreciated that implants 1 and 101 may be provided in a range of widths, thicknesses, and lengths to readily accommodate taller disc spaces DS and different vertebrae sizes. For example, implants 1, 101 may have heights ranging between 8.5 mm-10.0 mm, to accommodate taller or shorter disc spaces DS and may have widths ranging between about 11-13 mm., and lengths ranging between about 40-60 mm. to accommodate vertebrae having a larger vertebrae footprint.

Referring now to FIGS. 42-59, three additional embodiments of the implant of the present disclosure are illustrated in which the upper and lower surfaces of the implant are angled (tapered from rear to front) so as to provide options for encountered or desired disc space lordosis. Specifically referring to the embodiment shown in FIGS. 42-47, this is an expandable interbody or implant, as indicated in its entirety by reference character 201. The construction of this interbody or implant 201 is similar to the embodiments discussed above and reference characters 217, 219, etc. indicate parts having a similar construction and operation as similar parts identified by similar reference characters 17, 19 etc. of the embodiment illustrated in FIGS. 1-41. Accordingly, only the primary differences between implant 201 and the above-described embodiments will be described in detail. In FIGS. 42-47, the implant is shown in its collapsed or retracted condition with no spacer 35 installed between the inner surfaces of the lower and upper body members 217 and 219. However, it will be understood that with the implant 201 inserted in disc space DS, as described above, and with the lower and upper body members distracted, a spacer 35, 35', 35", or 35''' may be inserted within space 221 between the body members in the manner described above.

Figure 47:
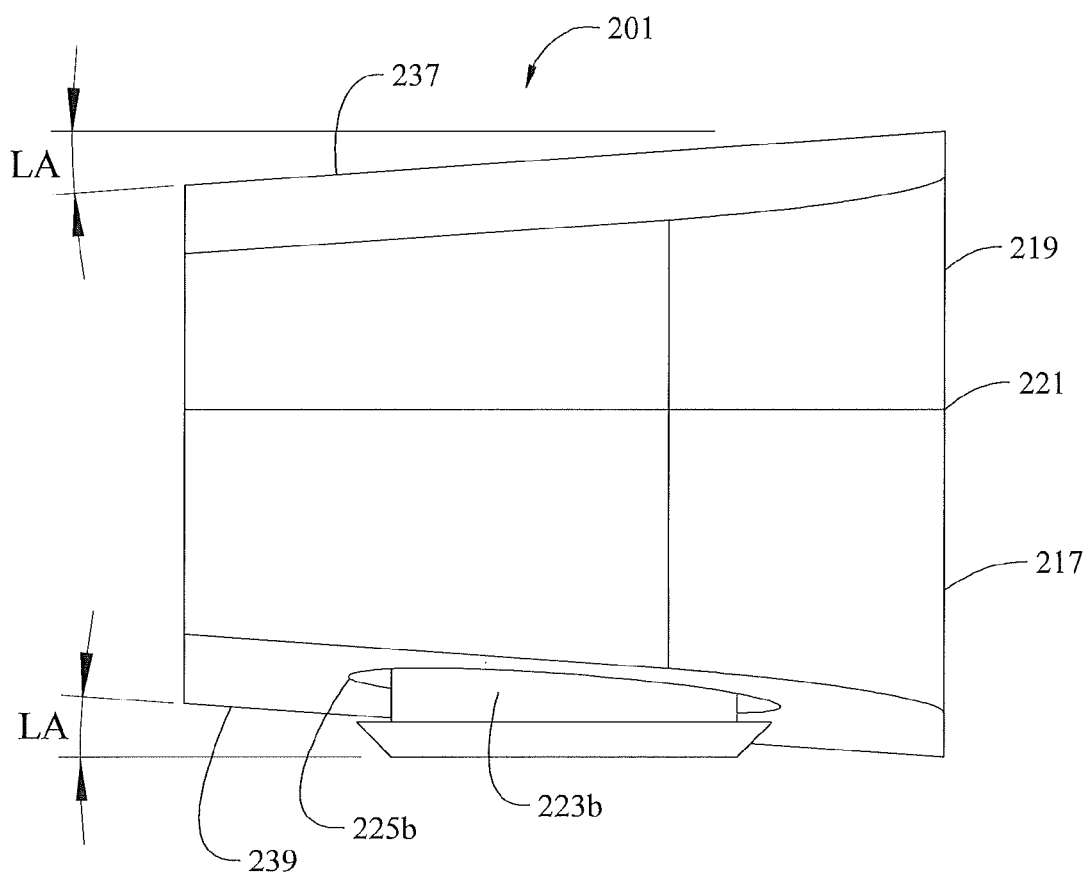
FIG. 47 is a side elevational view of the implant of FIGS. 42-46 on an enlarged scale illustrating a lordosis angle of both the upper and lower body members.
Figure 53:
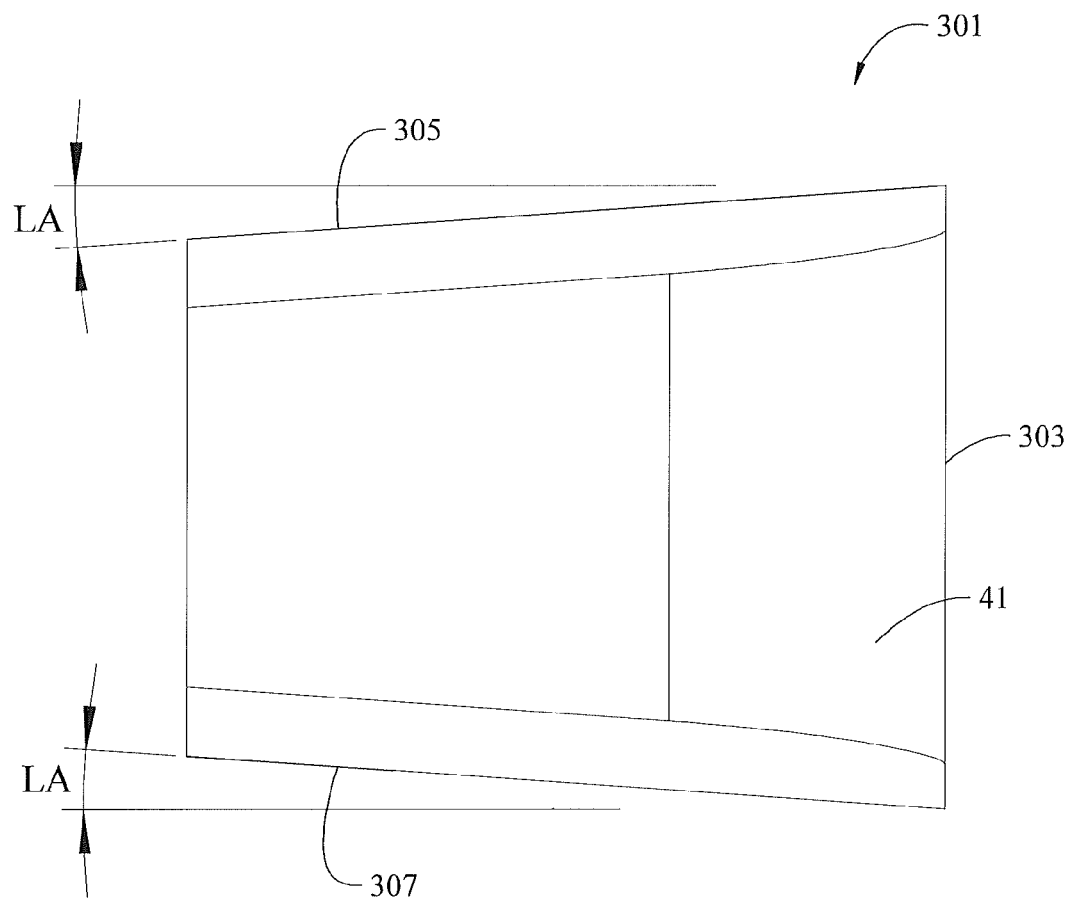
FIG. 53 is a side elevational view of the implant of FIGS. 48-52 on an enlarged scale illustrating the lordosis angles of the upper and lower surfaces of the implant.
Figure 59:
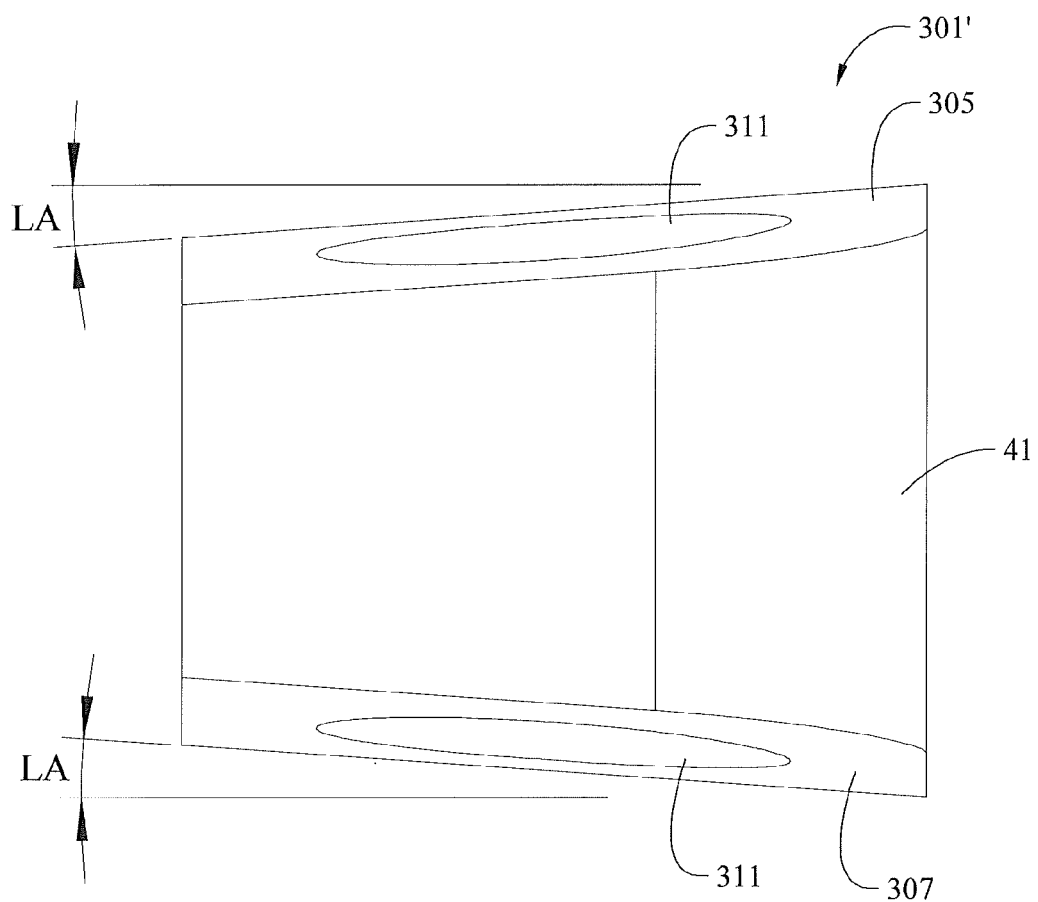
FIG. 59 is a side elevational view of the implant of FIGS. 54-58 on an enlarged scale illustrating a lordosis angle for the upper and lower surfaces of the implant.
Figure 60:
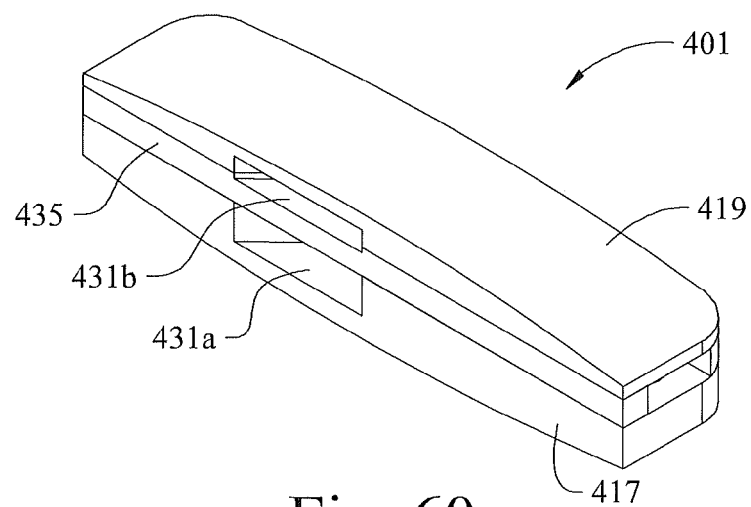
FIG. 60 is posterior top perspective view of still another embodiment of the implant of the present disclosure where the upper and lower body members have a slot in their respective inner faces and where the spacer may have a corresponding slot in register with either the slot in the upper or the lower body member where the posterior ends of these slots may be somewhat wider than the remainder of the slot so as to aid in guiding the operating tips of a distractor or other instrument into the slots.

As perhaps best shown in FIG. 47, the upper face 237 of upper body member 219 and the lower face 239 of lower body member 217 are angled or tapered from rear to front at a lordotic angle LA. The lordotic angles of various implants 201 may range between about 0° and about 12°. It will be appreciated that the lordotic angles of the upper and lower body members may be different. Thus, upon encountering a patient having disc space lordosis, implants 201 having the desired lordotic angles LA, as chosen by the surgeon, may be used so as to reconstruct the spine by maintaining segmental lordosis, regional lordosis, and global sagittal balance. More specifically, upon encountering a need to improve the segmental or disc space lordosis, an implant 201 having a desired predetermined lordosis angle LA may be installed in disc space DS so that with the implant distracted, with an appropriate spacer 35, 35', 35", or 35''' installed in space 21 between the lower and upper body members, with upper and lower faces 237, 239 of the implant engaging the cortical rims CR of the adjacent vertebrae bodies, and with the angled, convex shape of the upper and lower faces of the implant generally conforming to the disc space and contacting the vertebrae endplates, upon distracting the adjacent vertebrae bodies, the desired amount of lordotic correction may be introduced in the reconstructed disc space. It will be also appreciated that because the implant 201 is supported by the cortical rims CR of the vertebrae bodies, there is less of a tendency for subsidence to occur with a consequent loss of disc space height to preoperative levels.

Referring now to FIGS. 49-53, still another embodiment of a non-expandable or fixed height interbody implant in accordance with the present disclosure is shown. This implant is indicated in its entirety by reference character 301. As noted, implant 301 is non-expandable or of fixed height and thus has a one-piece body 303 having an upper surface 305 and a lower surface 307. The rear face of body 303 has a slot 309 therein similar to slot 31 of the above embodiments so that the implant maybe inserted into the disc space DS through annulotomy 11 and maneuvered within the disc space by the surgeon so that the ends of the implant bear on the cortical rims CR of the adjacent vertebrae bodies and such that the implant is positioned generally similar to implant 1, as illustrated in FIG. 4. It is also understood the slot 309 may be replaced by another modification (not shown) of the fixed height implant interbody implant that would allow a surgeon to use a tool to grasp and maneuver the implant in the disc space. The upper and lower faces 305 and 305 are angled or tapered in a manner similar to implant 201 such that these upper and lower faces have a lordotic angle LA, which may range from about 0° to about 12°. Of course, the lordotic angles LA of implant 301 may be used to maintain or correct disc space lordosis in the same manner as described in regard to implant 201.

Turning now to FIGS. 54-59, still another embodiment of the present disclosure is illustrated in its entirety at 301'. This implant 301' is similar to implant 301, as above described, except that it has openings or fenestrations 311 formed therein that may be packed with bone growth material so as to promote bone growth and to aid in fusing the adjacent vertebrae. This augments the bone graft material the surgeon places posterior to the implant for fusing or permanently joining the vertebrae bodies above and below the disc space. It will be understood that such fenestrations may be incorporated in any of the embodiments of the implants of this disclosure.

Figure 61:
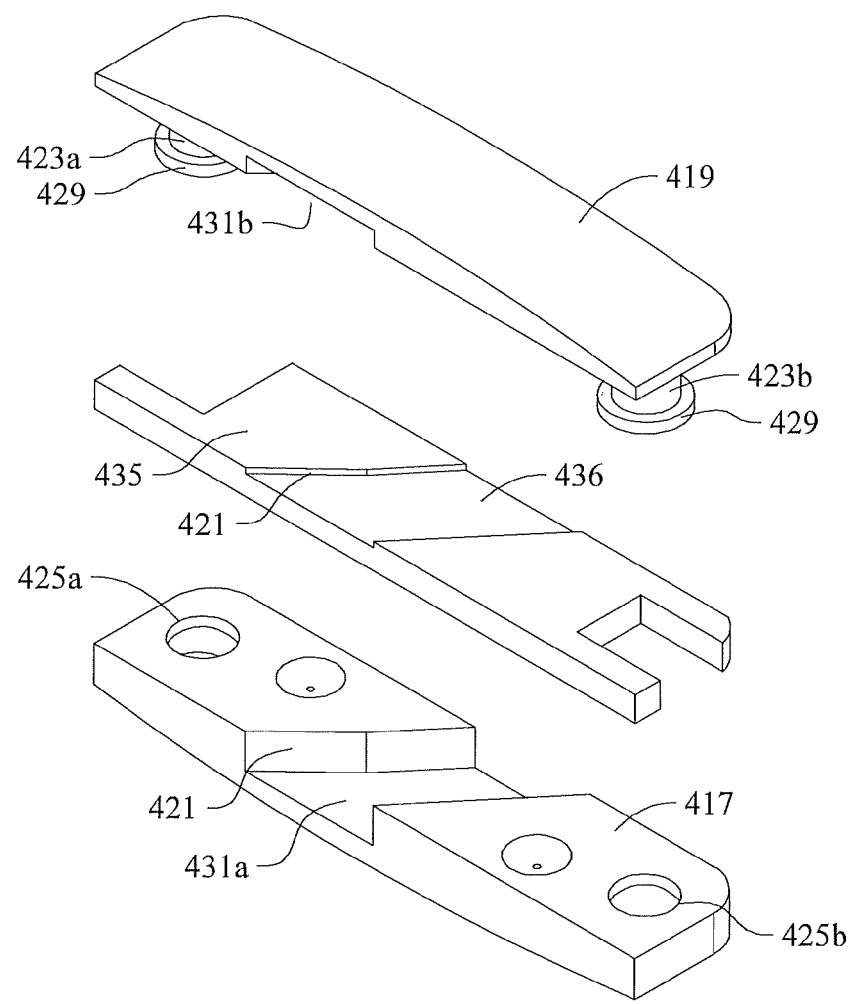
FIG. 61 is an exploded perspective view of the implant shown in FIG. 60, as viewed from above.
Figure 62:
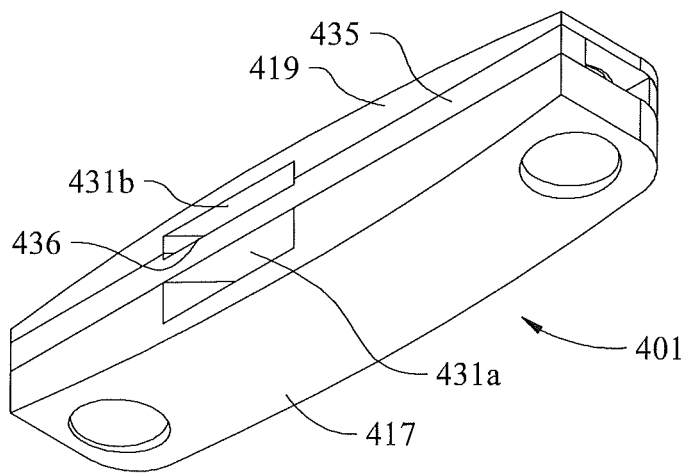
FIG. 62 is a posterior bottom perspective view of the implant shown in FIGS. 60 and 61.
Figure 63:
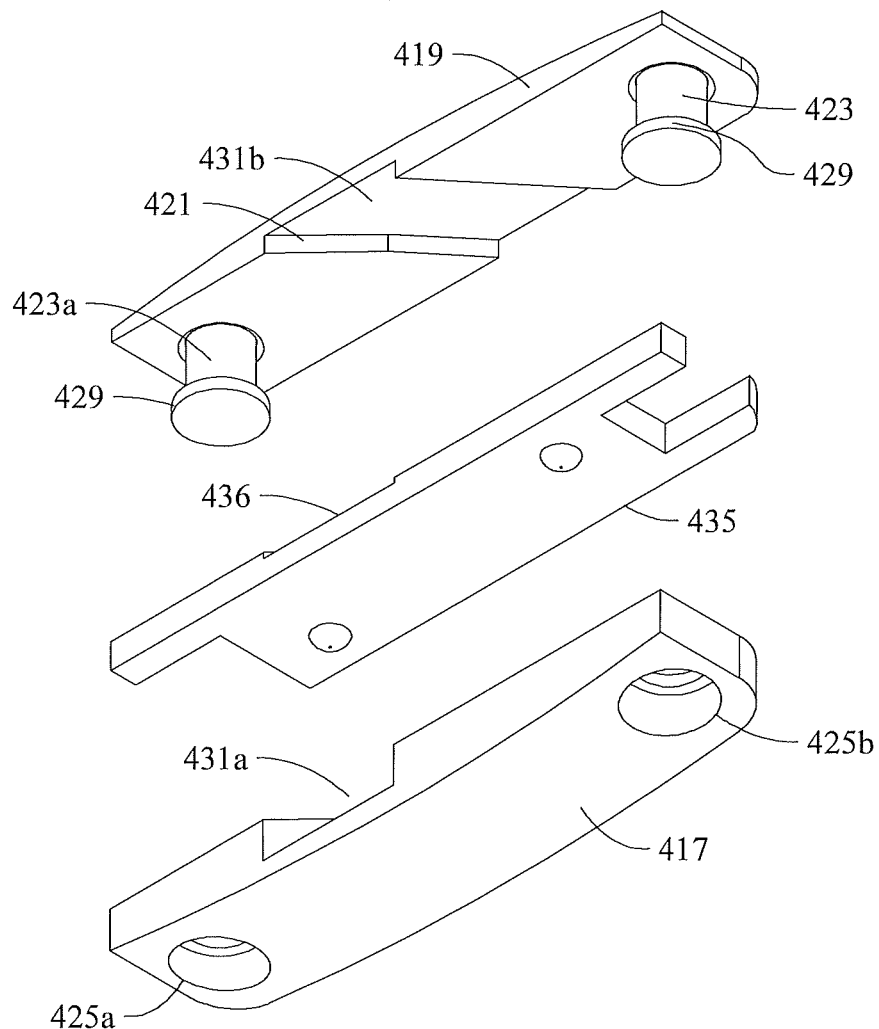
FIG. 63 is an exploded perspective view of the implant shown in FIGS. 60-62 illustrating the slot in the upper face of the spacer.

Referring now to the embodiment of the implant of the present disclosure shown in FIGS. 60-65, this is essentially the same as the implant shown in FIGS. 42-47 and this new embodiment is indicated in its entirety by reference character 401. The various features and parts of implant 401 correspond generally to the corresponding to the features and parts of the body members and spacers shown in FIGS. 42-47, except as particularly pointed out and described below. The implant 401 has a lower body member 417 and an upper body member 419 with a spacer 435 positioned between the inner faces of the upper and lower body members. Spacer 435 is similar to spacer 35" shown in FIGS. 33-36, except that it has an oblique slot 436 (as best shown in FIG. 61) in one face of the spacer that extends through the spacer from its posterior to its anterior edge. Likewise, the lower body member and the upper body member each have a respective oblique slot 431a, 431b in the inner face of each body member that extends through the body from the posterior to the anterior edge of the body member, with these slots being generally in register with one another. As indicated at 421 for each of the slots 436, 431a, and 431b, the posterior portion of these slots is preferably somewhat wider than the anterior portion of the slot so as to aid in guiding a respective operating blade of a distractor or other instrument into the slot, as will be more particularly described below. It will be appreciated that the slot 436 in spacer 435 may be in the bottom face of the spacer, or slots similar to slot 436 may be provided in both the upper and lower faces of the spacer. It will also be appreciated that the slots shown in FIGS. 60-63 are used when the incision 11 (as shown in FIG. 4) is in the posterolateral portion of the annulus 9. However, the angle of the oblique slots may be reversed if the incision 11 is on the contralateral side of the disc space. It will also be appreciated that the lower and upper body members 417, 419 of implant 401 may have their upper and lower faces formed to have the lordotic angles LA, as shown in FIG. 47.

Further, spacer 435 may be provided with wings or extensions, as indicated at 415*a*, 415*b* and 415*c*, to be similar in construction and operation to wings 115*a*''', 115*b*''', and 115*c*''' heretofore described in relation to the embodiment shown in FIGS. 36-41.

Figure 64:
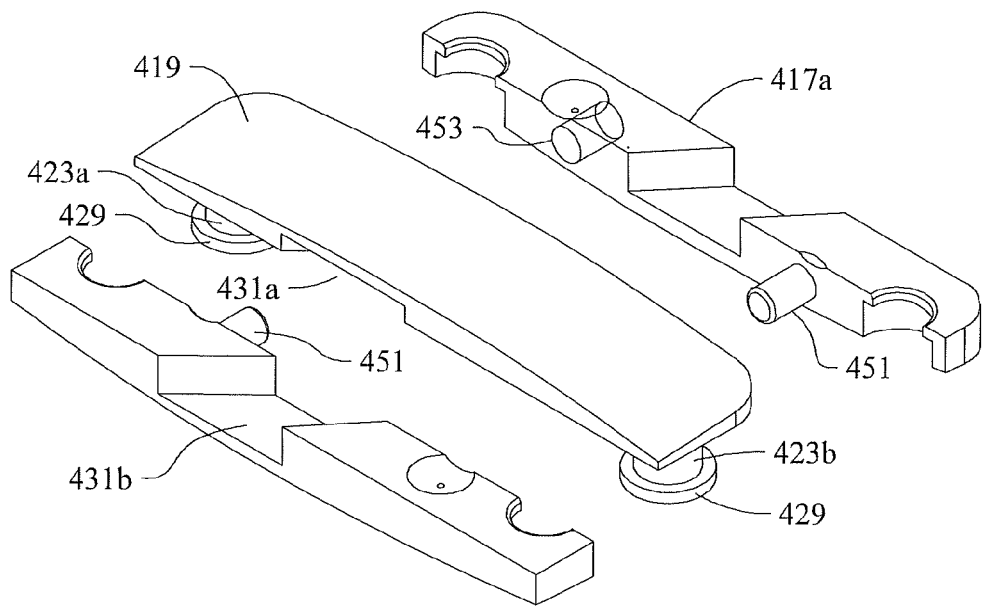
FIG. 64 is a top perspective view of another embodiment of the implant of the present disclosure similar to the implant shown in FIGS. 60-63 with the spacer omitted for illustration purposes, but where the bottom body member is split so that it may be assembled around the flanged posts protruding from the bottom of the upper body member and then adhesively joined so posts are captured in the corresponding holes in the bottom body member, with the halves of the bottom body member each having an alignment pin adapted to be received in a corresponding hole in the opposite bottom body member half.
Figure 65:
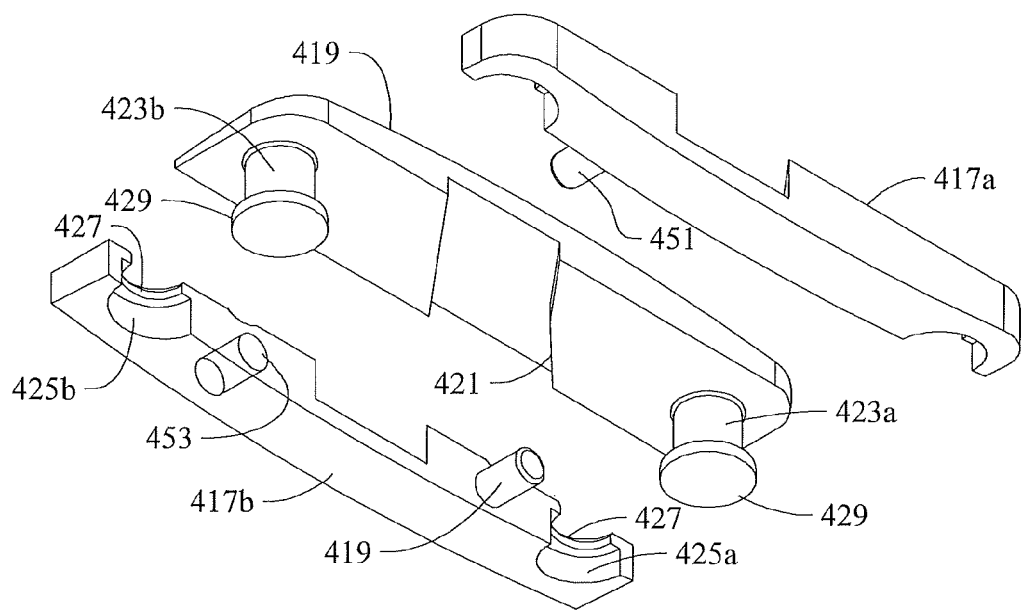
FIG. 65 is a bottom perspective exploded view of the implant shown in FIG. 64.

Referring now to FIGS. 64 and 65, the lower body member 417 of implant 401 has been modified so as to facilitate capture of posts 423*a*, 423*b* of the upper body member 419 by forming the lower body member 417 in two pieces, as indicated at 417*a*, 417*b*. Each of these body pieces has an alignment pin 451 extending from its inner face to be received in a respective bore 453 in the opposite body piece such that the two body pieces 417*a*, 417*b* can be fitted together around posts 423*a*, 423*b* with the flange 429 on the outermost end of the posts received in bores 425*a*, 425*b* with the flange 429 positioned below the inwardly extending flange 427. With each of the alignment pins 451 received in its respective bore 453, the body pieces are in alignment with one another. A suitable adhesive or the like may be used to permanently join the body pieces once they are assembled.

Figure 68:
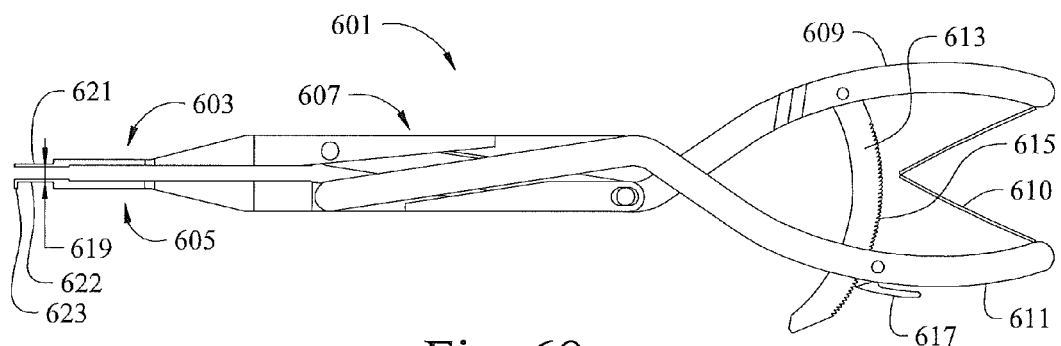
FIG. 68 is a left elevation view of the distractor of FIG. 66 illustrating a gap between the inner surfaces of the operating tips through which a spacer of the implant of the present disclosure may be inserted into the disc space and inserted between the inner surfaces of the distracted upper and lower body members of the implant.
Figure 69:
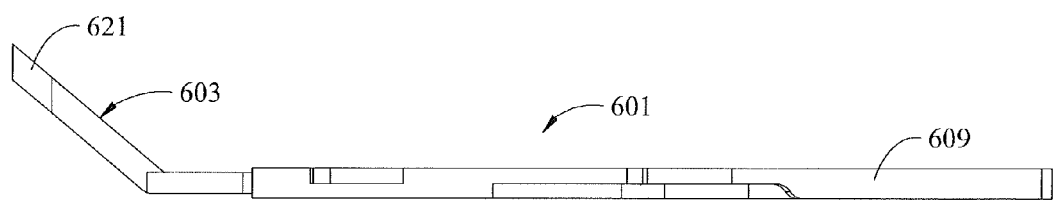
FIG. 69 is a top plan view of the distractor and operating tips of FIG. 68.

Referring now to FIGS. 66-70, a distractor instrument, as indicated in its entirety at 601, is illustrated having upper and lower arms, as generally indicated at 603 and 605, made in accordance with this disclosure. It will be appreciated that the distractor is conventional and it has a parallelogram linkage, as indicated generally at 607, such that upon compressing the handles 609, 611 toward one another, the operating arms or blades 603, 605 are distracted (moved apart) relative to one another and are maintained in generally parallel relation. As is conventional, distractor 601 has a return spring 610 to bias the handles apart from one another and a curved rack 613 pivotally attached to one of the handles and extending through an opening in the other handle with the rack having a plurality of teeth 615 that cooperate with a spring biased pawl 617 (as best shown in FIG. 68) carried by the other handle such that the distractor will automatically lock each time the handles are compressed a distance corresponding to the pitch of the teeth on the rack. In this manner, when the surgeon releases the handles, the distractor will be locked and the desired distraction will be maintained. Of course, the pawl 617 may be disengaged so as to allow retraction.

Figure 70:
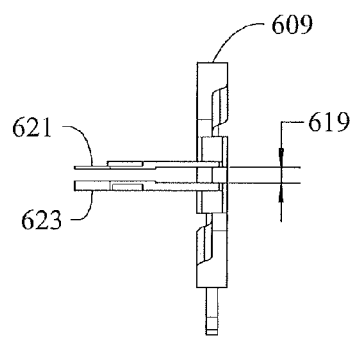
FIG. 70 is a front elevational view of the distractor and operating tips of FIG. 68.

As best shown in FIGS. 66-70, the operating arms 603 and 605 angle obliquely relative to the handles 609, 611 at generally the same oblique angle as the annulotomy incision 11 is positioned within the annulus, as shown in FIG. 4. It will be appreciated that such oblique angle of the operating arm positions the handles of the distractor 601 out of the surgeon's field of view of the operating site. The operating arms 603, 605 each have a respective operating tip, as indicated at 621, 622, on their outer ends and these operating tips are relatively thin and are generally parallel to one another with a space or a gap 619 (as best shown in FIG. 68) between the inner faces of the operating blades. In this disclosure, the term "operating members" may refer to either operating arms 603, 605 and/or to the operating tips 621, 622. With the operating blades inserted into and through slots 431*a*, 431*b* of an implant 401 positioned generally in the disc space DS (as shown in FIG. 4), distractor 601 may be operated to distract both implant 401 and the disc space. With the implant and the disc space so distracted, the obliquely oriented operating arms 603, 605 present an opening formed by gap 619 (as best shown in FIGS. 68 and 70) so as to receive the spacer 435. The spacer is guided by the inner faces of the operating arms 603, 605 and by the inner faces of operating blades 621, 622 as the spacer is moved into position between the upper and lower implant bodies 419, 417, so that the spacer may assume its position as generally shown in FIG. 4.

As shown best in FIG. 68, one of the thin operating blades or tips 621 or 622 may have on its distal end a cleat or hook 623 on its distal end. This cleat may be on either the lower or the upper operating tip, or such cleats may be provided on both the upper and lower operating tips. With the distractor tips 621, 622 inserted through slots 431*a* and 431*b* of the lower and upper implant body members 417 and 419, the cleat 623, which as shown in FIG. 68 is on the lower operating tip 622, engages the anterior face of the lower body member 417 and the sides of the operating tips engage the sides of the slots 431*a*. 431*b* and thus enable the surgeon to engage the anterior face of the lower body member and the sides of the upper and lower body members so that the implant may be readily positioned between the vertebrae in a desired anterior-to-posterior relation and in a desired lateral position generally corresponding to the position of implant 1, as shown in FIG. 4, so that the implant is at least in part supported on the cortical rim CR of the vertebrae. It will be understood that because the posts 423*a*, 423*b* are received in their respective bores 425*a*, 425*b* of the lower body member 417 such that the upper and lower body members are readily moved as a unit upon moving the distractor so as to position the implant within the disc space DS. It will be also understood that with cleat 623 on the lower operating tip 622, the slot 431*a* in the lower body member may be somewhat deeper than the slot 431*b* in the upper body member so as to accommodate cleat 623.

It will be further understood that as the distractor 601 is operated so as to distract the implant and the adjacent vertebrae, a considerable distraction force is applied to the operating arms 603, 605 and tips 621, 622 such that the operating arms and tips may deflect and such that deflection may cause the implant to become displaced from the operating tips. The cleat 623, however, prevents the implant from moving toward the anterior relative to the distractor and thus the cleat aids in keeping the implant in its desired position as the implant and the disc space are distracted. Further, the cleat and the fact that the operating arms have a relatively good fit within slots 431*a*, 431*b*, allow the surgeon to maneuver the implant within the disc space DS to the position shown in FIG. 4. Further, it will be appreciated that the upper and lower faces of tips 621 and 622 of operating arms or blades 603, 605 engage their respective upper and lower body members 419 and 417. Upon operation of distractor 601 by the surgeon, both implant 401 and the disc space DS are distracted. While the operating tips 621, 623 of distractor 601 may be used by the surgeon to maneuver or position the implant 1 within the disc space DS, it will be understood that within the scope of this disclosure, the surgeon may use distractor 601 to distract the adjacent vertebrae and the expandable implant and the surgeon may use another instrument that hooks onto the implant so that it may be readily maneuvered and positioned within the disc space.

As noted, the flared or enlarged ends 421 of slots 431*a*, 431*b* and 436 aid in guiding the operating blades into the slots. It will be appreciated that the upper operating tip 621 may also have a cleat similar to clear 623 (not shown) that extends upwardly. It will be also realized that the thickness of the slots in the spacer and in the upper and lower body members of implant 401 may be appropriately sized to accommodate such upwardly facing cleat.

It will be appreciated that due to the length of the operating arms 603, 605 and the relative thinness of the operating tips 621, 622, and due to the relatively high forces necessary to distract the vertebrae, it is preferable that the operating blades and tips be made of a suitable high strength, high modulus of elasticity material, such as a suitable stainless steel alloy, such as Carpenter 465SS, so as to resist deflection. However, other suitable materials may be used.

Figure 66:
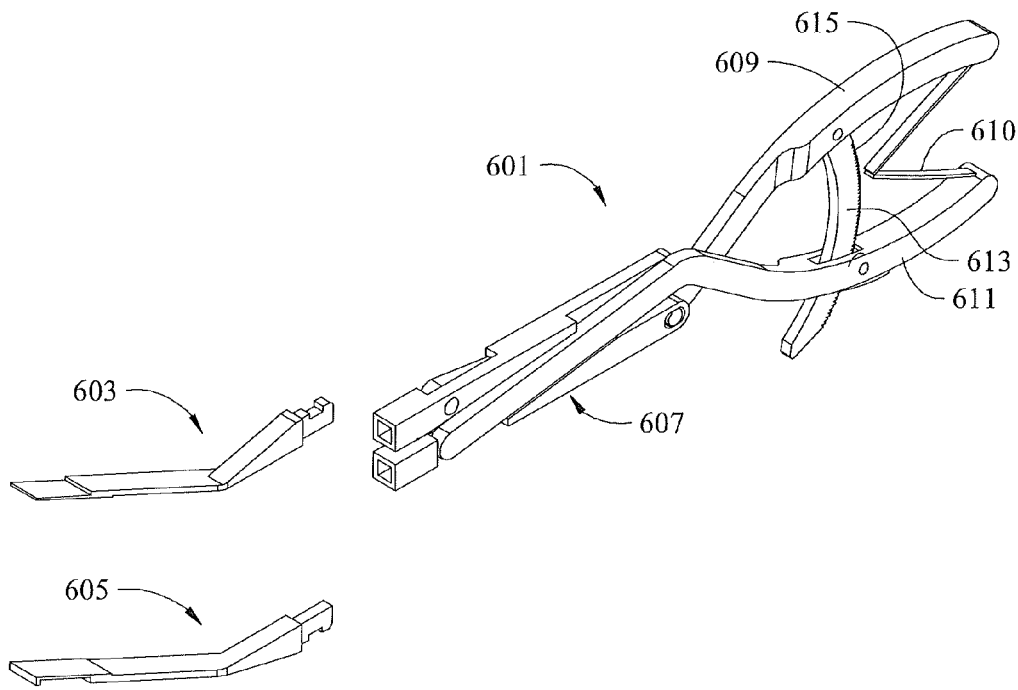
FIG. 66 is an exploded perspective view of a distractor instrument used to distract the implant of this disclosure in situ having operating tips in accordance with the instant disclosure with the distal end of one (or both) of the operating tips having a cleat or hook for engagement with the anterior surface of one of the implant body members when the operating tips are fully inserted into and through the slots in the upper and lower body member such that the cleat engages the implant and allows the implant to be maneuvered within the disc space and allows the implant and the adjacent vertebrae to be distracted without becoming disengaged from the distractor.
Figure 67:
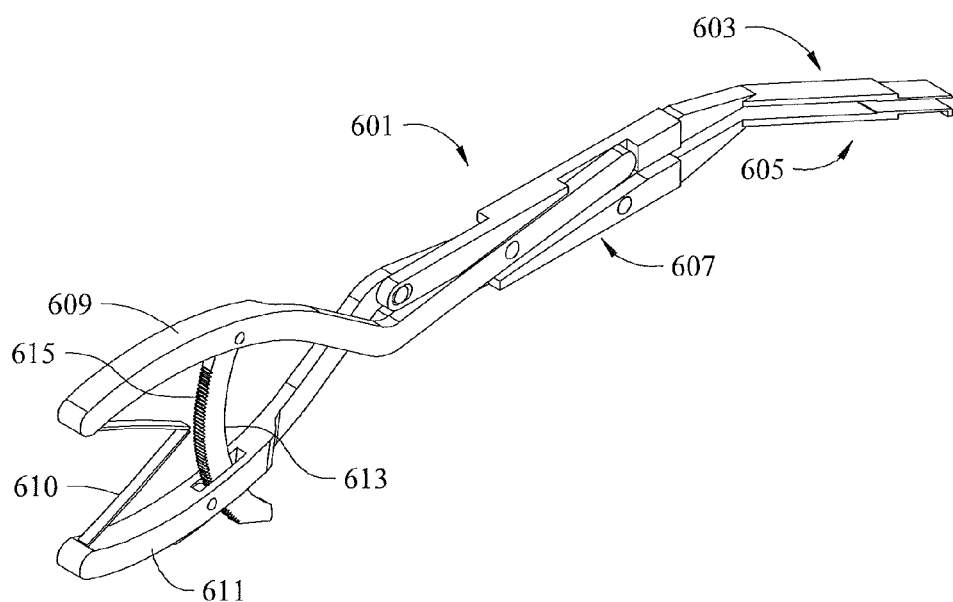
FIG. 67 is a right perspective view of the distractor of FIG. 66 having the operating tips installed.

As described above, annulotomy incision 11 may be formed in the contralateral posterolateral quadrant of the annulus 9. In such case, the slots 436, 431*a*, and 431*b* in implant 401 would be reversed from their positions shown in FIGS. 60-65 so that the slots are generally along the axis of the annulotomy 11. In such case, the distractor 601 would have the angle of its operating arms 603, 605 reversed from the angle shown in FIGS. 66-70. As shown in FIG. 66, the arms 603 and 605 are removably secured to the parallelogram linkage so that they may be installed and removed without the use of tools (e.g., they may be snapped into position). Thus, if it is desired to change the arms 603, 605 for other arms that angle in the opposite direction from the position shown in FIGS. 66-70, the new arms may be readily installed.

Figure 71:
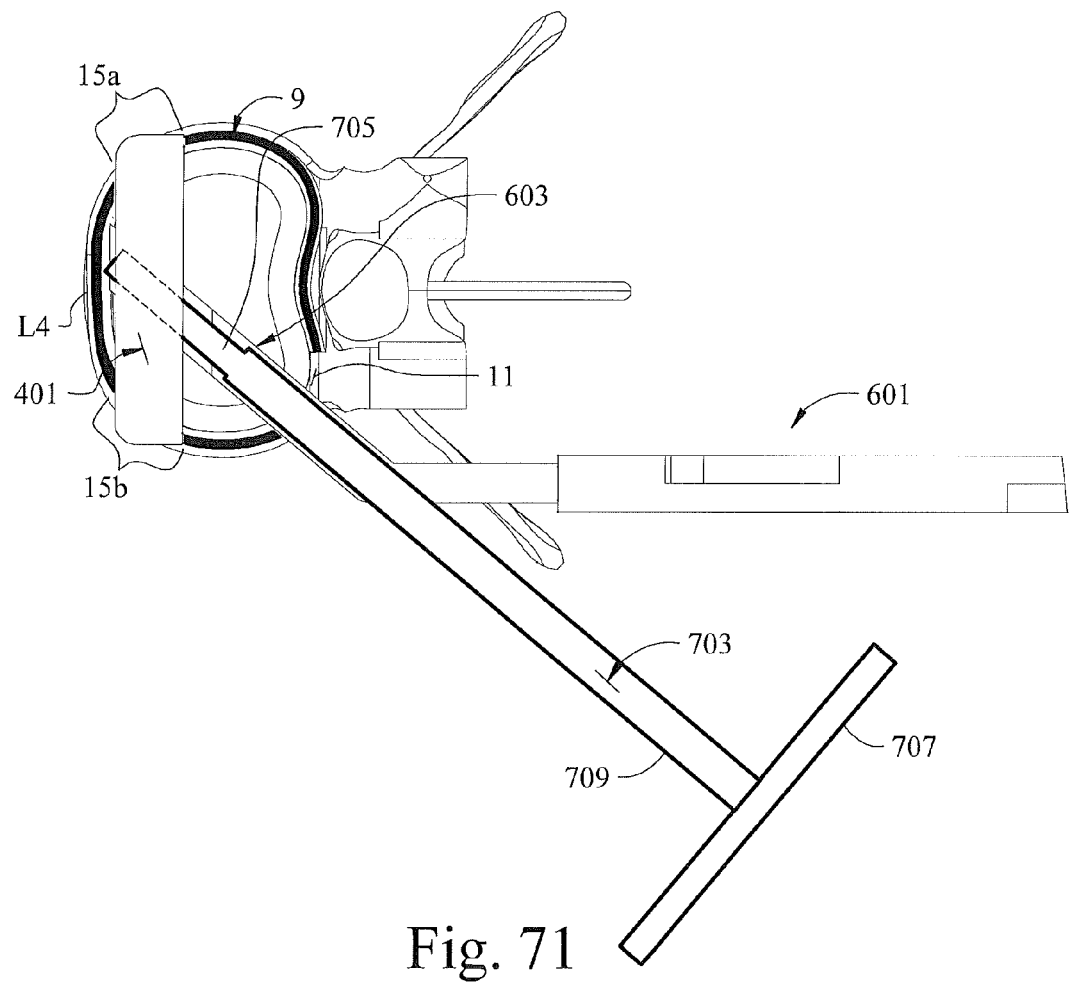
FIG. 71 is a view similar to FIG. 4 showing the distractor of FIGS. 66-70 with its operating tips and operating arms of the distractor inserted through the incision in the posterior lateral quadrant of the annulus with a paddle blade distractor inserted into the gap between the inner faces of the operating arms/tips of the distractor so that upon rotation of the paddle blade distractor about its longitudinal axis by the surgeon the implant of this disclosure and the adjacent vertebrae are distracted a first increment corresponding to the width of the paddle blade distractor so as to insure that the upper and lower implant body members are distracted a first known increment and so as to insure that the operating tips of the distractor are generally parallel.
Figure 72:
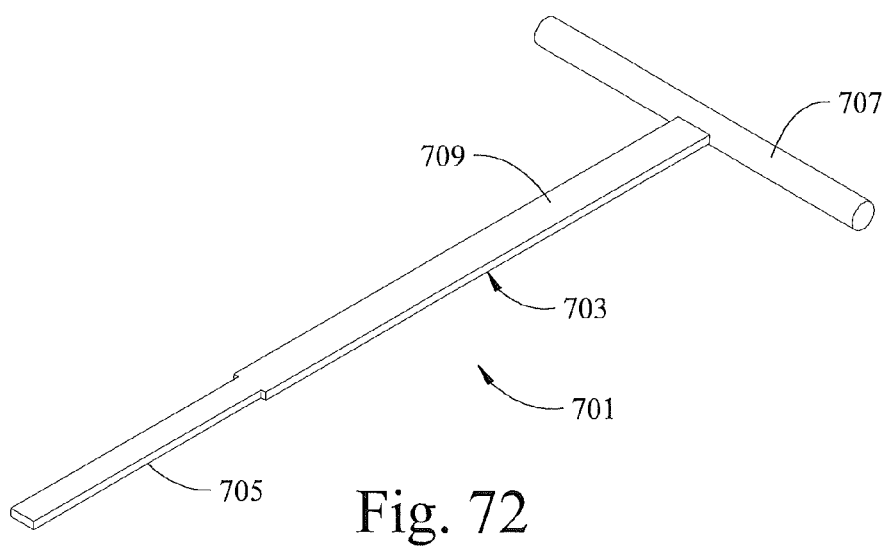
FIG. 72 is a perspective view of a paddle blade distractor having a T-handle and a paddle blade having an operating tip or distal end of a predetermined width.

Referring now to FIGS. 71-75, after the surgeon has installed an implant of the present disclosure, such as indicated at 401, and after the surgeon has operated distractor 601 so as to distract the disc space DS a first amount, a series of paddle blade distractors of different widths, one of which is shown in FIG. 72 and which is generally indicated in its entirety at 701, may be used to insure that the disc space DS and the upper and lower body members 417, 419 of the implant 401 of this disclosure are progressively distracted predetermined amounts corresponding to the width of the particular paddle blade distractor being used until the desired distraction is achieved and so that the operating arms 603, 605 and tips 621 and 622 of distractor 601 are maintained in a generally parallel relation. For example, a set of four (4) paddle blade distractors 701 may be used with each of the paddle blade distractors having a paddle blade 703 with the width of the distal end or operating tip 705 of each of the paddle blades 703 being progressively wider, for example, 3 mm., 5 mm., 7 mm., and 9 mm. Except for the width of the distal ends 705, these paddle blade distractors are generally the same and thus only one will be described in detail. The paddle blades 703 of each of the paddle blade distractors 701 are of the same thickness (e.g., 2 mm.). However, as noted above, the width of the distal end 705 of the paddle blade constituting its operating end has a width corresponding to one of the above-mentioned series widths. A T-handle 707 is affixed to the proximal end 709 of the paddle blade 703. The proximal end 709 of each of the paddle blades has a width greater than the width of its respective distal end or operating tip 705 to provide maximum strength (resistance to torsion or twisting) when the handle 707 is rotated by the surgeon. The sides of the distal end 705 of the operating blade may either be parallel (as shown in FIG. 72), or the sides may have a slight taper.

Figure 73:
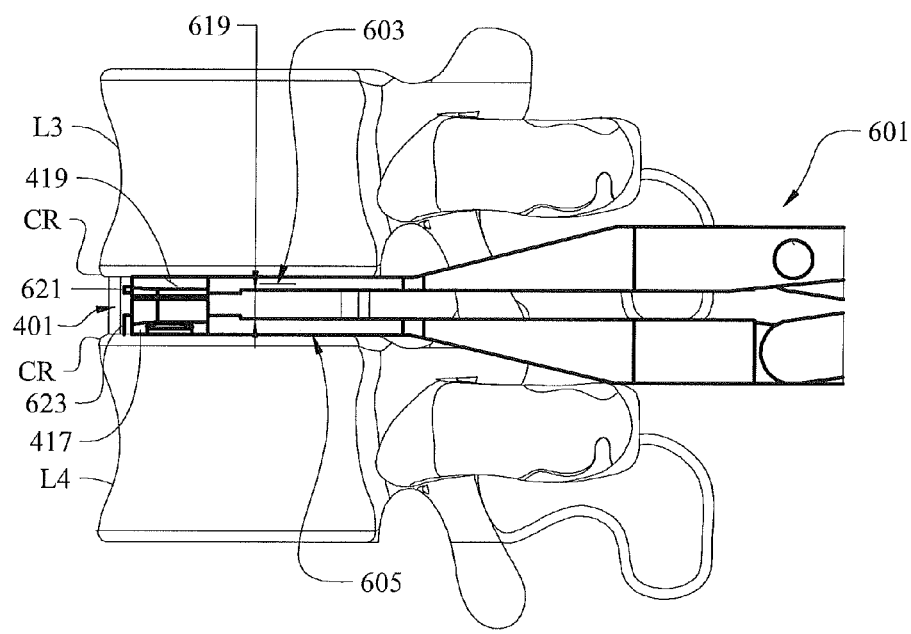
FIG. 73 is a view somewhat similar to FIG. 4 with the annulus omitted for purposes of clarity illustrating the distraction of two adjacent vertebrae (e.g., L3 and L4) with an implant of the present disclosure inserted in the manner shown in FIG. 4 and with the operating tips of a distractor, such as shown in FIGS. 66-70, positioned between the inner faces of the upper and lower body members of the implant so as to distract the implant and the vertebrae upon actuation of the distractor.
Figure 74:
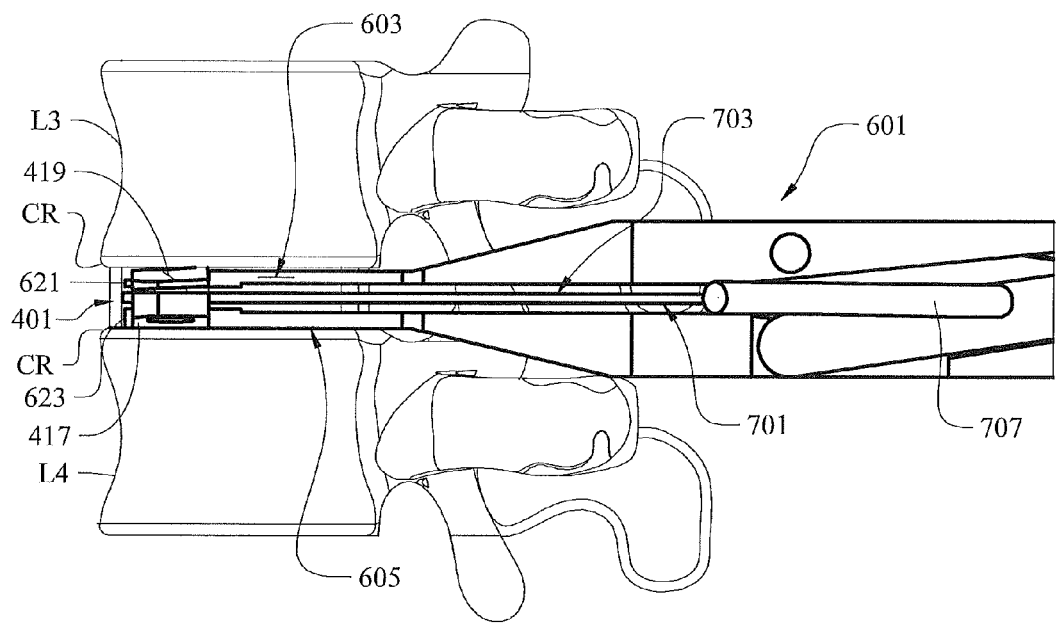
FIG. 74 is a view similar to FIG. 73 illustrating the insertion of a paddle blade distractor, such as shown in FIGS. 71 and 72, inserted between the inner faces of the operating tips of the distractor so as to distract the implant at least the width of the operating tip of the paddle blade distractor and to return the operating tips to a substantially parallel relation to one another in the event that the thin operating tips have deflected somewhat (from the position that they are shown in FIG. 74) upon operation of the parallel distractor.
Figure 75:
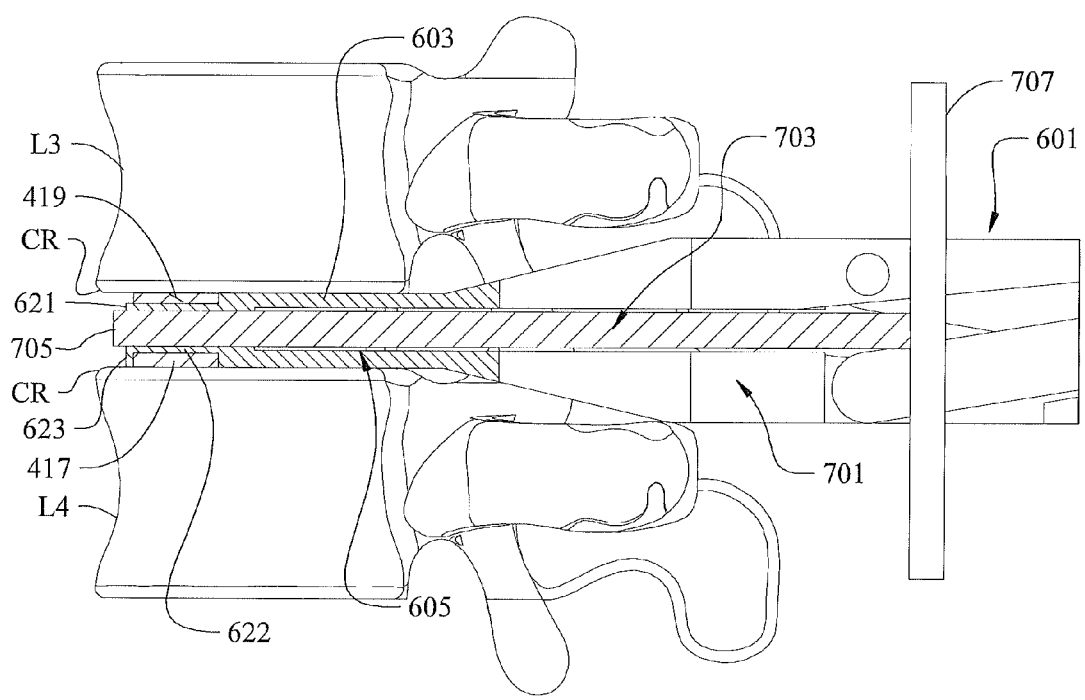
FIG. 75 is a view similar to FIG. 74 with the paddle blade distractor rotated about 90° from its position shown in FIG. 74, and with portions of the operating tips of the parallel distractor, the operating blade of the paddle blade distractor, and the upper and lower body members of the implant being shown in cross section illustrating how the distal end of the paddle blade distractor distracts the implant (and thus also distracts the disc space) and insures that the operating tips of the parallel distractor are returned to a substantially parallel condition upon the paddle blade distractor being rotated approximately 90°.

As shown best in FIG. 73, implant 401 without its spacer 435 installed is positioned in the disc space DS similar to its position as shown in FIGS. 4 and 71. The operating arms 603, 605 and their corresponding operating tips 621, 622 of distractor 601 (as shown by bold lines) are inserted between the inner faces of the upper and lower body members 419 and 417 of implant 401 of the present disclosure. The distractor 601 is then operated so as to distract (force apart) the lower and upper body members 417 and 419 and to distract the disc space DS between adjacent vertebrae (e.g., L3 and L4) a first increment. Then, as shown in FIG. 74, a first paddle blade distractor 701 having the narrowest width (e.g., 3 mm.) operating blade 705 may be inserted into gap 619 between the operating blades 603, 605 and their corresponding operating tips 621, 622 of distractor 601. The surgeon then rotates the T-handle 707 approximately 90° (as shown in FIG. 75) so that the edges of the operating tip or blade 705 bear against the inner faces of the operating tips 621, 622 of distractor 601 thereby to force the operating tips apart at least the width of operating blade 705 (e.g., 3 mm.). As shown best in FIG. 75, because the edges of the operating blade 705 are substantially parallel (or may have a slight taper), as the paddle blade distractor 701 is rotated about the longitudinal axis of blade 703, the side edges of the operating tip 705 insure that the operating arms 603, 605 and the relatively thin tips 621, 622 of distractor 601 are returned to a parallel (or nearly parallel) condition if they deflected as the distractor 601 was actuated. Those skilled in the art will appreciate that when it is stated that the operating blade 705 is inserted within gap 619 and when the operating blade 705 is rotated about its longitudinal axis, the edges of the operating blade may contact the inner surfaces of the operating arms 603, 605, or the edges may or may not also contact the inner surfaces of operating tips 621, 622. Likewise, if the edges of the operating blade bear against the inner faces of the operating tips 621, 622, the edges may or may not engage the inner surfaces of the operating arms 630, 605.

Then, the surgeon may further operate distractor 601 to further distract the disc space and the upper and lower body members of the implant an additional amount. The first paddle blade distractor 701 is removed from between the upper and lower body members 419 and 417 of implant 410 and a next wider paddle blade distractor 701 having an operating blade somewhat wider (e.g., 5 mm.) may be inserted between the inner faces of operating arms 603 and 605 of distractor 601. As shown best in FIG. 75, this second paddle blade distractor 701 is then rotated about 90° so as to insure that the upper and lower body members and the disc space are distracted an amount at least as wide as the width of the next wider paddle blade (e.g., 5 mm.) and to return the operating tips 621, 622 to a parallel relation. This process may be repeated until the disc space has been sufficiently distracted to allow the insertion of the appropriate spacer 435 of implant 401 of the present disclosure. It will be understood that the operating tip 705*a* of the set of paddle blade retractors may have widths different from the 3 mm., 5 mm., 7 mm., and 9 mm widths described above and more or fewer paddle blade distractors 701 may be used in accordance with this disclosure.

In accordance with the present disclosure, a method of distracting and fusing a disc space between two adjacent vertebrae bodies is described including the steps of making an incision in the annulus at the desired level to access a disc space between the adjacent vertebrae to be fused, where the incision is in a posterior lateral quadrant of the annulus and the incision is of sufficient length so as to permit the accommodate surgical instrumentation for performing surgical procedures within the disc space and so as to accommodate endoscopic instrumentation in the disc space so as to enable visualization of the disc space for the surgeon performing the surgical procedures. A discectomy of the disc material is performed within the annulus via the incision in the annulus under endoscopic viewing of the disc space. The endplates of the adjacent vertebrae bodies are prepared under endoscopic viewing of the disc space. It is understood that in accordance with the present disclosure, the surgeon may elect to perform surgical procedures within the disc space without endoscopic visualization. The implant is inserted into the disc space via the incision so as to extend substantially across the vertebrae bodies in the anterior region of the vertebrae bodies. And, the implant and the disc space are distracted a desired amount. It will be understood that the order of the steps of the above method (or any method described in the present disclosure) may not be critical, but as the steps are described in this disclosure, it is necessary to list one step before the other, but in the performance of the method, it is not necessary that the steps be performed in the order described.

As various changes could be made in the above constructions and methods without departing from the scope of the disclosure, it is intended that all matter contained in the above description or shown in the accompanying drawings shall be interpreted as illustrative and not in a limiting sense.

The invention claimed is:

1. A method of distracting and fusing two adjacent vertebrae bodies, each of said adjacent vertebrae bodies having a cortical rim and an endplate with an annulus and a disc space between said adjacent vertebrae bodies, said disc space having an interior within said annulus and further having disc material within the interior of the disc space, said method comprising the following steps:
   a. make an incision in said annulus at a desired level to access the disc space between the adjacent vertebrae bodies, said incision being in a posterior lateral quadrant of said annulus and extending generally from an approximate location of a pedicle in said posterior lateral quadrant to a position in or proximate to an ipsilateral anterior lateral quadrant of said annulus, said incision being of sufficient length so as to simultaneously accommodate the insertion of surgical instrumentation and endoscopic instrumentation into said disc space thereby enabling endoscopic viewing of the interior of the disc space while performing discectomy and while preparing said endplates;
   b. through said incision, perform a discectomy of the disc material within the disc space;
   c. through said incision, prepare the endplates of said adjacent vertebrae bodies;
   d. through said incision, distract said disc space;
   e. through said incision, insert an implant into said disc space via said incision such that one end of said implant is at least partially received in an anterior portion of said incision such that said implant extends across said vertebrae bodies and is at least in part supported by said cortical rim so as to maintain distraction of said disc space; and
   f. through said incision, insert bone graft material in said disc space so as to promote fusing of said adjacent vertebrae bodies.

2. A method of distracting and fusing a disc space between two adjacent vertebrae bodies, said vertebrae bodies each having an annulus and a disc space therebetween, said disc space having an interior within said annulus and further having disc material within the interior of the disc space, said vertebrae bodies further having a cortical rim and an endplate within said annulus, an implant configured to be inserted into said disc space through a posterolateral incision in the annulus and having an elongate body having a height ranging between about 8 mm.-10 mm. and a width ranging between about 11 mm.-13 mm., said implant elongate body being of a length sufficient such that when the implant is positioned in the disc space said implant extends generally laterally of said vertebrae bodies so as to maintain distraction of said adjacent vertebrae bodies, said method comprising the following steps:
   a. make an incision in said annulus at the desired level to access the disc space between the adjacent vertebrae bodies to be fused, said incision being in a posterior lateral quadrant of said annulus and extending generally from an approximate location of a pedicle in said posterior lateral quadrant toward an ipsilateral anterior quadrant of said annulus, said incision being of sufficient length so as to simultaneously accommodate the insertion of surgical instrumentation into the disc space and so as to accommodate the use of endoscopic instrumentation to enable visualization of the disc space while surgical procedures are carried out within the disc space;
   b. perform a discectomy of the disc material within the disc space via said incision;
   c. prepare the endplates of said adjacent vertebrae bodies;
   d. insert said implant into said disc space via said incision so as to extend substantially across said vertebrae bodies in an anterior region of said disc space and so as to be at least in part supported on at least one of said cortical rims of said vertebrae bodies;
   e. distract said disc space; and
   f. insert bone graft material in said disc space so as to promote fusing of said adjacent vertebrae bodies.

3. The method of claim 2 wherein the method further comprises inserting bone growth material into said disc space.

4. The method of claim 2 wherein said implant is an expandable implant having an upper and a lower body member with a space therebetween, and wherein said method further comprises using a distractor while said implant is installed within the disc space and to distract said upper and lower body members and installing a spacer between said upper and lower body members while said implant is distracted within the disc space so as to maintain a desired amount of distraction of said disc space.

5. A method of distracting and fusing two adjacent vertebrae bodies, each of said adjacent vertebrae bodies having a cortical rim and an endplate with an annulus and a disc space therebetween, said disc space having disc material therewithin, said method comprising the following steps:
   a. make an incision in said annulus at a desired level to access the disc space between the adjacent vertebrae bodies, said incision being in a posterior lateral quadrant of said annulus and extending generally from an approximate location of a pedicle in said posterior lateral quadrant to a position in or proximate to an ipsilateral anterior lateral quadrant of said annulus, said incision being of sufficient length so as to accommodate the insertion of surgical instrumentation into the disc space and to enable endoscopic instrumentation to view the interior of said disc space so that discectomy of the disc space and preparation of the endplates of said vertebrae bodies may be performed while the surgeon endoscopically views the disc space;
   b. utilize said endoscopic instrumentation so as to enable viewing of said disc space while performing steps "c" and "d", below;
   c. through said incision, perform a discectomy of the disc material within the disc space;

d. through said incision, prepare the endplates of said adjacent vertebrae bodies;
e. insert an expandable implant into said disc space via said incision;
f. through said incision, distract said implant and said adjacent vertebrae bodies;
g. fix said expandable implant in a desired distracted position within said disc space so as to maintain distraction of said adjacent vertebrae bodies; and
h. through said incision, insert bone graft material in said disc space so as to promote fusing of said adjacent vertebrae bodies.

6. A method of distracting and fusing a disc space between two adjacent vertebrae bodies, said vertebrae bodies each having an annulus and a disc space therebetween, each said vertebrae bodies further having a cortical rim and an endplate within said annulus, an expandable implant having an elongate body configured to have a height ranging between about 8 mm.-10 mm. and a width ranging between about 11 mm.-13 mm. so that said implant may be inserted into the disc space through a posterolateral incision in the annulus, said implant being further configured to have a length so that when the implant is positioned in the disc space the implant extends generally laterally with respect to said vertebrae bodies, said expandable implant being capable of being distracted within said disc space so as to distract said adjacent vertebrae bodies and being capable of being fixed in a desired distracted condition so as to maintain a desired amount of distraction between said adjacent vertebrae bodies, said method comprising the following steps:
 a. make an incision in said annulus at the desired level to access the disc space between the adjacent vertebrae bodies to be fused, said incision being substantially in a posterior lateral quadrant of said annulus and extending generally from an approximate location of a pedicle in said posterior lateral quadrant to a position in or proximate to an ipsilateral anterior lateral quadrant of said annulus, said incision being of sufficient length so as to accommodate surgical instrumentation for performing surgical procedures within said disc space and so as to permit the use of endoscopic instrumentation so as to enable the surgeon to visualize the interior of the disc space while performing said surgical procedures;
 b. utilize endoscopic instrumentation for viewing of said disc space;
 c. perform a discectomy of the disc space via said incision in said annulus under endoscopic viewing of the disc space;
 d. prepare the endplates of said adjacent vertebrae bodies under endoscopic viewing of the disc space;
 e. insert said expandable implant into said disc space via said incision so as to extend generally laterally of said vertebrae bodies in an anterior region thereof;
 f. distract said expandable implant and said adjacent vertebrae bodies;
 g. fix said expandable implant and said adjacent vertebrae bodies in a desired distracted condition; and
 h. insert bone graft material in said disc space so as to promote fusing of said adjacent vertebrae bodies.

7. The method of claim 6 wherein said expandable implant is supported by at least a portion on said cortical rim.

8. The method of claim 7 wherein said expandable implant is supported on at least a portion on said cortical rim.

9. A method of distracting and fusing two adjacent vertebrae bodies, each of said adjacent vertebrae bodies having a cortical rim and an endplate with an annulus and a disc space therebetween, said method comprising the following steps:
 a. make an incision in said annulus at a desired level to access the disc space between the adjacent vertebrae bodies, said incision being in a posterior lateral quadrant of said annulus and extending generally from an approximate location of a pedicle in said posterior lateral quadrant to a position in or proximate to an ipsilateral anterior lateral quadrant of said annulus, said incision being of sufficient length so as to accommodate surgical instrumentation for performing surgical procedures within said disc space and so as to permit the use of endoscopic instrumentation so as to enable the surgeon to visualize the interior of the disc space while performing at least some of said surgical procedures;
 b. through said incision, perform a discectomy of the disc material within the disc space while under endoscopic viewing by said surgeon;
 c. through said incision, prepare the endplates of said adjacent vertebrae bodies while under endoscopic viewing by said surgeon;
 d. insert an implant into said disc space via said incision;
 e. through said incision, distract said adjacent vertebrae bodies with said implant maintaining a desired distraction of said adjacent vertebrae bodies; and
 f. through said incision, insert bone graft material in said disc space so as to promote fusing of said adjacent vertebrae bodies.

10. A method of fusing two adjacent vertebrae bodies, each of said adjacent vertebrae bodies having a cortical rim and an endplate with an annulus and a disc space between said adjacent vertebrae bodies, said disc space having an interior within said annulus and further having disc material within the interior of the disc space, said method comprising the following steps:
 a. make an incision in said annulus at a desired level to access the disc space between the adjacent vertebrae bodies, where at least a portion of said incision is in a posterior lateral quadrant of said annulus and where said incision is of a sufficient length so as to accommodate the insertion of endoscopic instrumentation into said disc space so as to enable viewing of the interior of the disc space and so as to permit the insertion of surgical instrumentation into said disc space for performing discectomy of the disc space and for preparing the endplates of said vertebrae bodies;
 b. perform a discectomy of the disc material within the disc space;
 c. prepare the endplates of said adjacent vertebrae bodies;
 d. form an opening in an anterior contralateral side of said annulus;
 e. distract said disc space;
 f. insert an implant into said disc space via said incision such that said implant extends across said vertebrae bodies with said implant being at least in part supported by said cortical rim and maintaining distraction of said disc space; and
 g. insert bone graft material in said disc space so as to promote fusing of said adjacent vertebrae bodies.

11. The method of claim 10 wherein said implant comprises an expandable implant having an upper and a lower body member, and wherein said method further comprises:
 h. using a distractor having operating members, inserting the operating members of said distractor between said upper and lower body members and distracting said body members and said adjacent vertebrae bodies.

12. The method of claim 11 further comprising:
 i. wherein after said distractor has been operated to distract said adjacent vertebrae bodies a first distance, inserting a first paddle blade distractor between said operating members of said distractor, said paddle blade distractor having a predetermined width at least as great as the distance between said operating members of said distractor when said vertebrae bodies have been distracted a distance generally corresponding to said first distance;

j. rotating said first paddle distractor blade about its longitudinal axis so as to insure that said distractor operating members are distracted at least the width of said first paddle blade distractor and so as to insure that the operating members of said distractor are substantially parallel; and k. inserting a spacer between said upper and lower body members of said expandable implant so as to maintain a desired amount of distraction of said adjacent vertebrae bodies.

13. The method of claim 12 further comprising:

l. wherein prior to performing step k, removing said first paddle blade distractor from between said operating members of said distractor, and operating said distractor so as to distract said adjacent vertebrae bodies a second distance greater than said first distance; and m. inserting a second paddle blade distractor between said operating members of said distractor where said second paddle blade distractor is wider than said first paddle blade distractor and then rotate said second paddle blade distractor about its longitudinal axis so as to insure that said distractor operating members are distracted at least the width of said second paddle blade distractor and are substantially parallel.

14. The method of claim 11 wherein said expandable implant further comprises a spacer, and wherein said method comprises inserting said spacer between said upper and lower body members so as to maintain distraction of said vertebrae members.

15. The method of claim 10 further comprising:

h. installing one end of said implant in said opening and installing another end of said implant in the anterior portion of said incision such that said implant is oriented to extend across said adjacent vertebrae bodies and is at least in part supported on at least one of the cortical rims of said vertebrae bodies.

16. The method of claim 10 wherein said expandable implant includes a spacer, and wherein said method further comprises inserting said spacer between said upper and lower body members of said expandable implant after said upper and lower body members have been distracted.

17. The method of claim 10 wherein said implant comprises an expandable implant having an upper and a lower body member, each of said body members having an outer surface and an inner surface with a space between said inner surfaces and wherein said implant upper and lower body members are movable toward and away from one another, and wherein said method further comprises:

h. with said implant installed across said vertebrae bodies, using a distractor having operating members, inserting the operating members of said distractor between said upper and lower body members and distracting said body members; and i. after distracting said upper and lower body members, inserting a spacer between said upper and lower body members.

18. The method of claim 10 further comprising extending said opening in said anterior contralateral side of said annulus toward the posterior for relaxation of the annulus.

19. The method of claim 10 wherein said incision extends at least in part into an adjacent anterior lateral quadrant of said annulus.

20. The method of claim 19 wherein said opening extends posteriorly into an adjacent lateral posterior quadrant of said annulus.

21. The method of claim 10 wherein said opening constitutes a first opening, and wherein said method further comprises forming a second opening in an opposite anterior quadrant of said annulus generally opposite said first opening and inserting a first end of said implant into said first opening and inserting a second end of said implant into said second opening.

22. A method of distracting and fusing a disc space between two adjacent vertebrae bodies, said vertebrae bodies each having an annulus and a disc space therebetween, said disc space having disc material therein, each said vertebrae bodies further having a cortical rim and an endplate within said annulus, an expandable implant having an elongate body of a length sufficient such that when the implant is positioned in the disc space said implant extends across said vertebrae bodies and is at least in part supported by at least one of said cortical rims of said adjacent vertebrae bodies, said expandable implant having a lower body member and an upper body member movable toward and away from one another and having a spacer configured to be inserted between said upper and lower body members so as to maintain distraction of said adjacent vertebrae bodies, said method comprising the following steps:

a. make an incision in said annulus at the desired level to access the disc space between the adjacent vertebrae bodies to be fused, said incision being substantially in a posterior lateral quadrant of said annulus and being of sufficient length so as to accommodate surgical instrumentation for performing surgical procedures within said disc space and so as to accommodate endoscopic instrumentation in said disc space so as to enable visualization of the disc space for the surgeon performing said surgical procedures;

b. perform a discectomy of the disc space via said incision in said annulus under endoscopic viewing of the disc space;

c. prepare the endplates of said adjacent vertebrae bodies under endoscopic viewing of the disc space;

d. form an opening in an anterior contralateral side of said annulus;

e. insert said expandable implant into said disc space via said incision so as to extend substantially across said vertebrae bodies in an anterior region of said disc space and so as to be at least in part supported by at least one of said cortical rims;

f. distract said expandable implant and said disc space;

g. insert said spacer between said upper and lower body members of said expandable implant so as to substantially maintain distraction of said adjacent vertebrae bodies; and h. insert bone graft material in said disc space so as to promote fusing of said adjacent vertebrae bodies.

23. The method of claim 22 further comprising the following steps:

i. wherein said step of distracting said expandable implant includes inserting the operating members of a distractor between said upper and lower body members of said implant and operating said distractor to distract said body members such that a gap is present between said operating members; and wherein said step of inserting said spacer between said upper and lower body members of said expandable implant comprises placing said spacer within said gap between said operating blades and moving said spacer to its desired position between said upper and lower spacer body members.

24. The method of claim 23 further comprising:
j. after said distractor has been operated to distract said vertebrae bodies a first distance and prior to inserting said spacer between said upper and lower body members of said expandable implant, inserting a first paddle blade distractor having a predetermined width at least as great as the distance between said operating members of said distractor when said vertebrae bodies have been distracted a distance generally corresponding to said first distance, and
k. rotating said paddle distractor blade about its longitudinal axis so as to insure that said distractor blades are distracted at least the width of said first paddle blade distractor thereby to insure that the operating members and tips of said distractor are substantially parallel.

25. The method of claim 24 further comprising:
l. removing said first paddle blade distractor and operating said distractor so as to distract said vertebrae a second distance greater than said first distance; and
m. inserting a second paddle blade distractor between said operating members of said distractor where said second paddle blade distractor is wider than said first paddle blade distractor and then rotating said second paddle blade distractor.

26. The method of claim 22 further comprising:
i. wherein said step of inserting said implant further involves inserting one end of said implant in said opening and to orient said implant to extend across said vertebrae bodies with another end of said implant received in an anterior portion of said incision.

27. The method of claim 22 further comprising:
i. after inserting said spacer between said body members, installing bone growth material in said disc space.

28. A method of distracting a disc space between two adjacent vertebrae bodies to be fused together, said adjacent vertebrae bodies having an annulus and a disc space therebetween with disc material within the disc space, each of said adjacent vertebrae bodies further having a cortical rim and an endplate within said annulus, said method comprising the following steps:
a. make an incision in said annulus at the desired level to access a disc space between the adjacent vertebrae to be fused, a portion of said incision being in a posterior lateral quadrant of said annulus and extending anteriorly at least partially into a proximate anterior quadrant of said annulus, said incision being of sufficient length so as to accommodate surgical instrumentation for performing surgical procedures within said disc space and so as to accommodate endoscopic instrumentation in said disc space;
b. perform a discectomy of the disc space via said incision in said annulus under endoscopic viewing of the disc space;
c. prepare the endplates of said adjacent vertebrae bodies under endoscopic viewing of the disc space;
d. form an opening in an anterior contralateral side of said annulus;
e. provide an implant having an elongate body of a length sufficient such that when the implant is positioned in an anterior portion of said disc space said implant extends across said vertebrae bodies; and
f. insert said implant into said disc space via said incision and positioning the implant so as to extend substantially across said adjacent vertebrae bodies in the anterior region of said vertebrae bodies with one end of said implant being at least partially received in said opening and with another end of said implant being at least partially received in an anterior portion of said incision so that said implant is at least in part supported by at least one of said cortical rims upon retraction of said disc space.

29. A method of distracting a disc space between two adjacent vertebrae bodies to be fused together, said vertebrae bodies having an annulus and a disc space therebetween with disc material within the disc space, each of said vertebrae bodies further having a cortical rim and an endplate within said annulus, said method comprising the following steps:
a. make an incision in said annulus at the desired level to access a disc space between the adjacent vertebrae to be fused, said incision being substantially in a posterior lateral quadrant of said annulus;
b. perform a discectomy of the disc material within the annulus via said incision;
c. prepare the endplates of said adjacent vertebrae bodies;
d. form a first opening in an anterior contralateral side of said annulus;
e. form a second opening in said annulus substantially opposite said first opening;
f. insert an expandable implant into said disc space via said incision, said implant having ends that are received in said first and second openings such that the implant extends substantially across said vertebrae bodies in an anterior region of said vertebrae bodies and is at least in part supported by at least one of said cortical rims;
g. distract said expandable implant; and
h. install a spacer between said upper and lower bodies of said implant so as to maintain distraction.

* * * * *